(12) United States Patent
Jewett et al.

(10) Patent No.: US 8,703,936 B2
(45) Date of Patent: Apr. 22, 2014

(54) COMPOSITIONS AND METHODS FOR MODIFICATION OF BIOMOLECULES

(71) Applicant: The Regents of the University of California, Oakland, CA (US)

(72) Inventors: John C. Jewett, Berkeley, CA (US); Carolyn R. Bertozzi, Berkeley, CA (US); Ellen May Sletten, Berkeley, CA (US); Chelsea G. Gordon, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/962,636

(22) Filed: Aug. 8, 2013

(65) Prior Publication Data

US 2014/0045207 A1 Feb. 13, 2014

Related U.S. Application Data

(62) Division of application No. 13/024,908, filed on Feb. 10, 2011, now Pat. No. 8,519,122.

(60) Provisional application No. 61/304,208, filed on Feb. 12, 2010.

(51) Int. Cl.
*C07D 225/04* (2006.01)

(52) U.S. Cl.
USPC .......................................... 540/451; 540/461

(58) Field of Classification Search
USPC ................................................ 540/451, 461
See application file for complete search history.

(56) References Cited

U.S. PATENT DOCUMENTS

| 7,807,619 B2 | 10/2010 | Bertozzi et al. |
| 2009/0068738 A1 | 3/2009 | Bertozzi et al. |

FOREIGN PATENT DOCUMENTS

| WO | WO 2006/050262 | 5/2006 |

OTHER PUBLICATIONS

Ning et al., "Visualizing Metabolically Labeled Glycoconjugates of Living Cells by Copper-Free and Fast Huisgen Cycloadditions", Angew. Chem. Int., 2008, 47, 2253-2255.

*Primary Examiner* — Bruck Kifle
(74) *Attorney, Agent, or Firm* — Paula A. Borden; Bozicevic, Field & Francis LLP.

(57) ABSTRACT

Provided are modified cycloalkyne compounds; and methods of use of such compounds in modifying biomolecules. Embodiments include a cycloaddition reaction that can be carried out under physiological conditions. The cycloaddition reaction involves reacting a modified cycloalkyne with an azide moiety on a target biomolecule, generating a covalently modified biomolecule. The selectivity of the reaction and its compatibility with aqueous environments provide for its application in vivo and in vitro.

21 Claims, 13 Drawing Sheets

COMPOSITIONS AND METHODS FOR MODIFICATION OF BIOMOLECULES

CROSS-REFERENCE

This application is a divisional of U.S. patent application Ser. No. 13/024,908, filed Feb. 10, 2011, now U.S. Pat. No. 8,519,122, which claims the benefit of U.S. Provisional Patent Application No. 61/304,208, filed Feb. 12, 2010, which applications are incorporated herein by reference in their entirety.

STATEMENT REGARDING FEDERALLY SPONSORED RESEARCH

This invention was made with government support under Grant No. GM58867 awarded by the National Institutes of Health. The government has certain rights in the invention.

INTRODUCTION

Selective chemical reactions that are orthogonal (e.g., do not interact or interfere with biology) to the diverse functionality of biological systems are now recognized as important tools in chemical biology. As relative newcomers to the repertoire of synthetic chemistry, these bioorthogonal reactions have inspired new strategies for compound library synthesis, protein engineering, functional proteomics, and chemical remodeling of cell surfaces. The azide has secured a prominent role as a unique chemical handle for bioconjugation.

The azide group has an alternative mode of bioorthogonal reactivity: the [3+2] cycloaddition with alkynes described by Huisgen. In its classic form, this reaction has limited applicability in biological systems due to the requirement of elevated temperatures (or pressures) for reasonable reaction rates. Sharpless and coworkers surmounted this obstacle with the development of a copper(I)-catalyzed version, termed "click chemistry," that proceeds readily at physiological temperatures and in richly functionalized biological environs. This discovery has enabled the selective modification of virus particles, nucleic acids, and proteins from complex tissue lysates. Unfortunately, the mandatory copper catalyst is toxic to both bacterial and mammalian cells, thus precluding applications wherein the cells must remain viable. Catalyst-free Huisgen cycloadditions of alkynes activated by electron-withdrawing substituents have been reported to occur at ambient temperatures. However, these compounds undergo Michael reaction with biological nucleophiles.

SUMMARY

Provided are modified cycloalkyne compounds; and methods of use of such compounds in modifying biomolecules. Embodiments include a cycloaddition reaction that can be carried out under physiological conditions. The cycloaddition reaction involves reacting a modified cycloalkyne with an azide moiety on a target biomolecule, generating a covalently modified biomolecule. The selectivity of the reaction and its compatibility with aqueous environments provide for its application in vivo (e.g., on the cell surface or intracellularly) and in vitro (e.g., synthesis of peptides and other polymers, production of modified (e.g., labeled) amino acids).

Figure 1:
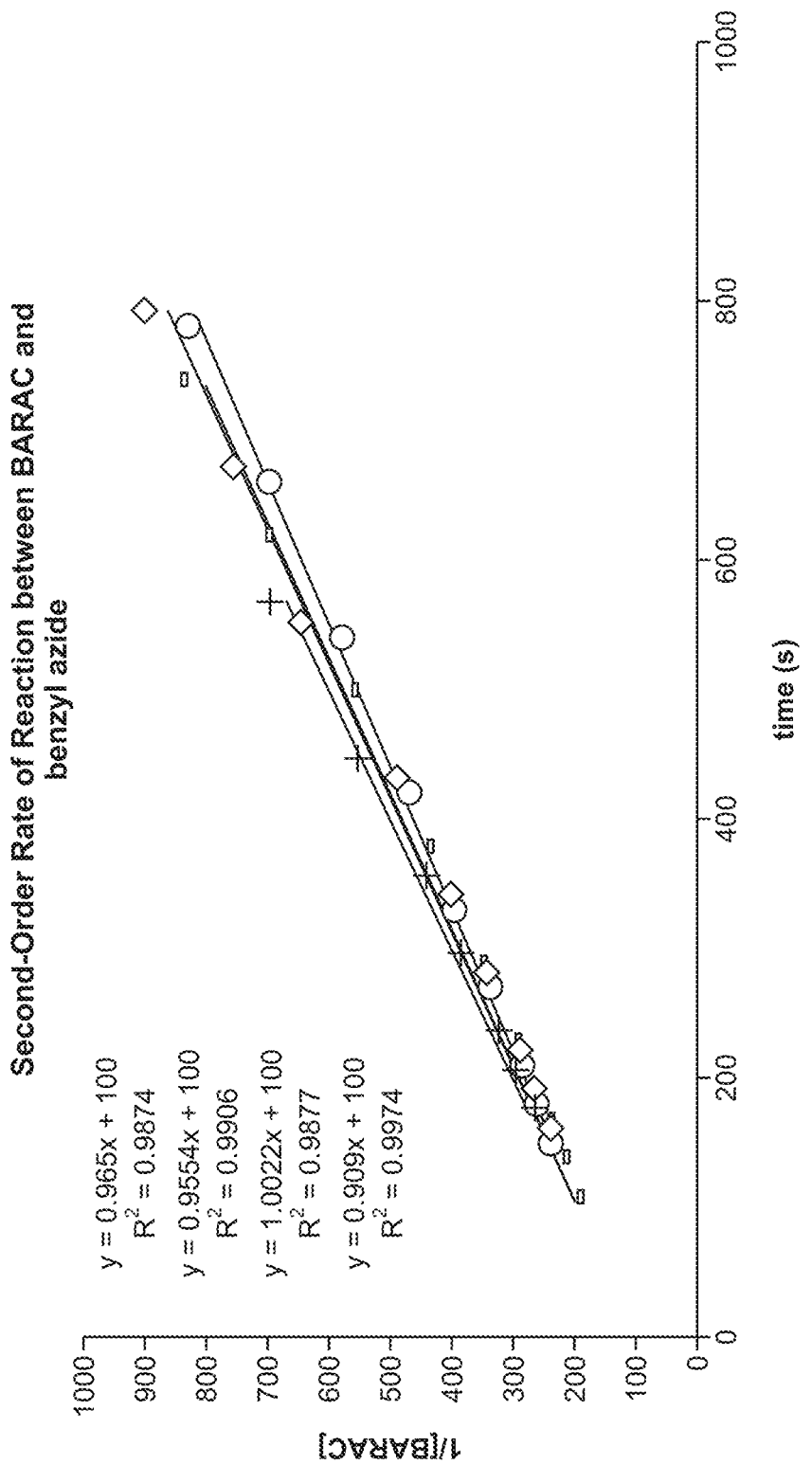
FIG. 1 shows a graph of the rate of reaction between BARAC (compound 15) and benzyl azide over time according to embodiments of the present disclosure.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an azacycloalkynone compound" includes a plurality of such compounds and reference to "the azide moiety" includes reference to one or more azide moieties and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

By "reactive partner" is meant a molecule or molecular moiety that specifically reacts with another reactive partner. Exemplary reactive partners are those of the reaction of the invention, i.e., an azide group of an azide-modified target molecule and the cycloalkyne group of a modified cycloalkyne moiety.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment or its synthetic environment and is at least 60% free, at least 75% free, at least 90% free, at least 95% free, at least 98% free, or at least 99% free from other components with which it is naturally associated, or is at least 60% free, at least 75% free, at least 90% free, at least 95% free, at least 98% free, or at least 99% free from contaminants associated with synthesis of the compound.

As used herein, the term "cell" in the context of the in vivo applications of the invention is meant to encompass eukaryotic and prokaryotic cells of any genus or species, with mammalian cells being of particular interest. "Cell" is also meant to encompass both normal cells and diseased cells, e.g., cancerous cells. In many embodiments, the cells are living cells.

The terms "polypeptide" and "protein," used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "physiological conditions" is meant to encompass those conditions compatible with living cells, e.g., predominantly aqueous conditions of a temperature, pH, salinity, etc. that are compatible with living cells.

The term "aryl" as used herein means 5- and 6-membered single-aromatic radicals which may include from zero to four heteroatoms. Representative aryls include phenyl, thienyl, furanyl, pyridinyl, (is)oxazoyl and the like.

The term "lower alkyl", alone or in combination, generally means an acyclic alkyl radical containing from 1 to about 10, e.g., from 1 to about 8 carbon atoms, or from 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, iso-propyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, triloromethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

The terms "halo" and "halogen" refer to the fluoro, chloro, bromo or iodo groups. There can be one or more halogen, which are the same or different.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl) hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(isopropyl)phenyl, 2, 3, or 4-ethylphenyl, 2, 3 or 4-(n-propyl) phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl)ethyl, 4-(2',6'-dihydroxy phenyl)n-hexyl, 2-(5'-cyano-3'-methoxyphenyl) n-pentyl, 3-(2',6'-dimethylphenyl)n-propyl, 4-chloro-3-aminobenzyl, 6-(4'-methoxyphenyl)-3-carboxy(n-hexyl), 5-(4'-aminomethylphenyl)-3-(aminomethyl)n-pentyl, 5-phenyl-3-oxo-n-pent-1-yl, (4-hydroxynapth-2-yl)methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, e.g., to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature, or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

DETAILED DESCRIPTION

Embodiments of the present disclosure feature a strain-promoted [3+2]cycloaddition reaction that can be carried out under physiological conditions. A modified cycloalkyne may be reacted with an azide moiety on a biomolecule, generating a covalently modified biomolecule. The selectivity of the reaction and its compatibility with aqueous environments provides for its application in vivo (e.g., on the cell surface or intracellularly) and in vitro (e.g., synthesis of peptides and other polymers, production of modified (e.g., labeled) amino acids). In certain embodiments, the reaction is compatible with modification of living cells.

Aspects of the present disclosure provide methods and compositions for specifically and efficiently synthetically modifying cellular components in an aqueous environment. In some cases, the subject methods and compositions provide for modification of cellular components on or in living cells. Reactive partners may be used that are completely abiotic and are chemically orthogonal to native cellular components. In certain instances, reactive partners that are abiotic and bioorthogonal provide for extreme selectivity of the reaction. Furthermore, the reaction can be carried out under physiological conditions, e.g., a pH of about 7 within an aqueous environment, and at about 37° C.

Embodiments of the present disclosure are based in part on the discovery of a means for carrying out a modified Huisgen reaction that can be carried out in an aqueous, physiological environment. Because the reaction is highly selective and functions in aqueous solvents, the reaction can be used in a variety of applications both in vitro and in vivo. The reaction is accomplished through use of a first molecule that includes a strained cycloalkyne moiety, and second molecule that includes an azide moiety. The azide moiety on the second molecule reacts, in the absence of a catalyst, with the strained cycloalkyne moiety on the first molecule, forming a final conjugate product that includes a fused azide/cycloalkyne ring. The first molecule having the strained cycloalkyne moiety can further include a moiety that allows for subsequent reactions and/or which provides for detectable labeling of the product of the final reaction. The reaction proceeds without the need for a catalyst. Instead, the activation energy for the reaction is provided by the azide group and the strained cycloalkyne group. The reaction takes advantage of the significant bond angle deformation of the acetylene group in the cycloalkyne moiety, which provides for ring strain. For example, bond angle deformation of the acetylene group of cyclooctyne to 1630 accounts for nearly 18 kcal/mol of ring strain. This destabilization of the ground state versus the transition state of the reaction provides an accelerated reaction rate compared to unstrained alkynes.

Modified Cycloalkyne Compounds

Embodiments of the present disclosure include modified cycloalkyne compounds; and compositions that include the compounds. In certain embodiments, the modified cycloalkyne compounds include azacycloalkynone compounds. A subject azacycloalkynone is a compound of the formula:

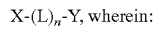
X-(L)$_n$-Y, wherein:

X is a strained azacycloalkynone group, optionally substituted with Y, and in some embodiments one or more additional groups, and wherein the strained azacycloalkynone group comprises at least two sp$^2$ centers vicinal to each other;

each L is a divalent moiety independently selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;

each n is a number selected from zero to 40; and

Y is H; a moiety that comprises a reactive group that facilitates covalent attachment of a molecule of interest; or a molecule of interest.

In some embodiments, Y is H.

In some embodiments, Y is a reactive group. Suitable reactive groups include, but are not necessarily limited to, carboxyl, amine, (e.g., alkyl amine (e.g., lower alkyl amine), aryl amine), ester (e.g., alkyl ester (e.g., lower alkyl ester, benzyl ester), aryl ester, substituted aryl ester), thioester, sulfonyl halide, alcohol, alkoxide, thiol, succinimidyl ester, isothiocyanate, iodoacetamide, maleimide, hydrazine, hydrazide, carbonyl, halogen, cyano, diazo, azide, guanidine, sulfone, epoxide, diazirine, alkene, alkyne, phosphine, silane, alkylsulfonic acid and the like. In some embodiments, Y is a reactive group selected from a carboxyl, an amine, an ester, a thioester, a sulfonyl halide, an alcohol, an alkoxide, a thiol, a succinimidyl ester, an isothiocyanate, an iodoacetamide, a maleimide, a hydrazine, a hydrazide, a carbonyl, a halogen, a cyano, a diazo, an azide, a guanidine, a sulfone, an epoxide, a diazirine, an alkene, an alkyne, a phosphine, a silane, and an alkylsulfonic acid.

In some embodiments, Y is a molecule of interest, where suitable molecules of interest include, but are not limited to, a detectable label; a toxin (including cytotoxins); a peptide; a drug; a member of a specific binding pair; an epitope tag; a strained azacycloalkynone group; and the like.

The azacycloalkynone is a strained azacycloalkynone, e.g., the azacycloalkynone increases the rate of reaction from about 2-fold to about 1000-fold, e.g., the azacycloalkynone increases the rate of reaction at least about 2-fold, at least about 5-fold, at least about 10-fold, at least about 50-fold, at least about 100-fold, at least about 500-fold, or at least about 1000-fold, compared to the rate of reaction between an azide and a linear alkyne having the same number of carbon atoms as the azacyclooctynone. The strain on the azacycloalkynone can be increased in a variety of ways, e.g., through the use of heteroatoms; the degree of unsaturation, or torsional strain; the use of electron-withdrawing groups (e.g., a halo (bromo, chloro, fluoro, iodo), a nitro group, a cyano group, a sulfone group, and the like), etc. In some embodiments, the azacycloalkynone is an azacyclooctynone.

Formula I

In some embodiments, a subject azacycloalkynone compound is of Formula I:

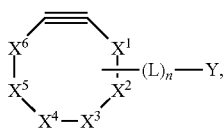

Formula I wherein
five of $X^1$-$X^6$ are carbon atoms;
one of $X^1$-$X^6$ is nitrogen;
the $X^1$-$X^6$ that is vicinal to the $X^1$-$X^6$ that is nitrogen is C=O;
at least two of $X^1$-$X^6$ are $sp^2$ centers vicinal to each other;
each L is a divalent moiety independently selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;
each n is a number selected from zero to 40; and
Y is H; a moiety that comprises a reactive group that facilitates covalent attachment of a molecule of interest; or a molecule of interest.

In some embodiments, in Formula I, one of $X^2$-$X^5$ is nitrogen. In some embodiments, in Formula I, one of $X^3$ and $X^4$ is nitrogen.

In some embodiments, in Formula I, at least four of $X^1$-$X^6$ are $sp^2$ centers vicinal to each other. In some embodiments, in Formula I, $X^1$ and $X^2$ are $sp^2$ centers vicinal to each other. In some embodiments, in Formula I, $X^5$ and $X^6$ are $sp^2$ centers vicinal to each other. In some embodiments, in Formula I, $X^2$ and $X^3$ are $sp^2$ centers vicinal to each other.

In some embodiments, in Formula I, at least one of $X^1$-$X^2$ is the carbon of a carbonyl group. In some embodiments, in Formula I, at least one of $X^3$ and $X^4$ is the carbon of a carbonyl group. In some embodiments, in Formula I, at least one of $X^4$ and $X^5$ is the carbon of a carbonyl group. In some embodiments, the carbonyl group is the carbonyl of an amido group. In some embodiments, the carbonyl group is the carbonyl of an urea group.

In some embodiments, Y is H.

In some embodiments, Y is a reactive group. Suitable reactive groups include, but are not necessarily limited to, carboxyl, amine, (e.g., alkyl amine (e.g., lower alkyl amine), aryl amine), ester (e.g., alkyl ester (e.g., lower alkyl ester, benzyl ester), aryl ester, substituted aryl ester), thioester, sulfonyl halide, alcohol, alkoxide, thiol, succinimidyl ester, isothiocyanate, iodoacetamide, maleimide, hydrazine, hydrazide, carbonyl, halogen, cyano, diazo, azide, guanidine, sulfone, epoxide, diazirine, alkene, alkyne, phosphine, silane, alkylsulfonic acid and the like. In some embodiments, Y is a reactive group selected from a carboxyl, an amine, an ester, a thioester, a sulfonyl halide, an alcohol, an alkoxide, a thiol, a succinimidyl ester, an isothiocyanate, an iodoacetamide, a maleimide, a hydrazine, a hydrazide, a carbonyl, a halogen, a cyano, a diazo, an azide, a guanidine, a sulfone, an epoxide, a diazirine, an alkene, an alkyne, a phosphine, a silane, and an alkylsulfonic acid.

In some embodiments, Y is a molecule of interest, where suitable molecules of interest include, but are not limited to, a detectable label; a toxin (including cytotoxins); a peptide; a drug; a member of a specific binding pair; an epitope tag; a strained azacycloalkynone group; and the like.

Formula II

In some embodiments, a subject azacycloalkynone compound is of Formula II:

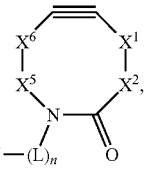

Formula II wherein
at least two of $X^1$, $X^2$, $X^5$, and $X^6$ are $sp^2$ centers vicinal to each other (e.g., $X^1$ and $X^2$, and/or $X^5$ and $X^6$);
each L is a divalent moiety independently selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;
each n is a number selected from zero to 40; and
Y is H; a moiety that comprises a reactive group that facilitates covalent attachment of a molecule of interest; or a molecule of interest.

In some embodiments, Y is H.

In some embodiments, Y is a reactive group. Suitable reactive groups include, but are not necessarily limited to, carboxyl, amine, (e.g., alkyl amine (e.g., lower alkyl amine), aryl amine), ester (e.g., alkyl ester (e.g., lower alkyl ester, benzyl ester), aryl ester, substituted aryl ester), thioester, sulfonyl halide, alcohol, alkoxide, thiol, succinimidyl ester, isothiocyanate, iodoacetamide, maleimide, hydrazine, hydrazide, carbonyl, halogen, cyano, diazo, azide, guanidine, sulfone, epoxide, diazirine, alkene, alkyne, phosphine, silane, alkylsulfonic acid and the like. In some embodiments, Y is a reactive group selected from a carboxyl, an amine, an ester, a thioester, a sulfonyl halide, an alcohol, an alkoxide, a thiol, a succinimidyl ester, an isothiocyanate, an iodoacetamide, a maleimide, a hydrazine, a hydrazide, a carbonyl, a halogen, a cyano, a diazo, an azide, a guanidine, a sulfone, an epoxide, a diazirine, an alkene, an alkyne, a phosphine, a silane, and an alkylsulfonic acid.

In some embodiments, Y is a molecule of interest, where suitable molecules of interest include, but are not limited to, a detectable label; a toxin (including cytotoxins); a peptide; a drug; a member of a specific binding pair; an epitope tag; a strained azacycloalkynone group; and the like.

Formula III

In some embodiments, a subject azacycloalkynone compound is of Formula III:

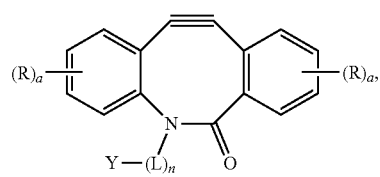

Formula III wherein

L is a divalent moiety selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;

n is a number selected from zero to 40;

each R is independently selected from alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, thioketo, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl;

each a is a number selected from zero to four; and

Y is H; a moiety that comprises a reactive group that facilitates covalent attachment of a molecule of interest; or a molecule of interest.

In Formula III, the —(R)$_a$ represents one or more optional aryl substituents (e.g., 1, 2, 3 or 4 aryl substituents), each R group independently attached to any suitable carbon of the aryl ring.

In some embodiments, Y is H.

In some embodiments, Y is a reactive group. Suitable reactive groups include, but are not necessarily limited to, carboxyl, amine, (e.g., alkyl amine (e.g., lower alkyl amine), aryl amine), ester (e.g., alkyl ester (e.g., lower alkyl ester, benzyl ester), aryl ester, substituted aryl ester), thioester, sulfonyl halide, alcohol, alkoxide, thiol, succinimidyl ester, isothiocyanate, iodoacetamide, maleimide, hydrazine, hydrazide, carbonyl, halogen, cyano, diazo, azide, guanidine, sulfone, epoxide, diazirine, alkene, alkyne, phosphine, silane, alkylsulfonic acid and the like. In some embodiments, Y is a reactive group selected from a carboxyl, an amine, an ester, a thioester, a sulfonyl halide, an alcohol, an alkoxide, a thiol, a succinimidyl ester, an isothiocyanate, an iodoacetamide, a maleimide, a hydrazine, a hydrazide, a carbonyl, a halogen, a cyano, a diazo, an azide, a guanidine, a sulfone, an epoxide, a diazirine, an alkene, an alkyne, a phosphine, a silane, and an alkylsulfonic acid.

In some embodiments, Y is a molecule of interest, where suitable molecules of interest include, but are not limited to, a detectable label; a toxin (including cytotoxins); a peptide; a drug; a member of a specific binding pair; an epitope tag; a strained azacycloalkynone group; and the like.

Formula IV

In some embodiments, a subject azacycloalkynone compound is of Formula IV:

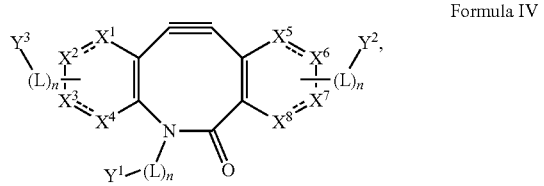

Formula IV where $X^1$-$X^8$ are each independently selected from carbon (e.g., CH or CR), nitrogen and silicon (e.g., Si—R);

each L is a divalent moiety selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;

each n is a number independently selected from zero to 40;

each R is independently selected from alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, thioketo, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; and $Y^1$-$Y^3$ are each independently selected from H; a moiety that comprises a reactive group that facilitates covalent attachment of a molecule of interest; or a molecule of interest.

In some embodiments, $Y^1$-$Y^3$ are each H.

In some embodiments, at least one of $Y^1$-$Y^3$ is a reactive group. Suitable reactive groups include, but are not necessarily limited to, carboxyl, amine, (e.g., alkyl amine (e.g., lower alkyl amine), aryl amine), ester (e.g., alkyl ester (e.g., lower alkyl ester, benzyl ester), aryl ester, substituted aryl ester), thioester, sulfonyl halide, alcohol, alkoxide, thiol, succinimidyl ester, isothiocyanate, iodoacetamide, maleimide, hydrazine, hydrazide, carbonyl, halogen, cyano, diazo, azide, guanidine, sulfone, epoxide, diazirine, alkene, alkyne, phosphine, silane, alkylsulfonic acid and the like. In some embodiments, Y is a reactive group selected from a carboxyl, an amine, an ester, a thioester, a sulfonyl halide, an alcohol, an alkoxide, a thiol, a succinimidyl ester, an isothiocyanate, an iodoacetamide, a maleimide, a hydrazine, a hydrazide, a carbonyl, a halogen, a cyano, a diazo, an azide, a guanidine, a sulfone, an epoxide, a diazirine, an alkene, an alkyne, a phosphine, a silane, and an alkylsulfonic acid.

In some embodiments, at least one of $Y^1$-$Y^3$ is a molecule of interest, where suitable molecules of interest include, but are not limited to, a detectable label; a toxin (including cytotoxins); a peptide; a drug; a member of a specific binding pair; an epitope tag; a strained azacycloalkynone group; and the like.

Formula V

In some embodiments, an azacycloalkynone compound is of Formula V:

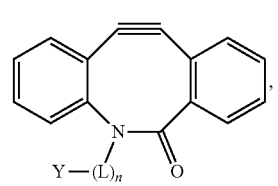

Formula V wherein

L is a divalent moiety selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;

n is a number selected from zero to 40; and

Y is H; a moiety that comprises a reactive group that facilitates covalent attachment of a molecule of interest; or a molecule of interest.

In some embodiments, Y is H.

In some embodiments, Y is a reactive group. Suitable reactive groups include, but are not necessarily limited to, carboxyl, amine, (e.g., alkyl amine (e.g., lower alkyl amine), aryl amine), ester (e.g., alkyl ester (e.g., lower alkyl ester, benzyl ester), aryl ester, substituted aryl ester), thioester, sulfonyl halide, alcohol, alkoxide, thiol, succinimidyl ester, isothiocyanate, iodoacetamide, maleimide, hydrazine, hydrazide, carbonyl, halogen, cyano, diazo, azide, guanidine, sulfone, epoxide, diazirine, alkene, alkyne, phosphine, silane, alkylsulfonic acid and the like. In some embodiments, Y is a reactive group selected from a carboxyl, an amine, an ester, a thioester, a sulfonyl halide, an alcohol, an alkoxide, a thiol, a succinimidyl ester, an isothiocyanate, an iodoacetamide, a maleimide, a hydrazine, a hydrazide, a carbonyl, a halogen, a cyano, a diazo, an azide, a guanidine, a sulfone, an epoxide, a diazirine, an alkene, an alkyne, a phosphine, a silane, and an alkylsulfonic acid.

In some embodiments, Y is a molecule of interest, where suitable molecules of interest include, but are not limited to, a detectable label; a toxin (including cytotoxins); a peptide; a drug; a member of a specific binding pair; an epitope tag; a strained azacycloalkynone group; and the like.

Formula VI

In some embodiments, an azacycloalkynone compound is of Formula VI:

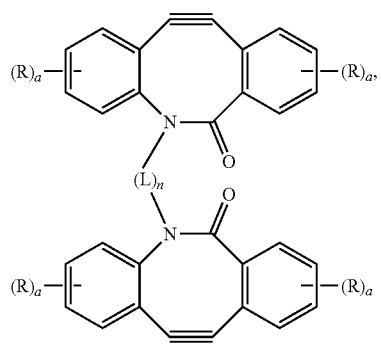

Formula VI wherein

L is a divalent moiety selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;

n is a number selected from zero to 40;

each R is independently selected from alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, thioketo, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl; and each a is a number selected from zero to four.

In some embodiments, the subject azacycloalkynone compound includes one or more substituents, divalent moieties L or a Y group that provides for increased solubility under physiological conditions (e.g., an aqueous buffer). For example, the subject azacycloalkynone compound may provide for a 10% or more increase in solubility over BARAC, such as a 20% or more, 50% or more, or 100%, or more than 100%, increase in solubility. For example, the subject azacycloalkynone compound may provide for a 2-fold or more increase in solubility over BARAC, such as a 5-fold or more, 10-fold or more, or 100-fold, or more than 100-fold, increase in solubility.

In some embodiments, a subject azacycloalkynone compound has the structure of Compound 15, as shown below:

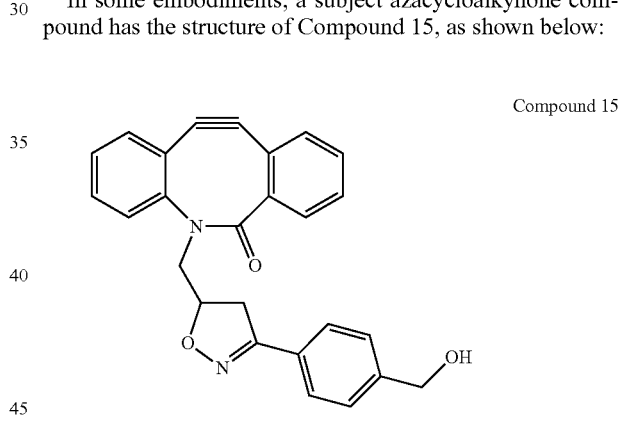

Compound 15

Compound 15: BARAC.

In some embodiments, a subject azacycloalkynone compound has the structure of Compound 16, as shown below:

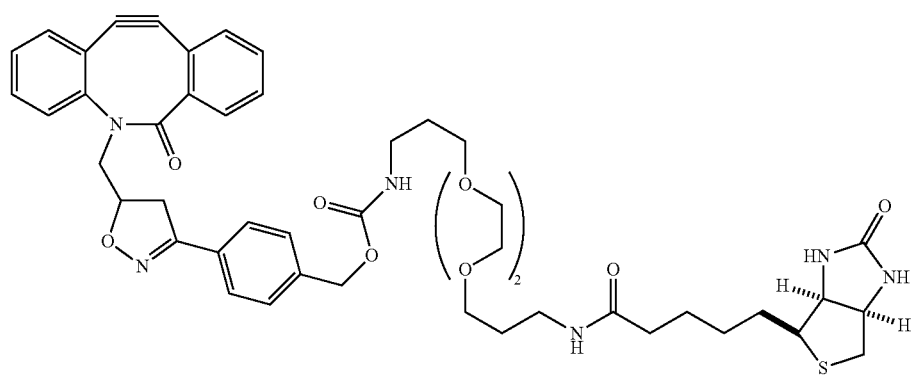

Compound 16

Compound 16: BARAC-biotin.

In some embodiments, a subject azacycloalkynone compound has the structure of Compound 17, as shown below:

Compound 17

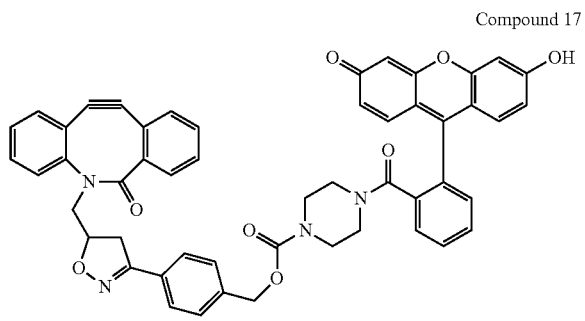 [SMILES: O=C(OCc1ccc(C2=NOC(CN3C(=O)c4ccccc4C#Cc4ccccc43)C2)cc1)N1CCN(C(=O)c2ccccc2-c2c3ccc(=O)cc-3oc3cc(O)ccc23)CC1]

Compound 17: BARAC-Fluor.

In some embodiments, a subject azacycloalkynone compound has the structure of Compound 21, as shown below:

Compound 21

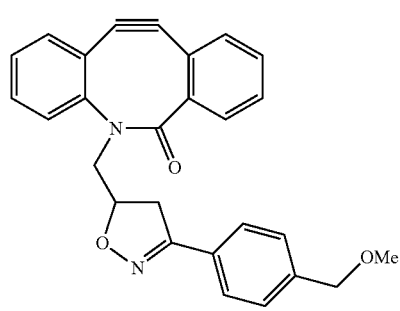

In some embodiments, a subject azacycloalkynone compound has the structure of Compound 22, as shown below:

Compound 22

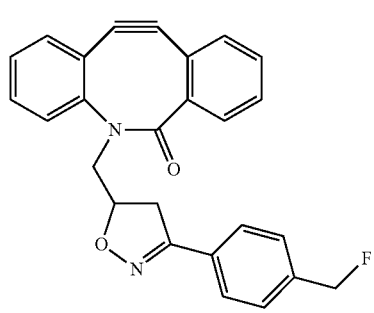

In some embodiments, a subject azacycloalkynone compound has the structure of Compound 23, as shown below:

Compound 23

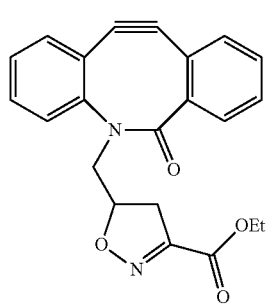

In some embodiments, a subject azacycloalkynone compound has the structure of Compound 24, as shown below, wherein R is selected from hydrogen, alkyl, sulfate, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclyl, substituted heterocyclyl, sulfonyl, sulfonamide, sulfonyl ester, amino, and substituted amino:

Compound 24

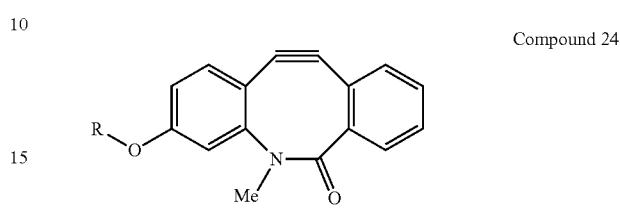

In some embodiments, a subject azacycloalkynone compound has the structure of Compound 25, as shown below:

Compound 25

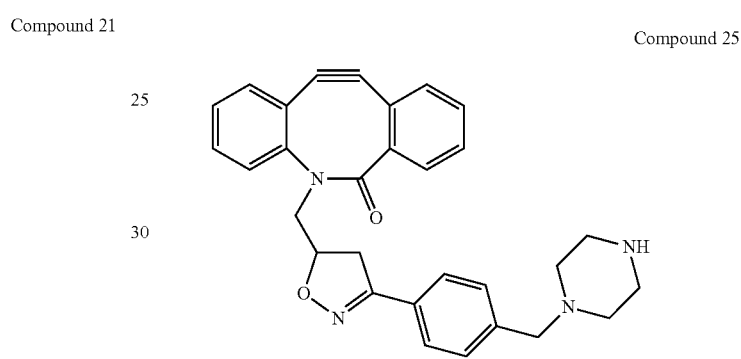

In some embodiments, a subject azacycloalkynone compound has the structure of Compound 26, as shown below:

Compound 26

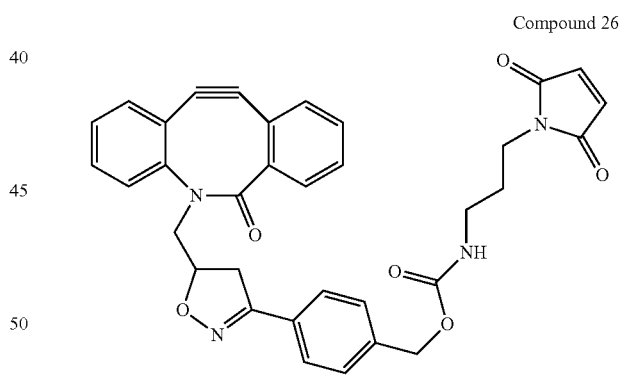

In some embodiments, a subject azacycloalkynone compound has the structure of Compound 27, as shown below:

Compound 27

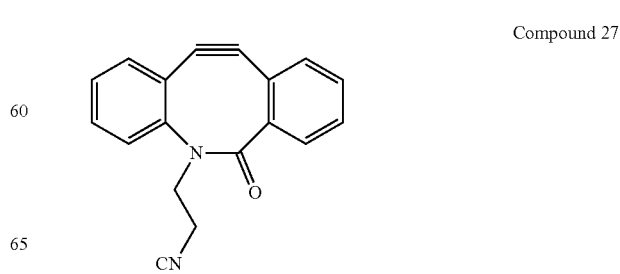

In some embodiments, a subject azacycloalkynone compound has the structure of Compound 28, as shown below:

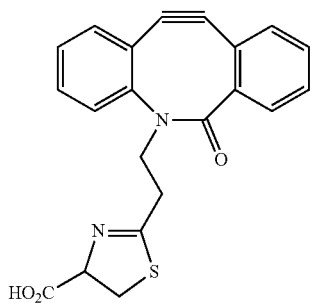

Compound 28

In some embodiments, a subject azacycloalkynone compound has the structure of Compound 119, as shown below:

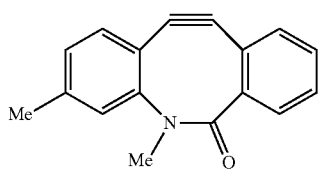 [SMILES: Cc1ccc2c(c1)N(C)C(=O)c1ccccc1C#C2]

In some embodiments, a subject azacycloalkynone compound has the structure of Compound 120, as shown below:

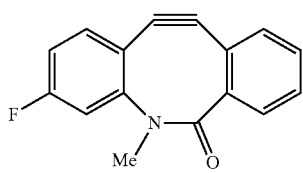 [SMILES: CN1C(=O)c2ccccc2C#Cc2ccc(F)cc21]

In some embodiments, a subject azacycloalkynone compound has the structure of Compound 123, as shown below:

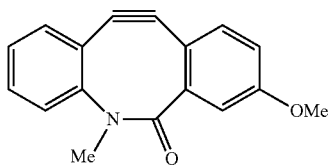 [SMILES: COc1ccc2c(c1)C(=O)N(C)c1ccccc1C#C2]

In some embodiments, a subject azacycloalkynone compound has the structure of Compound 124, as shown below:

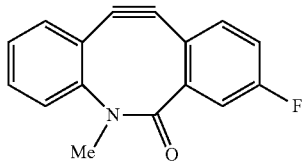 [SMILES: CN1C(=O)c2cc(F)ccc2C#Cc2ccccc21]

In some embodiments, a subject azacycloalkynone compound has the structure of Compound 41, as shown below:

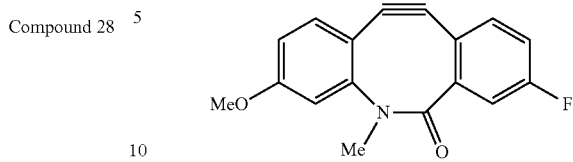

In some embodiments, a subject azacycloalkynone compound has the structure of Compound 44, as shown below:

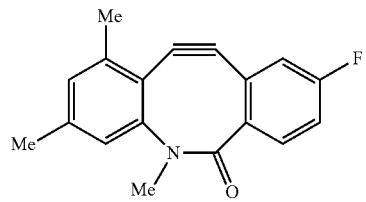 [SMILES: Cc1cc(C)c2c(c1)N(C)C(=O)c1ccc(F)cc1C#C2]

A subject azacycloalkynone compound can be coupled to a molecule of interest using any suitable method and chemistry. For example, coupling can be achieved using a metal-catalyzed cross-coupling or metal-halogen exchange/nucleophilic attack method, as illustrated in the following scheme:

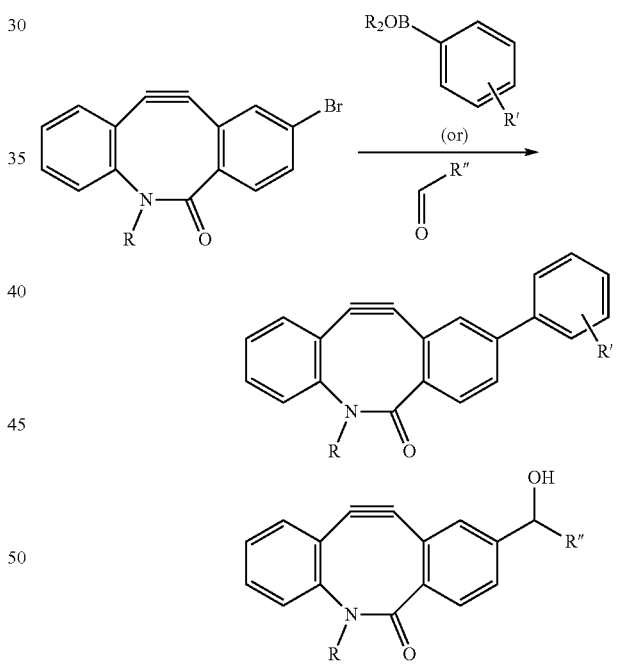

where R' and R" are molecules of interest, and each R is independently an alkyl, a substituted alkyl, an aryl or a substituted aryl, and where optionally the R groups of the boronic ester may be cyclically linked.

Molecules of Interest

In some embodiments, Y is a molecule of interest. Suitable molecules of interest include, but are not limited to, a detectable label; a toxin (including cytotoxins); a linker; a peptide; a drug; a member of a specific binding pair; an epitope tag; a strained azacycloalkynone group; a cycloalkyne, a phosphine, a ketone, a fluorophore, a isotopically labeled tag, and the like. Where Y is a molecule of interest other than a linker, the molecule of interest is attached directly to an R group, as noted above, or is attached through a linker.

Where Y is a molecule of interest, the modified cycloalkyne may include a molecule desired for delivery and conjugation to the azido-target substrate (azide-containing target molecule), which target substrate may be displayed on the cell surface, may reside within the cell membrane, or may be intracellular. Molecules that may be desirable for delivery include, but are not necessarily limited to, detectable labels (e.g., spin labels, fluorescence resonance energy transfer (FRET)-type dyes, e.g., for studying structure of biomolecules in vivo), small molecule drugs, cytotoxic molecules (e.g., drugs), ligands for binding by a target receptor (e.g., to facilitate viral attachment, attachment of a targeting protein present on a liposome, etc.), tags to aid in purification by, for example, affinity chromatography (e.g., attachment of a FLAG epitope), molecules to facilitate selective attachment of the polypeptide to a surface, an enzyme inhibitor (e.g., for use in activity-based protein profiling), and the like. Specific, non-limiting examples are provided below.

Detectable Labels

The compositions and methods can be used to deliver a detectable label to a target molecule having an azide. In some embodiments, a modified cycloalkyne includes a detectable label, covalently bound to the modified cycloalkyne either directly or through a linker.

Exemplary detectable labels include, but are not necessarily limited to, fluorescent molecules (e.g., autofluorescent molecules, molecules that fluoresce upon contact with a reagent, etc.), radioactive labels (e.g., $^{111}$In, $^{125}$I, $^{131}$I, $^{212}$B, $^{90}$Y, $^{186}$Rh, $^{18}$F and the like); biotin (e.g., to be detected through reaction of biotin and avidin); fluorescent tags; imaging reagents (e.g., those described in U.S. Pat. No. 4,741,900 and U.S. Pat. No. 5,326,856, the disclosures of which are incorporated herein by reference in their entirety), and the like. Detectable labels also include peptides or polypeptides that can be detected by antibody binding, e.g., by binding of a detectably labeled antibody or by detection of bound antibody through a sandwich-type assay. Also suitable for use are quantum dots (e.g., detectably labeled semiconductor nanocrystals, such as fluorescently labeled quantum dots, antibody-conjugated quantum dots, and the like). See, e.g., Dubertret et al. (2002) *Science* 298:759-1762; Chan et al. (1998) *Science* 281:2016-2018; U.S. Pat. No. 6,855,551; Bruchez et al. (1998) *Science* 281:2013-2016, the disclosures of which are incorporated herein by reference in their entirety.

In certain embodiments, the subject compositions do not include a naturally occurring or synthetic isotope, a naturally occurring or synthetic radioisotope, or the like. For example, certain embodiments of the subject compositions do not include isotopes or radioisotopes, such as, but not limited to, deuterium, tritium, carbon-13, carbon-14, nitrogen-15, oxygen-18, silicon-29, chlorine-36, and the like. For instance, in certain instances, the subject compositions are not substituted with isotopes or radioisotopes due to the natural abundance of the isotopes or radioisotopes. In some cases, the subject compositions are not deuterated, e.g., the subject compositions do not include a detectable label, such as deuterium, including naturally occurring or synthetic deuterium. For example, in certain instances, hydrogen in the subject compositions is not substituted with deuterium due to the natural abundance of deuterium.

Suitable fluorescent molecules (fluorophores) include, but are not limited to, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethyl-benzimidazoylcarbocyanine iodide), tetrabromorhodamine 123, rhodamine 6G, TMRM (tetramethylrhodamine-, methyl ester), TMRE (tetramethylrhodamine, ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5''-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amino-1-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl)aminonaphthalene-1-sulfonic acid (EDANS),4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, and fluorescent europium and terbium complexes; and the like. Fluorophores of interest are further described in WO 01/42505 and WO 01/86001, the disclosures of which are incorporated herein by reference in their entirety.

Suitable fluorescent proteins and chromogenic proteins include, but are not limited to, a green fluorescent protein (GFP), including, but not limited to, a GFP derived from *Aequoria victoria* or a derivative thereof, e.g., a "humanized"

derivative such as Enhanced GFP, which is available commercially, e.g., from Clontech, Inc.; a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519, the disclosures of which are incorporated herein by reference in their entirety; "humanized" recombinant GFP (hrGFP) (Stratagene); any of a variety of fluorescent and colored proteins from Anthozoan species, as described in, e.g., Matz et al. (1999) *Nature Biotechnol.* 17:969-973, the disclosure of which is incorporated herein by reference in its entirety; and the like.

Suitable epitope tags include, but are not limited to, hemagglutinin (HA; e.g., CYPYDVPDYA; SEQ ID NO:1), FLAG (e.g., DYKDDDDK; SEQ ID NO:2), FLAG-C (e.g., DYKDDDDKC; SEQ ID NO:3, c-myc (e.g., CEQKLISEEDL; SEQ ID NO:4), a metal ion affinity tag such as a polyhistidine tag (e.g., $His_6$), and the like.

Suitable imaging agents include positive contrast agents and negative contrast agents. Suitable positive contrast agents include, but are not limited to, gadolinium tetraazacyclododecanetetraacetic acid (Gd-DOTA); Gadolinium-diethylenetriaminepentaacetic acid (Gd-DTPA); Gadolinium-1,4,7-tris (carbonylmethyl)-10-(2'-hydroxypropyl)-1,4,7,10-tetraazacyclododecane (Gd-HP-DO3A); Manganese(II)-dipyridoxal diphosphate (Mn-DPDP); Gd-diethylenetriaminepentaacetate-bis(methylamide) (Gd-DTPA-BMA); and the like. Suitable negative contrast agents include, but are not limited to, a superparamagnetic iron oxide (SPIO) imaging agent; and a perfluorocarbon, where suitable perfluorocarbons include, but are not limited to, fluoroheptanes, fluorocycloheptanes, fluoromethylcycloheptanes, fluorohexanes, fluorocyclohexanes, fluoropentanes, fluorocyclopentanes, fluoromethylcyclopentanes, fluorodimethylcyclopentanes, fluoromethylcyclobutanes, fluorodimethylcyclobutanes, fluorotrimethylcyclobutanes, fluorobutanes, fluorocyclobutanse, fluoropropanes, fluoroethers, fluoropolyethers, fluorotriethylamines, perfluorohexanes, perfluoropentanes, perfluorobutanes, perfluoropropanes, sulfur hexafluoride, and the like.

Specific Binding Partners

In some embodiments, a subject modified cycloalkyne includes a member of a pair of binding partners. A member of a pair of binding partners is referred to herein as a "specific binding partner."

Suitable specific binding partners include, but are not limited to, a member of a receptor/ligand pair; a member of an antibody/antigen pair; a member of a lectin/carbohydrate pair; a member of an enzyme/substrate pair; biotin/avidin; biotin/streptavidin; digoxin/antidigoxin; and the like. Suitable specific binding partners include, but are not limited to a receptor ligand; a receptor for a ligand; a ligand-binding portion of a receptor; an antibody; an antigen-binding fragment of an antibody; an antigen; a hapten; a lectin; a lectin-binding carbohydrate; an enzyme substrate; an irreversible inhibitor of an enzyme (e.g., an irreversible inhibitor that binds a substrate binding site of an enzyme, e.g., a "suicide" substrate); and the like.

Suitable ligand members of receptor/ligand pairs include, but are not limited to, neurotransmitters such as opioid compounds, acetylcholine, and the like; viral proteins that bind to a cell surface receptor, e.g., human immunodeficiency virus gp120, and the like; hormones; and the like.

Suitable antigen-binding antibody fragments include $F(ab')_2$, $F(ab)_2$, Fab', Fab, Fv, scFv, and Fd fragments, single-chain antibodies, and fusion proteins comprising an antigen-binding portion of an antibody and a non-antibody protein (e.g., an antigen-binding fragment of an antibody fused to an immunoglobulin constant region).

Suitable haptens include, but are not limited to, (4-hydroxy-3-nitrophenyl)acetyl; diethylenetriaminepentaacetic acid (DTPA) or one of its metal complexes; paranitrophenyl; biotin; fluorescein isothiocyanate; and the like.

Drugs

Suitable drugs that can be attached to a modified cycloalkyne moiety include, but are not limited to, cytotoxic compounds (e.g., cancer chemotherapeutic compounds); antiviral compounds; biological response modifiers (e.g., hormones, chemokines, cytokines, interleukins, etc.); microtubule affecting agents; hormone modulators; steroidal compounds; and the like.

Suitable cancer chemotherapeutic compounds include, but are not limited to, non-peptidic (e.g., non-proteinaceous) compounds that reduce proliferation of cancer cells; peptidic compounds that reduce proliferation of cancer cells; antimetabolite agents; cytotoxic agents; and cytostatic agents. Non-limiting examples of chemotherapeutic agents include alkylating agents, nitrosoureas, antimetabolites, antitumor antibiotics, plant (vinca) alkaloids, and steroid hormones.

Suitable agents that act to reduce cellular proliferation include, but are not limited to, alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Suitable antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable anti-proliferative natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other suitable anti-proliferative cytotoxic agents are navelbene, CPT-11, anastrazole, letrazole, capecitabine, reloxafine, cyclophosphamide, ifosamide, and droloxafine.

Suitable microtubule affecting agents that have antiproliferative activity include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Suitable hormone modulators and steroids (including synthetic analogs) include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), Zoladex®, and the like. Estrogens stimulate proliferation and differentiation, therefore compounds that bind to the estrogen receptor are used to block this activity. Corticosteroids may inhibit T cell proliferation.

Other suitable chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Taxanes are also suitable for attachment to a cycloalkyne moiety. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267, the disclosures of which are incorporated herein by reference in their entirety), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but are not limited to, galactose and mannose derivatives described in International Patent Application No. WO 99/18113, the disclosure of which is incorporated herein by reference in its entirety; piperazino and other derivatives described in WO 99/14209, the disclosure of which is incorporated herein by reference in its entirety; taxane derivatives described in WO 99/09021, WO 98/22451, and U.S. Pat. No. 5,869,680, the disclosures of which are incorporated herein by reference in their entirety; 6-thio derivatives described in WO 98/28288, the disclosure of which is incorporated herein by reference in its entirety; sulfenamide derivatives described in U.S. Pat. No. 5,821,263, the disclosure of which is incorporated herein by reference in its entirety; and taxol derivative described in U.S. Pat. No. 5,415,869, the disclosure of which is incorporated herein by reference in its entirety. The term "taxane" further includes prodrugs of paclitaxel including, but not limited to, those described in WO 98/58927; WO 98/13059; and U.S. Pat. No. 5,824,701, the disclosures of which are incorporated herein by reference in their entirety.

Biological response modifiers that are suitable for attachment to a cycloalkyne moiety include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ (8) colony-stimulating factors; (9) inhibitors of angiogenesis; and the like.

Linkers

Suitable linkers include, but are not limited to, a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, a nitro, a peptide linker, and the like.

Exemplary peptide linkers for use in linking a molecule of interest to a modified cycloalkyne will in some embodiments have a combination of glycine, alanine, proline and methionine residues. In some embodiments, a peptide linker comprises multiple serine residues, e.g., from 50% to 75%, or from 75% to 100% of the amino acids in the linker are serine residues. In some embodiments, a peptide linker comprises multiple glycine residues, e.g., from 50% to 75%, or from 75% to 100% of the amino acids in the linker are glycine residues. Any flexible linker, generally having a length of from 6 amino acids to 40 amino acids is suitable for use. Linkers may have virtually any sequence that results in a generally flexible peptide.

Exemplary flexible linkers include glycine polymers (G)n, glycine-serine polymers (including, for example, (GS)n, GSGGSn (SEQ ID NO: 5) and GGGSn (SEQ ID NO: 6), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, Rev. Computational Chem. 11173-142 (1992)). Exemplary flexible linkers include, but are not limited GGSG (SEQ ID NO: 7), GGSGG (SEQ ID NO: 8), GSGSG (SEQ ID NO: 9), GSGGG (SEQ ID NO: 10), GGGSG (SEQ ID NO: 11), GSSSG (SEQ ID NO: 12), and the like.

Compositions

Embodiments of the present disclosure further include compositions, including pharmaceutical compositions, having a subject modified cycloalkyne compound. In certain instances, a subject composition includes a subject modified cycloalkyne compound and at least one additional compound. Suitable additional compounds include, but are not limited to: a salt, such as a magnesium salt, a sodium salt, etc., e.g., NaCl, MgCl, KC, MgSO$_4$, etc.; a buffering agent, e.g., a Tris buffer, N-(2-hydroxyethyl)piperazine-N'-(2-ethanesulfonic acid) (HEPES), 2-(N-morpholino)ethanesulfonic acid (MES), 2-(N-morpholino)ethanesulfonic acid sodium salt (MES), 3-(N-morpholino)propanesulfonic acid (MOPS), N-tris[hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

In some embodiments, a subject composition includes a subject modified cycloalkyne compound; and a pharmaceutically acceptable excipient. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20$^{th}$ edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Methods of Modifying a Target Biomolecule

Aspects of the present disclosure include methods for labeling a target molecule that includes an azide. The methods may involve reacting an azide in an azide-containing target molecule with a modified cycloalkyne. The modified cycloalkyne may have a structure as described above. In certain embodiments, a subject method for labeling a cellular component involves: (a) introducing an azide moiety into a cellular component, thereby generating an azide-modified cellular component; and (b) contacting a cell having the azide-modified cellular component with a reactive partner that includes a modified cycloalkyne. In some instances, the contacting is under physiological conditions. The contacting step results in reaction between the azide group of azide-modified cellular component and the cycloalkyne of the reactive partner, thereby synthetically and covalently modifying the cellular component to produce a covalently modified cellular component. In some embodiments, the method is carried out on living cells in vitro. In certain instances, the method is carried out on living cells ex vivo. For example, the method may be carried out on living cells in vivo.

In certain embodiments, the chemoselective ligation is designed for use in fully aqueous, physiological conditions and involves production of a stable, final product having a fused azide/cycloalkyne ring. For example, the chemoselective ligation may involve reacting a first reactant having a strained cycloalkyne moiety with a second reactant having an azide, such that a covalent bond is formed between the first and second reactants by reaction of the strained cycloalkyne moiety with the azide group.

First Reactant

In certain embodiments, a first reactant includes a strained cycloalkyne moiety that provides the energy for the reaction between the first and second reactants. The first reactant may be a modified cycloalkyne compound of any of Formulas I-V, as described above.

Exemplary reactive groups include, but are not necessarily limited to, carboxyl, amine, (e.g., alkyl amine (e.g., lower alkyl amine), aryl amine), ester (e.g., alkyl ester (e.g., lower alkyl ester, benzyl ester), aryl ester, substituted aryl ester), thioester, sulfonyl halide, alcohol, alkoxide, thiol, succinimidyl ester, isothiocyanate, iodoacetamide, maleimide, hydrazine, hydrazide, carbonyl, halogen, cyano, diazo, azide, guanidine, sulfone, epoxide, diazirine, alkene, alkyne, phosphine, silane, alkylsulfonic acid and the like. In some embodiments, a reactive group is selected from a carboxyl, an amine, an ester, a thioester, a sulfonyl halide, an alcohol, an alkoxide, a thiol, a succinimidyl ester, an isothiocyanate, an iodoacetamide, a maleimide, a hydrazine, a hydrazide, a carbonyl, a halogen, a cyano, a diazo, an azide, a guanidine, a sulfone, an epoxide, a diazirine, an alkene, an alkyne, a phosphine, a silane, and an alkylsulfonic acid. Exemplary molecules of interest further include dyes (e.g., fluorescein or modified fluorescein, and the like), toxins (including cytotoxins), linkers, peptides, and the like.

The molecule of interest may be reacted directly with the reactive group or through a linker. Exemplary molecules of interest include, but are not necessarily limited to, a detectable label; a toxin (including cytotoxins); a linker; a peptide; a drug; a member of a specific binding pair; an epitope tag; and the like. Such molecules of interest are described in more detail above.

In some embodiments, Y is a reactive group, where suitable reactive groups include, but are not limited to, carboxyl, amine, (e.g., alkyl amine (e.g., lower alkyl amine), aryl amine), ester (e.g., alkyl ester (e.g., lower alkyl ester, benzyl ester), aryl ester, substituted aryl ester), thioester, sulfonyl halide, alcohol, alkoxide, thiol, succinimidyl ester, isothiocyanate, iodoacetamide, maleimide, hydrazine, hydrazide, carbonyl, halogen, cyano, diazo, azide, guanidine, sulfone, epoxide, diazirine, alkene, alkyne, phosphine, silane, alkylsulfonic acid and the like. In some embodiments, Y is a reactive group selected from a carboxyl, an amine, an ester, a thioester, a sulfonyl halide, an alcohol, an alkoxide, a thiol, a succinimidyl ester, an isothiocyanate, an iodoacetamide, a maleimide, a hydrazine, a hydrazide, a carbonyl, a halogen, a cyano, a diazo, an azide, a guanidine, a sulfone, an epoxide, a diazirine, an alkene, an alkyne, a phosphine, a silane, and an alkylsulfonic acid.

In some embodiments, the cycloalkyne is a cyclooctyne. In some embodiments, the cycloalkyne is an azacycloalkynone.

Second Reactant

In certain embodiments, the second reactant is a compound that includes an azide such that a covalent bond is formed between the first and second reactants by reaction of the cycloalkyne moiety with the azide group. In some cases, the second reactant is of the formula:

$$R_2-N_3$$

where $R_2$ is a target molecule, e.g., a biomolecule or other target molecule as described in more detail below.

Target Molecules

Molecules having an azide and suitable for use in embodiments of the present disclosure, as well as methods for producing azide-containing molecules suitable for use in embodiments of the present disclosure, are well known in the art. Target molecules of interest as the second reactant include, but are not necessarily limited to, amino acids and amino acid residues, polypeptides (including peptides and proteins), sugars or sugar residues, and the like, which contain or are modified to contain one or more azide moieties.

The target molecules can be naturally occurring, or may be synthetically or recombinantly produced, and may be isolated, substantially purified, or present within the native milieu of the unmodified molecule upon which the azide-containing target molecule is based (e.g., on a cell surface or within a cell, including within a host animal, e.g., a mammalian animal, such as a murine host (e.g., rat, mouse), hamster, canine, feline, bovine, swine, and the like). In some embodiments, the target molecule is present in vitro in a cell-free reaction. In certain instances, the target molecule is present in a cell and/or displayed on the surface of a cell. In some cases, the target molecule is in a living cell; on the surface of a living cell; in a living organism, e.g., in a living multicellular organism. Suitable living cells may include cells that are part of a living multicellular organism; cells isolated from a multicellular organism; immortalized cell lines; and the like.

Where the target molecule is a polypeptide, the polypeptide may include D-amino acids, L-amino acids, or both, and may be further modified, either naturally, synthetically, or recombinantly, to include other moieties. For example, the target polypeptide may be a lipoprotein, a glycoprotein, or other such modified protein.

In certain embodiments, the target molecule useful as the second reactant includes at least one azide for reaction with a modified cycloalkyne according to embodiments of the present disclosure, but may include 2 or more, 3 or more, 5 or more, 10 or more azides. The number of azides that may be present in a target molecule will vary according to the intended application of the final product of the reaction, the nature of the target molecule itself, and other considerations which will be readily apparent to the ordinarily skilled artisan in practicing embodiments of the disclosure as disclosed herein.

Embodiments of the present disclosure are useful in modification of a target molecule in vivo. In certain embodiments, the target substrate is modified to include an azide group at the point at which linkage to the modified cycloalkyne reactant is desired. For example, where the target substrate is a polypeptide, the polypeptide may be modified to contain an N-terminal azide. Where the target substrate is a glycoprotein, a sugar residue of the glycoprotein can be modified to contain an azide. A target molecule that is unmodified with an azide, but that is to be modified with an azide, is referred to herein as a "target substrate." A target molecule that is modified with an azide is referred to herein as "an azide-modified target molecule" or "an azide-containing target molecule."

Azide Modification of a Target Molecule

The target substrate can be generated in vitro and then introduced into the cell using any of a variety of methods well known in the art (e.g., microinjection, liposome or lipofectin-mediated delivery, electroporation, etc.), which methods will vary according to the nature of the substrate to be targeted for modification and can be readily and appropriately selected by the ordinarily skilled artisan. The final target substrate can also be generated in vivo by exploiting a host cell's natural biosynthetic machinery. For example, the cell can be provided with a biocompatible azide-derivative of a substrate for synthesis of the desired target molecule, which substrate is processed by the cell to provide an azide-derivative of the desired final target substrate. For example, where the target substrate is a cell surface glycoprotein, the cell can be provided with an azide derivative of a sugar residue found within the glycoprotein, which is subsequently processed by the cell through natural biosynthetic processes to produce a modified glycoprotein having at least one modified sugar moiety comprising an accessible azide group.

An azide moiety that can react with a subject compound can be incorporated into any of a variety of molecules, including biomolecules. Methods for incorporating an azide moiety that is available for reaction with a subject compound are known in the art. See, e.g., Sletten et al. (2009) *Angew. Chem. Int. Ed.* 48:6974; and Chang et al. (2010) *Proc. Natl. Acad. Sci. USA* 107:1821. An azide moiety that is available for reaction with a subject compound can be incorporated into a sugar moiety, for example. A sugar moiety can be present in a glycan, in a lipopolysaccharide, in a glycoprotein, etc. An azide moiety that is available for reaction with a subject compound can be incorporated into an amino acid, where the amino acid can be present in a polypeptide, a glycoprotein, a proteoglycan, etc. An azide moiety that is available for reaction with a subject compound can be incorporated into a fatty acid, where the fatty acid can be present in a lipid, a lipopolysaccharide, a glycolipoprotein, a lipoprotein, etc. See, e.g., Yap et al. (2010) *J Lipid Res.* PMID: 20028662; and Martin et al. (2008) *FASEB J.* 22:797.

The target substrate can also be produced in vivo using other methods. For example, unnatural amino acids having azides can be incorporated into recombinant polypeptides expressed in *E. coli* (see, e.g., Kiick et al. (2000) *Tetrahedron* 56:9487, the disclosure of which is incorporated herein by reference in its entirety). Such recombinantly produced polypeptides can be selectively reacted with a modified cycloalkyne reagent according to embodiments of the present disclosure.

For example, an azide group can be incorporated into the target molecule by providing a cell (e.g., a eukaryotic cell that glycosylates biopolymers such as proteins) with a synthetic building block for the desired biopolymer target substrate. For instance, the cell can be provided with a sugar molecule having an azide group to provide for incorporation of the azide group in a glycoprotein. In some embodiments, the glycoprotein is expressed on the cell surface. Alternatively, the azide group can be incorporated into an amino acid, which is subsequently incorporated into a peptide or polypeptide synthesized by the cell. Several methods are available for incorporating unnatural building blocks into biopolymers; one need not be restricted to cell surface oligosaccharides as target molecules. See, e.g., vanHest et al. (1998) *FEBS Lett.* 428:68; and Nowak et al. (1995) *Science* 268:439, the disclosures of which are incorporated herein by reference in their entirety. **

In certain embodiments, the target molecule is a carbohydrate-containing molecule (e.g., a glycoprotein; a polysaccharide; etc.), and an azide group is introduced into the target molecule using a synthetic substrate. In some cases, the synthetic substrate is an azide derivative of a sugar utilized in production of a glycosylated molecule. In certain instances, the synthetic substrate is an azide derivative of a sugar utilized in production of a cell surface molecule, e.g., in the glycoprotein biosynthetic pathway. For example, the host cell can be provided with a synthetic sialic acid azido-derivative, which can be incorporated into the pathway for sialic acid biosynthesis, eventually resulting in the incorporation of the synthetic sugar residue in glycoproteins. In some embodiments, the glycoproteins are displayed on the cell surface.

For example, the synthetic substrate may be an azido derivative of mannosamine of the formula:

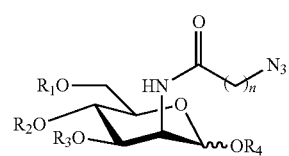

where n is from 1 to 6, generally from 1 to 4, more usually 1 to 2, and $R_1$, $R_2$, $R_3$, and $R_4$ are independently hydrogen or acetyl. In some embodiments, the substrate is N-azidoacetyl-mannosamine (n=1) or an acetylated derivative thereof, or N-azidopropanoylmannosamine (n=2) or an acetylated form thereof.

In some embodiments, the synthetic substrate is an azido sugar derivative of a formula of, for example:

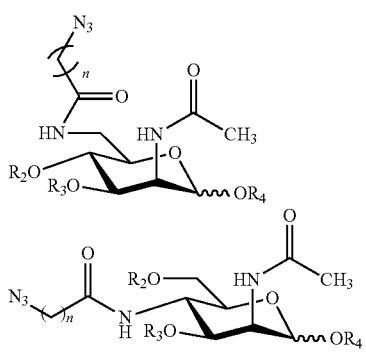

either of which can be incorporated into the sialic acid biosynthesis pathway, and where n is from 1 to 6, such as from 1 to 4, including from 1 to 2, and $R_2$, $R_3$, and $R_4$ are each independently hydrogen or acetyl.

In certain embodiments, the synthetic substrate is an azido sugar derivative of a formula of, for example:

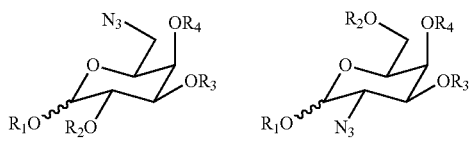

where $R_1$, $R_2$, $R_3$, and $R_4$ are each independently hydrogen or acetyl, and where the synthetic substrate is incorporated into biosynthetic pathways involving fucose.

In certain embodiments, the synthetic substrate is an azido sugar derivative of a formula of, for example:

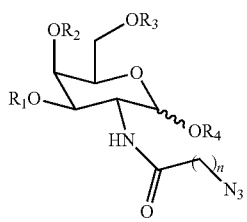

where n is from 1 to 6, such as from 1 to 4, including from 1 to 2, and $R_1$, $R_2$, $R_3$, and $R_4$ are each independently hydrogen or acetyl, and which is incorporated into biosynthetic pathways involving galactose.

Cell Surface Modification

In some embodiments, a subject method is used to modify the surface of a cell. Aspects of the present disclosure include a method of modifying the surface of cell in vitro or in vivo. In certain cases, the method involves reacting an azide group in a target molecule that includes an azide group with a modified cycloalkyne to provide for chemoselective ligation at the cell surface. In some instances, the method includes modifying a target molecule on a cell surface with an azide group; and reacting the azide group in the target molecule with a modified cycloalkyne. For example, as described above, an azido sugar can be provided to a living cell, which azido sugar is incorporated into a glycoprotein that is displayed on the cell surface.

Modification of an Azide-Modified Target Molecule with Detectable Labels, Drugs, and Other Molecules Embodiments of the present disclosure include attachment of a molecule of interest, e.g., a functional molecule, to an azide-modified target molecule. The methods may involve reacting an azide-modified target molecule with a subject modified cycloalkyne, where the modified cycloalkyne includes a molecule of interest, as described above. As described above, molecules of interest include, but are not limited to, a detectable label; a toxin (including cytotoxins); a linker; a peptide; a drug; a member of a specific binding pair; an epitope tag; and the like.

Attachment of Target Molecules to a Support

The modified cycloalkyne can also include one or more hydrocarbon linkers (e.g., an alkyl group or derivative thereof such as an alkyl ester) conjugated to a moiety providing for attachment to a solid substrate (e.g., to facilitate assays), or to a moiety providing for easy separation (e.g., a hapten recognized by an antibody bound to a magnetic bead). In certain embodiments, the methods are used to provide for attachment of a protein (or other molecule that contains or can be modified to contain an azide) to a chip in a defined orientation. For example, a polypeptide having an azide at a selected site (e.g., at or near the N-terminus) can be generated, and the subject methods and compositions used to deliver a tag or other moiety to the azide of the polypeptide. The tag or other moiety can then be used as the attachment site for affixing the polypeptide to a support (e.g., solid or semi-solid support, particular a support suitable for use as a microchip in high-throughput assays).

Attachment of Molecules for Delivery to a Target Site

The modified cycloalkyne will in some embodiments include a small molecule drug, toxin, or other molecule for delivery to a cell. The small molecule drug, toxin, or other molecule will in some embodiments provide for a pharmacological activity. The small molecule drug, toxin, or other molecule will in some embodiments serve as a target for delivery of other molecules.

Small molecule drugs may be small organic or inorganic compounds having a molecular weight of more than 50 and less than about 2,500 daltons. Small molecule drugs may include functional groups necessary for structural interaction with proteins, particularly hydrogen bonding, and may include at least an amine, carbonyl, hydroxyl or carboxyl group. In some cases, the small molecule drugs contain at least two functional chemical groups. The drugs may include cyclical carbon or heterocyclic structures and/or aromatic or polyaromatic structures substituted with one or more of the above functional groups. Small molecule drugs may also be found among biomolecules including, but not limited to, peptides, saccharides, fatty acids, steroids, purines, pyrimidines, derivatives, structural analogs or combinations thereof, and the like.

In certain embodiments, a subject modified cycloalkyne includes one of a pair of binding partners (e.g., a ligand; a ligand-binding portion of a receptor; an antibody; an antigen-binding fragment of an antibody; an antigen; a hapten; a lectin; a lectin-binding carbohydrate; etc.). For example, the modified cycloalkyne can include a polypeptide that serves as a viral receptor and, upon binding with a viral envelope protein or viral capsid protein, facilitates attachment of virus to the cell surface on which the modified cycloalkyne is displayed. Alternatively, the modified cycloalkyne may include an antigen that is specifically bound by an antibody (e.g., monoclonal antibody), to facilitate detection and/or separation of host cells displaying the antigen on the cell surface.

For example, the modified cycloalkyne may include a ligand binding portion of a receptor, or a receptor-binding portion of a ligand.

Utility

Embodiments of the subject modified cycloalkyne compounds, and subject modification methods, are useful in a variety of applications, including research applications, diagnostic applications, and synthetic applications (e.g., materials applications).

Research Applications

In some embodiments, the subject modified cycloalkyne compounds, and subject modification methods, are useful in research applications. Applications of interest include research applications, e.g., exploring functional and physical characteristics of a receptor; proteomics; metabolomics; and the like. Research applications also include drug discovery or other screening applications.

Proteomics aims to detect, identify, and quantify proteins to obtain biologically relevant information. Metabolomics is the detection, identification, and quantification of metabolites and other small molecules such as lipids and carbohydrates. Fiehn (2001) *Comparative and Functional Genomics* 2:155-168; and U.S. Pat. No. 6,873,914.

Drug discovery applications include, but are not limited to, identifying agents that inhibit cancer cell viability and/or growth. In some embodiments, provided are methods of identifying an agent that inhibits cancer cell viability and/or growth. The methods generally involve modifying a component of the cell to include a first reactive partner having an azide; contacting the cell, in the presence of a test agent, with a second reactive partner having a modified cycloalkyne, the contacting being under physiological conditions; where the contacting results in reaction between the azide group of the first reactive partner and the cycloalkyne of the second reactive partner, thereby synthetically and covalently modifying the cellular component; and determining the effect, if any, of the test agent on the level of modification of the cell with the second reactive partner.

Where the cancer cell is one that produces a higher amount of a carbohydrate than a normal (non-cancerous) cell of the same cell type, the method may include identifying an agent that reduces growth and/or viability of the cancerous cell.

Diagnostic and Therapeutic Applications

Applications of interest also include diagnostic applications, e.g., for detection of cancer; and the like, where a subject modified cycloalkyne having a detectable label is used to label an azide-modified target molecule, e.g., an azide-labeled target molecule present on a cancer cell. Applications of interest also include therapeutic applications, where a drug or other therapeutic agent is delivered to an azide-modified target molecule, using a subject modified cycloalkyne that includes a covalently linked drug or other therapeutic agent.

In some embodiments, the subject compounds and methods are used for in vivo imaging, e.g., to determine the metabolic or other state of a cell in an organism, e.g., an individual. For example, a subject method can be applied to in vivo imaging of cancer cells in an individual (e.g., a mammal, including rodents, lagomorphs, felines, canines, equines, bovines, ovines, caprines, non-human primates, humans, etc.).

One exemplary, non-limiting application of a subject azide-alkyne cycloaddition is in the detection of metabolic change in cells that occur as they alter their phenotype. For example, altered glycosylation patterns may be indicative of the tumor phenotype, including both the under- and over-expression of naturally-occurring glycans as well as the presentation of glycans normally restricted to expression during embryonic development. Examples of common antigens associated with transformed cells are sialyl Lewis a, sialyl Lewis x, sialyl T, sialyl Tn, and polysialic acid (PSA). Jorgensen et al., Cancer Res. (1995) 55, 1817-1819; Sell, *Hum. Pathology* (1990) 21, 1003-1019; Taki et al., *J. Biochem.* (1988) 103, 998-1003; Gabius, *Angew. Chem. Int. Ed. Engl.* (1988) 27, 1267-1276; Feizi, *Trends Biochem. Sci.* (1991) 16, 84-86; Taylor-Papadimitriou and Epenetos, *Trends Biotech.* (1994) 12, 227-233; Hakomori and Zhang, *Chem. Biol.* (1997) 4, 97-104; Dohi et al., *Cancer* (1994) 73, 1552. In certain embodiments, the antigens each contain a terminal sialic acid. PSA is a homopolymer of sialic acid residues up to 50 units in length. Elevated levels of sialic acid are highly correlated with the transformed phenotype in many cancers, including gastric (Dohi et al., *Cancer* (1994) 73, 1552; and Yamashita, et al., *J. Natl. Cancer Inst.* (1995) 87, 441-446), colon (Yamashita, et al., *J. Natl. Cancer Inst.* (1995) 87, 441-446; Hanski et al., *Cancer Res.* (1995) 55, 928-933; Hanski et al., *Cancer Res.* (1993) 53, 4082-4088; Yang et al., *Glycobiology* (1994) 4, 873-884; Saitoh et al., *J. Biol. Chem.* (1992) 267, 5700-5711), pancreatic (Sawada et al., *Int. J. Cancer* (1994) 57, 901-907), liver (Sawada et al., *J. Biol. Chem.* (1994) 269, 1425-1431), lung (Weibel et al., *Cancer Res.* (1988) 48, 4318-4323), prostate (Jørgensen, et al., *Cancer Res.* (1995) 55, 1817-1819), kidney (Roth, et al., *Proc. Natl. Acad. Sci. USA* (1988) 85, 2999-3000), and breast cancers (Cho, et al., *Cancer Res.* (1994) 54, 6302-6305), as well as several types of leukemia (Joshi, et al., *Cancer Res.* (1987) 47, 3551-3557; Altevogt, et al. *Cancer Res.* (1983) 43, 5138-5144; Okada, et al., *Cancer* (1994) 73, 1811-1816). A strong correlation between the level of cell surface sialic acid and metastatic potential has also been observed in several different tumor types (Kakeji, et al., *Brit. J. Cancer* (1995) 71, 191-195; Takano, et al., *Glycobiology* (1994) 4, 665-674). The collective display of multiple sialylated antigens on a single cancer cell can account for the fact that so many different tumor types share the high sialic acid phenotype without necessarily expressing an identical complement of antigens (Roth, et al., supra). Consequently, diagnostic or therapeutic strategies that target cells on the basis of sialic acid levels have broad applicability to many cancers.

Introduction and incorporation of unnatural azidosugars (ManNAz, GalNAz) into living animals provides for detection of changes in metabolic state. Via the attachment of the appropriate epitope tag, the modified cyclooctyne can label these cells in a living organism, and consequently detect changes in metabolic state. Early detection of tumorigenic cells and subsequent intervention may facilitate a reduction in the severity and an increase in survival rates for cancer patients.

Materials Applications

In some embodiments, the subject modified cycloalkyne compound is useful in materials applications. A subject cycloalkyne compound (e.g., a subject azacycloalkynone) can be dimerized such that there are two azacycloalkynone cores linked by a linkage, such as in Formula V. A subject cycloalkyne compound (e.g., a subject azacycloalkynone) can be polymerized to form trimers, tetramers, pentamers, hexamers, etc., where the polymers can be linear or branched. The polymerized materials can be used to polymerize a monomeric unit, where the monomeric unit $R_1$ is within a compound of the formula $N_3$—$R_1$—$N_3$. $R_1$ can be an aryl, a substituted aryl, an alkyl, a substituted alkyl, an alkyl ester, etc. Other monomer units that can be polymerized include polymers of amino acids (polypeptides); non-peptide polymeric compounds; and cells. Reaction of a compound of the formula $N_3$—$R_1$—$N_3$ with a compound of Formula V results in multimerization (polymerization) of the monomeric unit $R_1$.

In some embodiments, a compound of Formula V is reacted with a compound of the formula $N_3$—$R_1$—$N_3$ and a compound of the formula $N_3$—$R_2$—$N_3$, where $R_1$ is a first polymer and $R_2$ is a second polymer. Reaction of $N_3$—$R_1$—$N_3$ and $N_3$—$R_2$—$N_3$ with a compound of Formula V co-polymerizes $R_1$ and $R_2$.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Synthesis of Biarylazacyclooctynone (BARAC) Compounds

Materials and Methods

All chemical reagents were purchased from Sigma-Aldrich, Acros and TCI chemicals and used without purification unless noted otherwise. Anhydrous DMF and MeOH were purchased from Aldrich or Acros in sealed bottles; all other solvents were purified as described by Pangbom et al., *Organometallics* (1996), 15, 1518. Magnesium sulfate was used as a drying agent and solvent was removed by reduced pressure with a Buchi Rotovapor R-114 equipped with a Welch self-cleaning dry vacuum. Products were further dried by reduced pressure with an Edwards RV5 high vacuum. Thin layer chromatography was performed EMD Silica Gel 60 $F_{254}$ plates. Unless otherwise specified, $R_f$ values are reported in the solvent system the reaction was monitored in. Flash chromatography was performed using Silicycle SiliaFlash® P60 230-400 mesh silica.

All $^1$H and $^{13}$C NMR spectra are reported in ppm and referenced to solvent peaks. Spectra were obtain on Bruker AVQ-400®, AVB-400®, DRX-500®, AV-500®, or AV-600® instruments. IR spectra were obtained using a Nicolet Magna-IR 850 spectrometer using thin films on NaCl plates. High resolution fast atom bombardment (FAB) and electrospray ionization (ESI) mass spectra were obtained from the UC Berkeley Mass Spectrometry Facility. Flash column chromatography was performed using Silicycle Silica Flash P60 silica (40-63 μm, 230-400 mesh). High pressure liquid chromatography purifications were performed on a Varian ProStar HPLC equipped with UV/vis detector using a 100 Å C18 column (250×21.4 mm) at a flow rate of 20 mL/min.

Synthesis of Compounds:

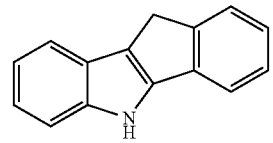

Compound 9

5,10-dihydroindeno[1,2-b]indole (Compound 9)

A modified version of the method reported by Okamoto, et al. was employed. Okamoto, T. A.; Kobayashi, S. M.; Yamamoto, H. N., DE1952019, 1970. To a solution of 2-indanone (16.3 g, 123 mmol) in ethanol (80 mL) was added phenyl hydrazine (12.1 mL, 123 mmol) followed by acetic acid (12 drops) at room temperature. While stirring, the solution was warmed to reflux (oil bath at 85° C.) for 15 minutes at which point it was removed from the oil bath and allowed to cool to room temperature. Light yellow needle-like crystals precipitated from the solution. Upon cooling to room temperature, the solution was cooled to 0° C. for 30 minutes. The crystals were filtered via vacuum filtration and used without further purification.

The crystals were added to a 500 mL Erlenmeyer flask and dissolved in 250 mL conc. HCl. This solution was heated to reflux (oil bath at 95° C.) and vigorously stirred for 10 minutes. As the reaction proceeded the product began to precipitate out of solution. The solution was cooled to room temperature and poured into 300 mL of water and the product precipitated as a brown solid. The solid was collected by vacuum filtration, azeotroped once with toluene and concentrated in vacuo to a brown powder (20 g, 97 mmol, 79%). The product was purified by recrystallization from acetone. Either the recrystallized product or the unpurified material was used in the next step, but we observed a minimal loss in yield for the next step using the unpurified material.

$^1$HNMR (500 MHz, CDCl$_3$) δ 8.35 (1H, br s), 7.65 (1H, d, J=7.0 Hz), 7.55 (1H, d, J=7.0 Hz), 7.48-7.43 (m, 2H), 7.34 (1H, t, J=7.5 Hz), 7.24-7.16 (3H, m), 3.74 (2H, s): $^{13}$CNMR (125 MHz, CDCl$_3$) δ 148.0, 143.5, 140.5, 135.1, 126.7, 125.7, 125.0, 121.9, 120.4, 119.1, 117.5, 112.2, 30.5.

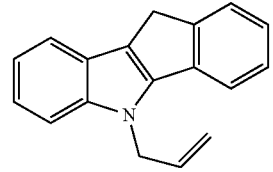

Compound 18

5-allyl-5,10-dihydroindeno[1,2-b]indole (Compound 18)

To a solution of compound 9 (2.05 g, 10.0 mmol, unpurified from the previous protocol) in toluene (30 mL) was added tetrabutylammonium bromide (100 mg, cat.) and allyl bromide (1.74 mL, 20.0 mmol). To this solution was added a solution of sodium hydroxide (6 mL, 50% in water) and stirred vigorously at room temperature for 12 hours. The solution was diluted with toluene (50 mL) and the organic layer was separated from the aqueous layer. The aqueous layer was extract with toluene (2 times with 25 mL toluene)

and the organic layers were pooled, dried over MgSO$_4$, filtered and concentrated in vacuo to a brown oil. The oil was purified via silica gel column chromatography (8:1 hexanes:ethyl acetate, R$_f$=0.5) to yield an off-white crystalline solid (2.15 g, 8.78 mmol, 88%). $^1$HNMR (600 MHz, CDCl$_3$) δ 7.67-7.65 (1H, m), 7.57-7.54 (2H, m), 7.35 (1H, d, J=8.4 Hz), 7.34 (1H, t, J=7.8 Hz), 7.25-7.21 (2H, m), 7.19-7.16 (1H, m), 6.14-6.07 (1H, m), 5.20-5.18 (1H, m), 5.08-5.04 (3H, m), 3.75 (2H, s): $^{13}$CNMR (150 MHz, CDCl$_3$) δ 148.3, 144.5, 141.4, 135.3, 133.5, 126.7, 125.7, 124.8, 124.4, 121.3, 120.8, 119.9, 119.2, 118.0, 116.8, 110.1, 47.0, 30.3: IR (cm$^{-1}$) 3583, 3397, 3055, 2921, 1645, 1610, 1526, 1496, 1461, 1440, 1407, 1383, 1345, 1265, 1153, 1104, 1020, 922, 736. HRMS (FAB) calcd for C$_{18}$H$_{15}$N [M]$^+$: 245.1199. found: 245.1205.

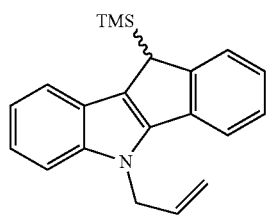

Compound 10

5-allyl-10-(trimethylsilyl)-5,10-dihydroindeno[1,2-b]indole (Compound 10)

To a room temperature solution of compound 18 (3.95 g, 16.1 mmol) in Et$_2$O (100 mL) in a room temperature water bath was added n-BuLi (12.6 mL, 1.4 M in hexanes, 17.6 mmol) over 60 minutes via syringe pump with stirring. After stirring for 2 additional hours at room temperature the red-brown solution was cooled to −78° C. Once cooled TMSCl (4.0 mL, 32 mmol) was added quickly drop-wise. The solution was immediately removed from the cold bath and allowed to warm to room temperature. The white precipitate was filtered from the solution and rinsed with Et$_2$O (30 mL). The solvent was removed to yield an oil. The oil was purified by silica gel column chromatography (10:1 hexanes:ethyl acetate, R$_f$=0.4) to yield a light yellow oil that solidified upon standing (4.76 g, 15.0 mmol, 93%). $^1$HNMR (600 MHz, CDCl$_3$) δ 7.67 (1H, d, J=7.8 Hz), 7.61 (1H, d, J=7.2 Hz), 7.53 (1H, d, J=7.8 Hz), 7.37 (1H, d, J=8.4 Hz), 7.31 (1H, t, J=7.2 Hz), 7.22-7.19 (2H, m), 7.14 (1H, t, J=7.2 Hz). 6.13-6.07 (1H, m), 5.15 (1H, d, J=13.3 Hz), 5.10 (2H, br s), 4.97 (1H, d, J=16.8 Hz), 3.81 (1H, s), −0.029 (9H, s): $^{13}$CNMR (150 MHz, CDCl$_3$) δ 150.1, 143.0, 141.5, 133.5, 133.4, 125.2, 124.7, 123.9, 123.8, 123.7, 121.2, 120.4, 119.3, 118.0, 116.5, 109.9, 46.8, 37.1, −2.2: IR (cm$^{-1}$) 3583, 3400, 3056, 2952, 1645, 1604, 1516, 1497, 1461, 1436, 1419, 1377, 1358, 1285, 1247, 1187, 1052, 840, 737. HRMS (FAB) calcd for C$_{21}$H$_{23}$NSi [M]$^+$: 317.1545. found: 317.1600.

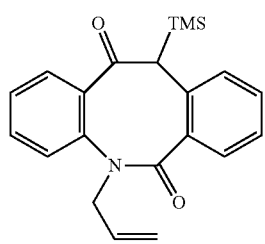

Compound 11

5-allyl-11-(trimethylsilyl)dibenzo[b,f]azocine-6,12(5H,11H)-dione (Compound 11)

To a solution of compound 10 (550 mg, 1.74 mmol) in a mixture of CH$_2$Cl$_2$ (50 mL) and NaHCO$_3$ (9 mL, sat. aq.) cooled to 0° C. was added m-CBPA (850 mg, 77% max., 3.8 mmol) portionwise over 5 minutes. After stirring for 30 minutes at 0° C. the solution was allowed to warm to room temperature for an additional 1.5 hours. The reaction was quenched with a solution of NaOH (20 mL, 1 N in water). The layers were separated and the aqueous layer was extracted with CH$_2$Cl$_2$ (2 times with 25 mL) and ethyl acetate (20 mL). The organic layers were combined and washed with brine, dried over MgSO$_4$, filtered and concentrated in vacuo to yield an oil that was used directly for the next reaction. $^1$HNMR (600 MHz, CDCl$_3$) δ 7.36-7.34 (1H, m), 7.25-7.18 (2H, m), 7.16-7.08 (2H, m), 7.04-7.02 (1H, m), 6.82-6.80 (1H, m), 5.86-5.80 (1H, m), 5.30-5.09 (2H, m), 4.40 (2H, d, J=7.2 Hz), 3.79 (1H, s), 0.15 (9H, s): $^{13}$CNMR (150 MHz, CDCl$_3$) δ 207.8, 169.9, 140.4, 138.1, 136.5, 136.1, 132.6, 130.5, 130.4, 129.9, 128.8, 128.7, 127.0, 126.7, 126.6, 126.1, 119.7, 58.4, 52.0, −0.18.

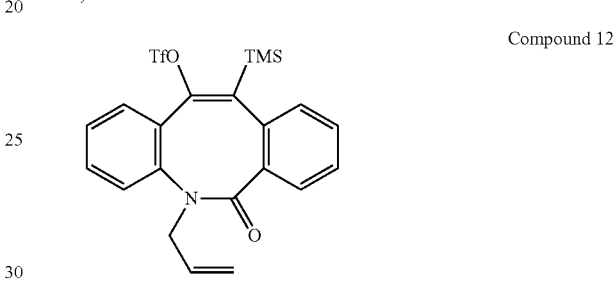

Compound 12

5-allyl-6-oxo-11-(trimethylsilyl)-5,6-dihydrodibenzo[b,f]azocin-12-yl trifluoromethanesulfonate (Compound 12)

To a solution of compound II (1.74 mmol assuming 100% yield) in THF (20 mL) at −78° C. was added KHMDS (3.8 mL, 0.5 M in toluene, 1.9 mmol) dropwise. After 30 minutes of stirring at −78° C., Tf$_2$O (0.34 mL, 2.0 mmol) was added dropwise. The reaction was stirred for an additional 1.5 hours at −78° C. and then diluted with Et$_2$O (30 mL) and warmed to room temperature. Upon reaching room temperature the solution was worked up with NaHCO$_3$ (10 mL, sat. aq.). The organic layer was washed with ethyl acetate (30 mL). The organic layers were collected, dried over MgSO$_4$, filtered and concentrated in vacuo to a yellow oil. The oil was purified by silica gel column chromatography (4:1 hexanes:ethyl acetate, R$_f$=0.65 in 2:1 hexanes:ethyl acetate) to yield a yellow oil that solidified upon standing (456 mg, 0.95 mmol, 55% over 2 steps). $^1$HNMR (400 MHz, CDCl$_3$) δ 7.32-7.23 (4H, m), 7.20-7.13 (3H, m), 6.85-6.83 (1H, m), 6.21-6.11 (1H, m), 5.30-5.29 (1H, m), 5.26-5.25 (1H, m), 4.85 (1H, dd, J=15.2, 4.8 Hz), 3.94 (1H, dd, J=15.6, 7.2 Hz), 0.29 (9H, s): $^{19}$FNMR (400 MHz, CDCl$_3$) δ −73.0: $^{13}$CNMR (125 MHz, CDCl$_3$) δ 169.9, 149.2, 143.7, 139.2, 136.0, 135.9, 133.9, 131.3, 130.9, 129.0, 128.5, 127.5, 127.3, 127.1, 126.8, 125.9, 118.0 (q, J=325 Hz), 117.7, 53.4, −0.51. IR (cm$^{-1}$) 3391, 3078, 2957, 2927, 2360, 2342, 1653, 1596, 1487, 1449, 1417, 1386, 1313, 1253, 1216, 1139, 992, 910, 862, 844, 825, 766. HRMS (FAB) calcd for C$_{22}$H$_{23}$O$_4$NF$_3$SSi [M+H]$^+$: 482.1064. found: 482.1071.

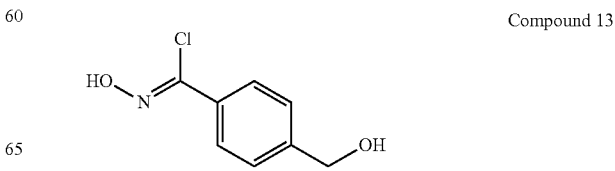

Compound 13

N-hydroxy-4-(hydroxymethyl)benzimidoyl chloride (Compound 13)

To a solution of 4-(hydroxymethyl)benzaldehyde as reported by Zaidi, et al. (3.4 g, 25 mmol) and NH$_2$OH.HCl (1.9 g, 27 mmol) in a 1 to 1 mixture of water and ethanol (14 mL) was added ice (10 g) as reported by Liu, et al. Zaidi, S. H. H.; Loewe, R. S.; Clark, B. A.; Jacob, M. J.; Lindsey, J. S., *Organic Process Research & Development* (2006), 10, 304-314; Liu, K.-C.; Shelton, B. R.; Howe, R. K., *J. Org. Chem.*, (1980), 45, 3916-3918. To this stirred solution was added NaOH (2.5 g in 2.5 mL water, 60 mmol) slowly. After stirring at room temperature for 1.5 hours the solution was washed with Et$_2$O (25 mL) and the Et$_2$O was discarded. The aqueous layer was acidified with HCl (1 N in water) and extracted with CH$_2$Cl$_2$ (three times with 25 mL) and Et$_2$O (two times with 25 mL). The organic layers were dried over MgSO$_4$, filtered and concentrated in vacuo to a white solid that was used without further purification.

To a solution of the oxime (500 mg, 3.3 mmol), in DMF (2.5 mL) was added N-chlorosuccinimide (440 mg, 3.3 mmol) portionwise as reported by Liu, et al. Liu, K.-C.; Shelton, B. R.; Howe, R. K., *J. Org. Chem.*, (1980), 45, 3916-3918. A small portion (~0.2 mL) of HCl gas from the headspace above a solution of conc. HCl was bubbled into the solution to ensure initiation of the reaction. After the reaction warmed and subsequently cooled back to room temperature, water (10 mL) was added and the product was extracted with Et$_2$O (three times with 20 mL). The organic layer was dried over MgSO$_4$, filtered and concentrated in vacuo to yield a white solid (330 mg, 1.8 mmol, 55%), which was used without further purification.

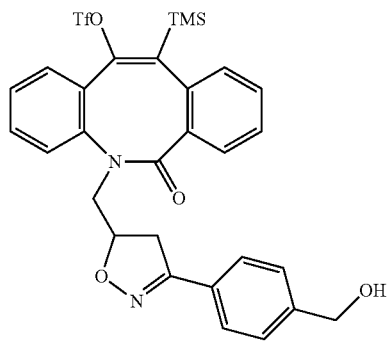

Compound 14

(Z)-5-((3-(4-(hydroxymethyl)phenyl)-4,5-dihydroisoxazol-5-yl)methyl)-6-oxo-11-(trimethylsilyl)-5,6-dihydrodibenzo[b,f]azocin-12-yl trifluoromethanesulfonate (Compound 14): To a room temperature heterogeneous solution of compound 12 (480 mg, 1.00 mmol) and compound 13 (204 mg, 1.1 mmol) in CH$_2$Cl$_2$ (6 mL) was added a solution of NEt$_3$ (0.18 mL, 2.5 mmol) in CH$_2$Cl$_2$ (4 mL) dropwise via syringe pump over 2 hours. After the addition was complete the homogenous solution was stirred for an additional 24 hours. The solution was concentrated in vacuo to a yellow oil which was purified by silica gel column chromatography (2:1 to 1:1 hexanes:ethyl acetate, R$_f$=0.25 and 0.20 in 1:1) to give compound 14 (two separable diastereomers, total yield of 295 mg, 0.47 mmol, 47%) and unreacted compound 12 (74 mg, 0.15 mmol, 56% yield based on recovered starting material). Less Polar Diastereomer: $^1$HNMR (600 MHz, CDCl$_3$) δ 7.84 (1H, d, J=8.4 Hz), 7.67 (2H, d, J=8.4 Hz), 7.40 (2H, d, J=8.4 Hz), 7.36-7.34 (1H, m), 7.28-7.26 (1H, m) 7.20-7.14 (4H, m), 6.85-6.83 (1H, m), 5.65-5.62 (1H, m), 4.71 (2H, s), 4.46 (1H, dd, J=14.4, 2.4 Hz), 3.56 (1H, dd, J=16.8, 10.8 Hz), 3.20 (1H, dd, J=14.4, 9.6 Hz), 3.02 (1H, dd, J=16.8, 7.2 Hz), 2.35 (1H, br s), 0.28 (9H, s). $^{19}$FNMR (564 MHz, CDCl$_3$) δ -74.7. $^{13}$CNMR (150 MHz, CDCl$_3$) δ 171.0, 156.9, 149.4, 143.8, 143.5, 139.3, 136.2, 135.5, 132.3, 132.0, 130.6, 130.1, 128.7, 128.5, 128.4, 127.63, 127.59, 127.4, 127.3, 127.2, 127.1, 127.0, 126.4, 118.1 (q, J=319 Hz), 77.8, 64.7, 56.6, 39.0, -0.5. More polar diastereomer: $^1$HNMR (600 MHz, CDCl$_3$) δ 7.72 (2H, d, J=7.8 Hz), 7.46 (1H, d, J=8.4 Hz), 7.42 (2H, d, J=8.4 Hz), 7.34-7.31 (2H, m), 7.19 (1H, t, J=8.4 Hz), 7.15 (1H, t, J=7.2 Hz), 7.10-7.05 (2H, m), 6.82 (1H, d, J=7.8 Hz), 4.97-4.94 (1H, m), 4.74 (2H, s), 4.35 (1H, dd, J=14.4, 4.8 Hz), 4.03 (1H, dd, J=14.4, 5.4 Hz), 3.60 (1H, dd, J=16.8, 7.8 Hz), 3.48 (1H, dd, J=16.8, 10.8 Hz), 0.29 (9H, s): $^{19}$FNMR (564 MHz, CDCl$_3$) δ -74.7: $^{13}$CNMR (150 MHz, CDCl$_3$) δ 171.7, 157.3, 149.3, 143.2, 142.9, 139.5, 135.9, 131.8, 131.2, 129.2, 128.9, 128.6, 127.7, 127.32, 127.25, 127.18, 126.9, 126.3, 118 (q, 320 Hz), 79.4, 65.0, 52.5, 38.9, -0.51. IR (cm$^{-1}$) 3419, 3065, 2955, 2926, 2360, 2341, 1652, 1645, 1634, 1596, 1489, 1448, 1417, 1361, 1310, 1253, 1211, 1138, 1046, 992, 909, 863, 845, 825, 808, 767. HRMS (FAB) calcd for C$_{30}$H$_{30}$O$_6$N$_2$F$_3$SSi [M+H]$^+$: 631.1540. found: 631.1556.

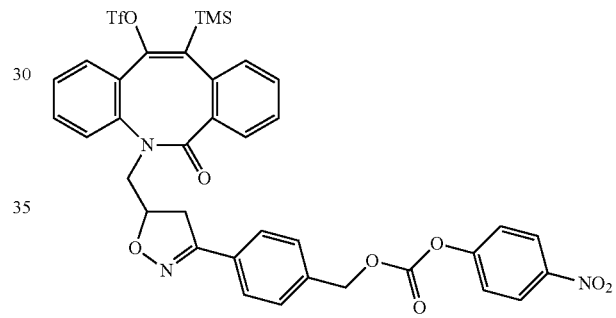

Compound 19

(Z)-5-((3-(4-(((4-nitrophenoxy)carbonyloxy)methyl)phenyl)-4,5-dihydroisoxazol-5-yl)methyl)-6-oxo-11-(trimethylsilyl)-5,6-dihydrodibenzo[b,f]azocin-12-yl trifluoromethanesulfonate (Compound 19): To a mixture of both diastereomers of compound 14 (56 mg, 0.088 mmol) in CH$_2$Cl$_2$ (1.5 mL) and pyridine (0.035 mL, 0.35 mmol) was added p-nitrophenyl chloroformate (42 mg, 0.21 mmol) all at once. After stirring at room temperature for 3 hours the reaction was diluted with CH$_2$Cl$_2$ (5 mL) and water (3 mL) was added to quench excess reagent. The layers were separated and the aqueous layer was extracted with CH$_2$Cl$_2$ (3 times with 10 mL). The organic layers were dried over MgSO$_4$, filtered and concentrated in vacuo to a yellow oil. The oil was purified by silica gel column chromatography (3:1 hexanes: ethyl acetate, R$_f$ hexanes:ethyl acetate for the two diastereomers) to yield a yellow solid (64 mg, 0.081 mmol, 91%). $^1$HNMR (400 MHz, CDCl$_3$) (1:0.5 mix of separable diastereomers) δ 8.25-8.22 (2H, m), 7.83 (0.6H, d, J=8.4 Hz), 7.77-7.72 (1.9H, m), 7.51-7.42 (1.8H, m), 7.40-7.30 (3.3H, m), 7.24-7.11 (3.6H, m), 7.10-7.02 (0.5H, m), 6.85-6.81 (0.9H, m), 5.69-5.62 (0.6H, m), 5.32-5.29 (2H, 2 singlets), 5.00-4.94 (0.3H, m), 4.48 (0.6H, dd, J=14.4, 2.0 Hz), 4.32 (0.3H, dd, J=14.4, 4.8 Hz), 4.05 (0.3H, dd, J=15.6, 5.6 Hz), 3.65-3.58 (1H, m), 3.57-3.45 (0.3H, m), 3.39 (0.15H, d, J=6.4 Hz), 3.21 (0.6H, dd, J=14.4, 9.6 Hz), 3.06 (0.6H, dd, J=16.8, 7.2 Hz), 0.29-0.27 (9H, two s): $^{19}$FNMR (376 MHz, CDCl$_3$) δ -72.9, -73.0: $^{13}$CNMR (100 MHz, CDCl$_3$) δ 171.7, 170.9, 157.0, 156.5, 155.5, 152.5, 149.8, 145.5, 143.8, 142.7, 139.3, 136.3, 136.2, 135.7, 135.5, 131.9, 131.7, 131.0, 130.5, 130.0, 129.2, 128.9, 128.7, 128.6, 128.4, 127.64, 127.56, 127.3, 127.2, 127.15, 127.10, 126.9, 126.4, 126.3, 125.4, 123.8, 121.8, 79.5, 78.1, 70.3, 56.5, 52.5, 38.8, 21.1, 14.3, −0.5, −0.6.

BARAC (Compound 15) was synthesized as shown in Scheme 1.

Scheme 1: Synthesis of BARAC

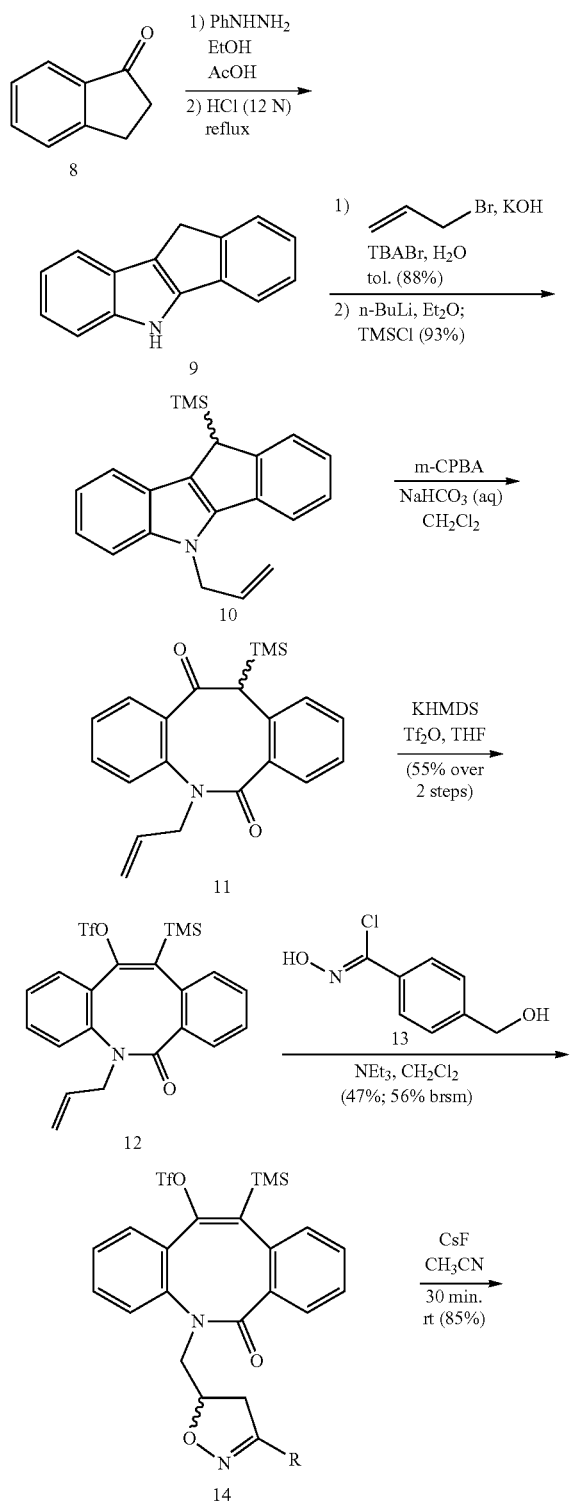

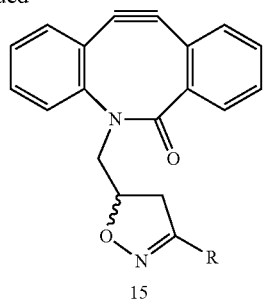

R = p-C$_6$H$_4$CH$_2$OH

Fisher indole synthesis gave indole (compound 9) as described in Okamoto, et al. Okamoto, T. A.; Kobayashi, S. M.; Yamamoto, H. N., German Pat. DE1952019 (1970). The Fisher indole step can be easily accomplished with a wide range of commercially available hydrazines and 1-indanones. The indole nitrogen was alkylated with allyl bromide using phase transfer conditions as reported by Nifant'ev, et al., to protect the indole nitrogen and also introduce a functional handle for future probe attachment. Nifant'ev, I. E.; Kashulin, I. A.; Bagrov, V. V.; Abilev, S. K.; Lyubimova, I. K. *Russian Chemical Bulletin*, (2001), 50, 1439-1445. This initial sequence was amenable to large-scale preparation with only one purification step at the end of the sequence. The TMS group was then installed in a straightforward manner to form compound 10.

Oxidation of indole (compound 10) with excess m-CPBA opened the central rings to give the cyclic keto-amide (compound 11), which was unstable to silica-gel purification. These reaction conditions left the terminal alkene untouched. Treatment of the potassium enolate of ketone (compound 11) with trifluoromethanesulfonyl anhydride gave compound 12. Selective reaction of the terminal alkene with a nitrile oxide generated in situ from chlorooxime (compound 13) installed a linker for conjugation to a probe molecule as reported by Huisgen, R. and Gutsmiedl, et al. Huisgen, R. *Angew. Chem. Int. Ed.*, (1963), 2, 565-598; and Gutsmiedl, K.; Wirges, C. T.; Ehmke, V.; Carell, T. *Org. Lett.*, 2009, 11, 2405-2408. Reaction of compound 14 with CsF introduced the strained alkyne in under 30 min at rt. The synthesis of BARAC (compound 15) from compound 9 was accomplished in 6 steps in 18% overall yield (see FIG. 11). BARAC (compound 15) was stable to traditional chromatography and storage at room temperature.

Compound 15

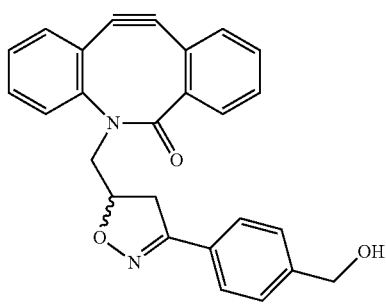

BARAC (Compound 15): To a mixture of both diastereomers of compound 14 (110 mg, 0.175 mmol) in CH$_3$CN (15 mL) was added CsF (160 mg, 1.05 mmol) all at once. The reaction was stirred vigorously for 45 minutes and then filtered. The solvent was removed and the resulting oil was purified by silica gel column chromatography (1:1 to 1:2 hexanes:ethyl acetate, $R_f$=0.1 in 1:1) to yield compound 15 as an off-white solid (61 mg, 0.15 mmol, 85%). Compound 15 was stored as a solid at 0° C. protected from light and oxygen. $^1$HNMR (400 MHz, CDCl$_3$) (0.8:1 mixture of rotamers) δ 7.73 (1H, d, J=7.6 Hz), 7.68-7.62 (1.9H, m), 7.60 (1.7H, d, J=8 Hz), 7.55-7.53 (2.8H, m), 7.49-7.41 (7.4H, m), 7.40-7.31 (7.4H, m), 4.87-4.76 (1.8H, m), 4.69, 4.66 (3.5H, 2 s), 3.48 (0.8H, dd, J=16.8, 10.4 Hz), 3.40-3.14 (3.8H, m), 3.00 (0.8H, dd, J=14.0, 5.6 Hz), 2.88 (1H, dd, J=14.4, 3.2 Hz), 2.80 (1H, dd, J=16.8, 7.6 Hz), 2.25 (1.5H, br s): $^{13}$CNMR (100 MHz, CDCl$_3$) δ 176.8, 176.6, 156.2, 156.1, 155.3, 155.1, 149.0, 148.8, 143.5, 143.4, 130.7, 130.4, 129.9, 129.7, 129.6, 129.1, 128.6, 128.5, 128.3, 128.2, 127.9, 127.8, 127.2, 127.1, 126.9, 126.8, 126.7, 126.4, 122.7, 122.6, 122.1, 122.0, 110.2, 110.1, 109.1, 109.0, 79.4, 79.0, 64.6, 55.5, 54.8, 38.8, 37.9. IR (cm$^{-1}$) 3426, 3064, 2924, 2247, 1666, 1659, 1650, 1594, 1467, 1449, 1355, 1244, 1046, 1015, 911, 762, 731.

Figure 12:
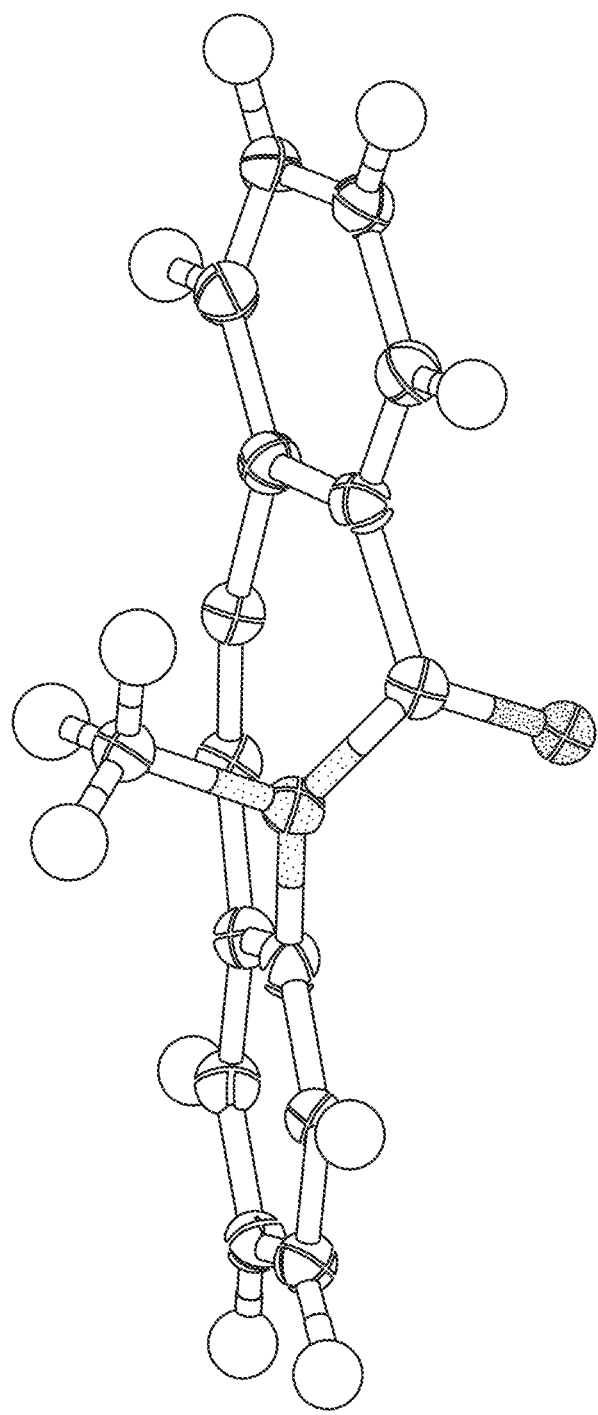
FIG. 12 shows the crystal structure of BARAC.

A crystal structure for the unsubstituted BARAC was obtained (FIG. 12).

BARAC-biotin (Compound 16) and BARAC-Fluor (Compound 17) were synthesized as shown in Scheme 2.

Scheme 2: Synthesis of BARAC-biotine and BARAC-Fluor

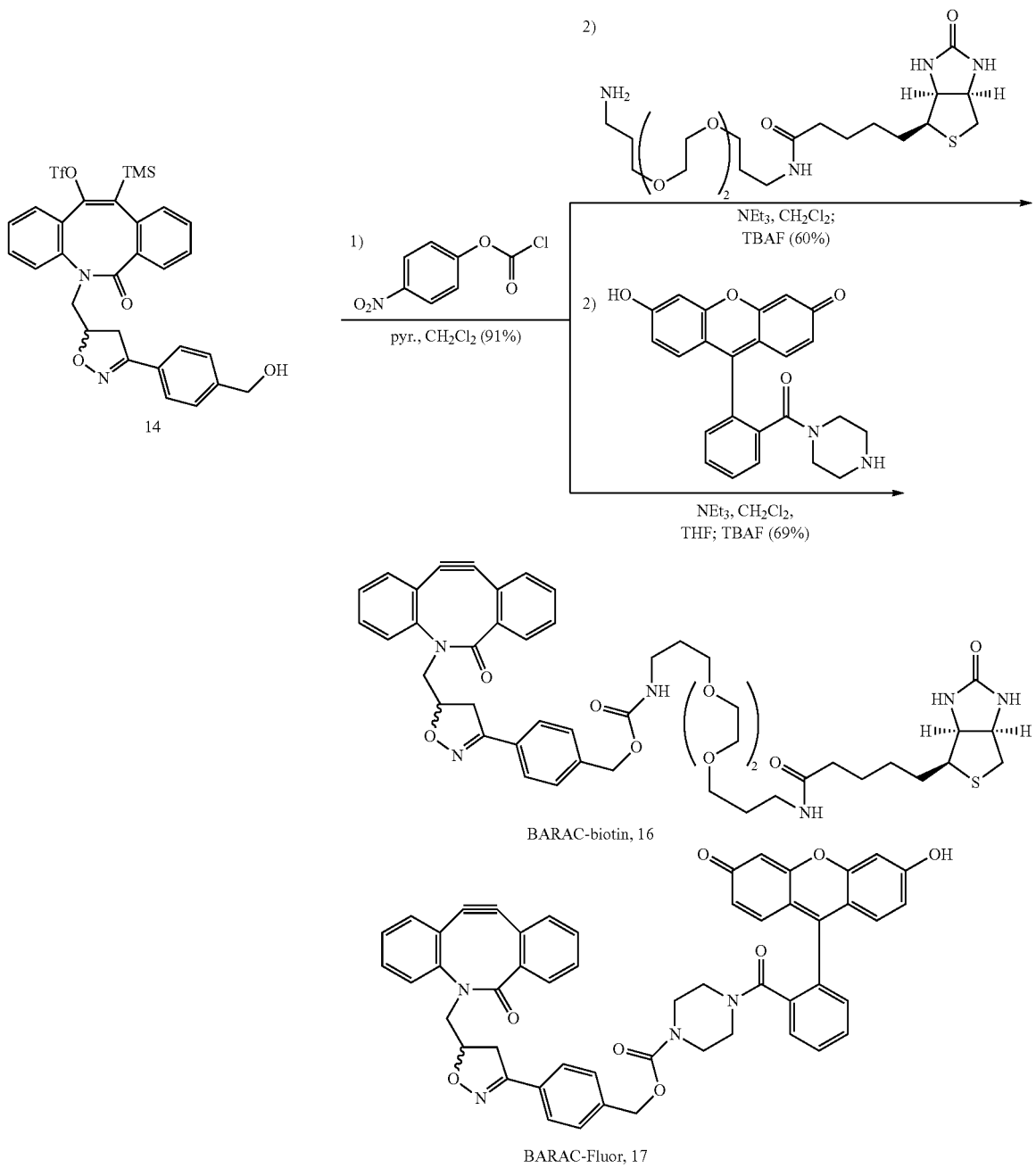

BARAC-biotin, 16

BARAC-Fluor, 17

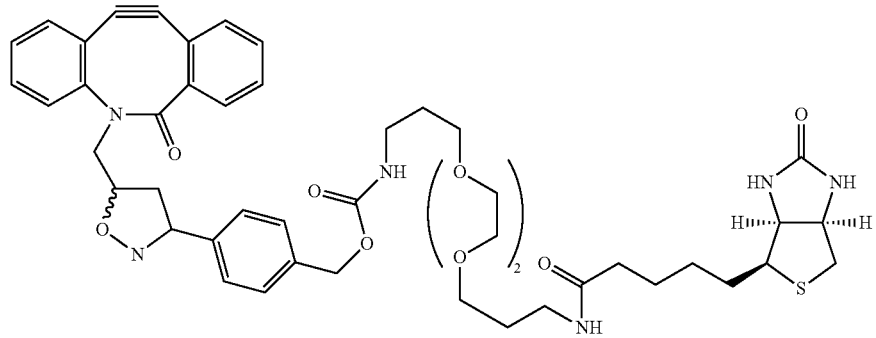

Compound 16

BARAC-biotin (Compound 16): To a flask containing compound 19 (68 mg, 0.086 mmol) was added a solution of N-(13-amino-4,7,10-trioxamidecanyl)biotinamide as reported by Wilbur, et al. (36 mg, 0.086 mmol) in CH$_2$Cl$_2$ (5.0 mL) with stirring. Wilbur, D. S.; Hamlin, D. K.; Vessella, R. L.; Stray, J. E.; Buhler, K. R.; Stayton, P. S.; Klumb, L. A.; Pathare, P. M.; Weerawarna, S. A. Bioconjug. Chem., (1996), 7, 689. After 5 minutes NEt$_3$ (1 drop) was added and the reaction was allowed to stir at room temperature for 3 hours until all of the starting material was consumed. To this solution was added tetrabutylammonium fluoride (0.20 mL, 1.0 M in THF, 0.20 mmol) and the solution was stirred at room temperature for 45 minutes. The solution was placed directly on to a silica gel column for chromatographic purification (7-10% MeOH in CH$_2$Cl$_2$, R$_f$=0.45 in 10% MeOH/CH$_2$Cl$_2$) to yield an off white solid (45 mg, 0.051 mmol, 60%). Compound 16 was stored as a solid at 0° C. protected from light and oxygen. $^1$HNMR (400 MHz, CDCl$_3$) δ 7.76-7.56 (7.8H, m), 7.43-7.28 (14.2H, m), 6.52 (1.6H, br s), 5.82-5.76 (1.2H, m), 5.66-5.58 (1.6H, m), 5.19-5.06 (4H, m), 5.02 (1.6H, s), 4.91-4.80 (1.6H, m), 4.46 (2H, br t), 4.26 (2H, br t), 3.66-3.49 (26.4H, m), 3.46-3.21 (12.6H, m), 3.16-3.09 (2H, m), 3.06-2.98 (0.7H, m), 2.94-2.79 (3.9H, m), 2.68 (2H, d, J=12.6 Hz), 2.16 (4H, m), 1.86-1.56 (18H, m), 1.46-1.36 (4.8H, m): $^{13}$CNMR (150 MHz, CDCl$_3$) δ 176.5, 173.2, 163.9, 156.4, 156.1, 156.0, 155.1, 149.0, 148.8, 139.3, 130.7, 130.4, 129.9, 129.7, 128.8, 128.7, 128.6, 128.5, 128.2, 127.9, 127.8, 126.9, 126.8, 126.6, 126.5, 126.4, 122.7, 122.6, 122.1, 122.0, 110.2, 110.1, 109.0, 79.5, 79.2, 70.54, 70.49, 70.2, 70.1, 69.9, 69.6, 65.8, 61.9, 60.2, 55.6, 55.4, 54.8, 50.8, 40.6, 39.2, 38.7, 37.8, 37.7, 36.0, 29.5, 29.0, 28.2, 28.1, 25.7, 24.0, 22.7, 19.8, 13.7. HRMS (FAB) calcd for C$_{47}$H$_{57}$O$_9$N$_6$S [M+H]$^+$: 881.3902. found: 881.3923.

Figure 7:
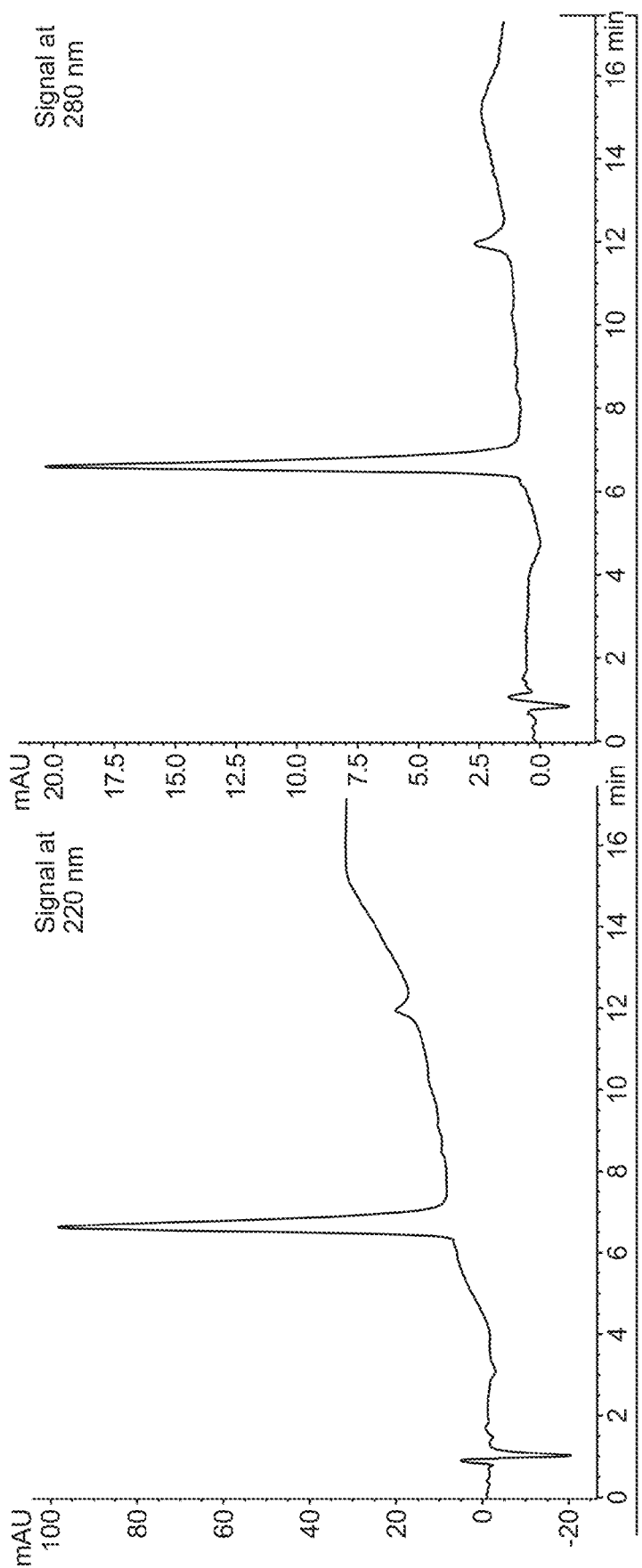
FIG. 7 shows analytical HPLC graphs of purified BARAC-Fluor according to embodiments of the present disclosure.

BARAC-Fluor (Compound 17): To a solution of compound 19 (30 mg, 0.040 mmol) and piperazine-fluorescein (Compound 20; as reported by Hangauer, M. J. and Bertozzi, C. R.) (16 mg, 0.040 mmol) in CH$_2$Cl$_2$ (2 mL) and THF (1 mL) was added NEt$_3$ (2 drops) with stirring. Hangauer, M. J.; Bertozzi, C. R. Angew. Chem. Int. Ed., (2008), 73, 1008-1017. The solution was stirred for 6 hours at room temperature and then warmed to 45° C. for 5 hours. After cooling the reaction to room temperature tetrabutylammonium fluoride (0.2 mL, 1.0 M in THF, 0.20 mmol) was added and this was allowed to stir for 30 minutes. The reaction mixture was concentrated in vacuo to an orange solid that was purified by silica gel column chromatography (10% methanol in CH$_2$Cl$_2$; R$_f$=0.4) to yield an orange solid (23 mg, 0.028 mmol, 69%). The identity of compound 17 was confirmed by mass spec and reactivity. The purity was confirmed by HPLC (FIG. 7). Compound 17 was stored as a solid at 0° C. protected from light and oxygen. HRMS (FAB) calcd for C$_{51}$H$_{38}$N$_4$O$_8$ [M+H]$^+$: 835.2762. found: 835.2769.

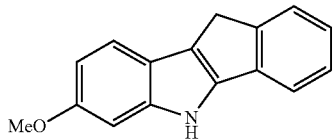

29a

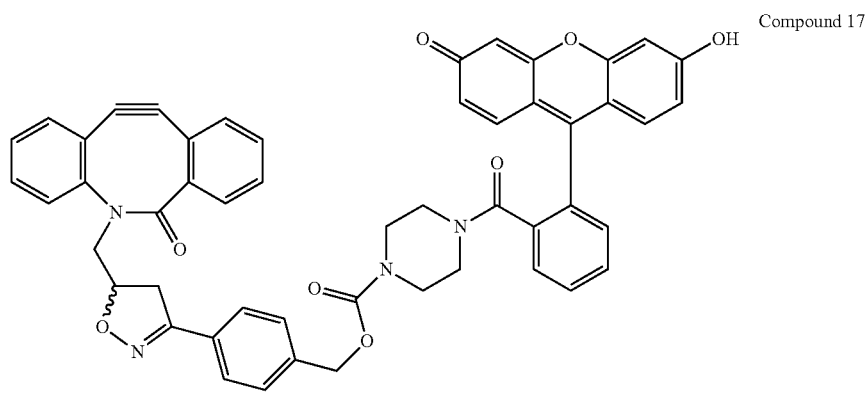 [SMILES: O=C(OCc1ccc(C2=NOC(CN3C(=O)c4ccccc4C#Cc4ccccc43)C2)cc1)N1CCN(C(=O)c2ccccc2-c2c3ccc(=O)cc-3oc3cc(O)ccc23)CC1]

Compound 17

7-methoxy-5,10-dihydroindeno[1,2-b]indole (29a)

To a solution of 3-methoxyphenylhydrazine hydrochloride (3.65 g, 20.9 mmol) and 1-indanone (2.77 g, 21.0 mmol) in ethanol (11.8 mL) was added glacial acetic acid (3 drops). The solution was stirred at reflux (85° C.) for 15 minutes and cooled to room temperature. Orange precipitate began to form upon cooling, and the mixture was subsequently emerged in an ice water bath to further induce crystallization. The solid was collected by vacuum filtration and dissolved in 22 mL isopropanol. Sulfuric acid (36 N, 1.5 mL) was added via syringe, and the resulting solution was stirred at reflux (90° C.) for 16 hours. Upon cooling to room temperature, the solution was basified to pH 10 with aqueous sodium hydroxide (2% by mass) resulting in the formation of precipitate. The solid was collected by vacuum filtration to yield 29a as an orange solid (2.55 g, 10.9 mmol). Crude product was brought on to the next step without purification. For purposes of characterization, the product was purified by flash column chromatography (20:1 hexanes—ethyl acetate). $^1$H NMR (600 MHz, CDCl$_3$): δ 8.18 (s, 1H), 7.50-7.52 (m, 2H), 7.40-7.41 (d, 1H, J=7.2 Hz), 7.30-7.32 (t, 1H, J=7.8 Hz), 7.16-7.19 (td, 1H, J=7.8, 1.2 Hz), 6.95 (d, 1H, J=2.4 Hz), 6.83-6.84 (dd, 1H, J=8.4, 2.4 Hz), 3.88 (s, 3H), 3.69 (s, 2H); $^{13}$C NMR (150 MHz, CDCl$_3$): δ 156.2, 147.3, 142.3, 141.5, 135.3, 126.5, 125.3, 124.1, 121.9, 119.5, 119.4, 116.7, 109.6, 96.2, 55.7, 30.3. FTIR: cm$^{-1}$ 3399, 1612, 1405, 1255, 1155, 1041, 820. ESI-HRMS: Calcd. for C$_{16}$H$_{13}$NO$^+$ [M]$^+$: 235.0992. found 235.0990.

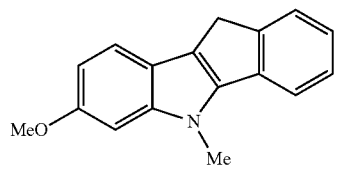

31a

7-methoxy-5-methyl-5,10-dihydroindeno[1,2-b]indole (31a)

To a solution of 29a (60.1 mg, 0.26 mmol) in benzene (2 mL) was added aqueous sodium hydroxide (50% by mass, 540 μL), tetrabutylammonium iodide (50 mg, 0.14 mmol), and iodomethane (130 μL, 2.09 mmol). The reaction mixture was stirred vigorously at 40° C. for 16 hours and then at 55° C. for 2 additional hours. Upon cooling to room temperature, the mixture was diluted with benzene (10 mL) and H$_2$O (10 mL), and the aqueous layer was extracted 2×10 mL ethyl acetate. Organic layers were combined, washed 1×15 mL H$_2$O, dried over anhydrous magnesium sulfate and concentrated to yield a brown solid. Crude product was purified by flash column chromatography (20:1 to 10:1 hexanes—ethyl acetate) to give a tan brown solid in 64% yield (40 mg, 0.16 mmol). $^1$H NMR (600 MHz, CDCl$_3$): δ 7.60 (d, 1H, J=7.8 Hz), 7.51-7.52 (m, 2H), 7.32-7.34 (t, 1H, J=7.2 Hz), 7.18-7.20 (t, 1H, J=7.2 Hz), 6.84-6.85 (m, 2H), 3.98 (s, 3H), 3.93 (s, 3H), 3.66 (s, 2H); $^{13}$C NMR (150 MHz, CDCl$_3$): δ 156.0, 147.6, 143.8, 142.7, 135.7, 126.4, 125.4, 123.9, 120.3, 119.6, 118.7, 116.9, 108.9, 93.8, 55.7, 31.1, 30.1. FTIR: cm$^{-1}$ 2935, 1605, 1566, 1492, 1385, 1310, 1263, 1230, 1210, 1040, 812, 755. EI-HRMS: Calcd. for C$_{17}$H$_{15}$NO$^+$ [M]$^+$: 249.1154. found 249.1158.

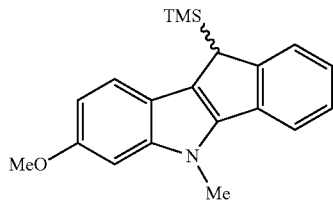

32a

7-methoxy-5-methyl-10-(trimethylsilyl)-5,10-dihydroindeno[1,2-b]indole (32a)

Compound 31a (240 mg, 0.96 mmol) was dissolved in anhydrous ether (6.5 mL) and the reaction mixture was immersed in a 25° C. water bath. n-BuLi (1.5M in hexanes, 742 μL, 1.11 mmol) was added dropwise via syringe pump over one hour. Following addition of base, the reaction mixture was stirred for one hour at 25° C. and then cooled to −78° C. TMSCl (256 μL, 2.02 mmol) was added rapidly via syringe and the resulting cloudy mixture was immediately warmed to 25° C. for 1.5 hours. The reaction mixture was diluted with 20 mL ether, filtered, and concentrated in vacuo to yield a brown solid which was subsequently purified by flash column chromatography (15:1 hexanes-ethyl acetate) to give a yellow solid in 34% yield (104 mg, 0.32 mmol). $^1$H NMR (600 MHz, CDCl$_3$): δ 7.69 (d, 1H, 7.8 Hz), 7.53 (d, 1H, J=9.0 Hz), 7.51 (d, 1H, J=7.2 Hz), 7.29-7.32 (t, 1H, J=7.8 Hz), 7.16-7.18 (td, 1H, J=7.2, 1.2 Hz), 6.87 (d, 1H, J=2.4 Hz), 6.80-6.82 (dd, 1H, J=9.0, 2.4 Hz), 4.05 (s, 3H), 3.92 (s, 3H), 3.73 (s, 1H), 0.03 (s, 9H); $^{13}$C NMR (150 MHz, CDCl$_3$): δ 155.9, 149.4, 142.9, 142.5, 133.9, 125.0, 124.5, 123.3, 123.0, 120.7, 118.3, 116.9, 108.3, 93.7, 55.7, 36.9, 31.3, −2.4. FTIR: cm$^{-1}$ 1619, 1370, 1212, 1106, 1062, 1035, 838, 805. EI-HRMS: Calcd. for C$_{20}$H$_{23}$NOSi$^+$ [M]$^+$: 321.1549. found 321.1546.

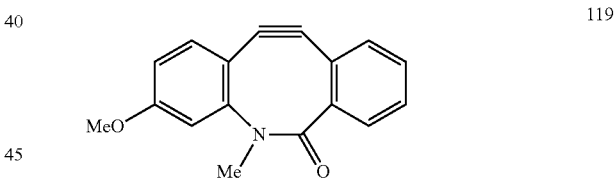

119

Methoxy-BARAC (119).

To a solution of 32a (37.5 mg, 0.116 mmol) in dichloromethane (3.33 mL) and saturated aqueous NaHCO$_3$ (700 μL) at 0° C. was added m-CPBA portionwise over 3 minutes. The mixture was stirred at 0° C. for 20 minutes and then warmed to room temperature over 40 minutes. The reaction was quenched via addition of 1N NaOH (4 mL) and the resulting aqueous layer was extracted 2×10 mL dichloromethane and 1×10 mL ethyl acetate. Organic layers were combined and washed 1×25 mL brine, dried over anhydrous magnesium sulfate, and concentrated in vacuo to yield a yellow oil (33a), which was immediately brought on to the next step without purification.

To a solution of 33a (0.16 mmol assuming 100% yield from the previous step) in anhydrous THF at −78° C. was added potassium hexamethyldisilazide (0.5 M in toluene, 351 μL, 0.18 mmol) dropwise via syringe to give a dark red solution which was stirred an additional 10 minutes at −78° C. Triflic anhydride (32 μL, 0.19 mmol) was then added and the solution immediately turned yellow. The solution was stirred for 30 minutes at −78° C. prior to dilution with 5 mL anhydrous ether and addition of tetrabutyl ammonium fluoride (1M in THF, 1.25 mL). After five additional minutes at −78° C., the reaction mixture was warmed to room temperature over 40 minutes then quenched with saturated aqueous NaHCO₃ (7 mL). The aqueous layer was subsequently extracted 1×15 mL ethyl acetate and the organic layer was dried over anhydrous magnesium sulfate and concentrated to yield a red/brown oil. Product was purified by flash column chromatography (10:1 to 2:1 hexanes-ethyl acetate) to yield 119 as a red solid in 10% yield (2.9 mg, 0.01 mmol). ¹H NMR (600 MHz, CDCl₃): δ 7.57-7.59 (m, 1H), 7.40-7.45 (quin d, 2H, J=7.5, 7.8, 1.2 Hz), 7.32-7.35 (m, 2H), 7.21 (d, 1H, J=2.4 Hz), 6.90-6.91 (dd, 1H, J=8.4, 2.4 Hz), 3.87 (s, 3H), 2.73 (s, 3H); ¹³C NMR (150 MHz, CDCl₃): δ 176.8, 161.0, 158.1, 148.9, 129.3, 128.2, 128.1, 126.0, 125.5, 122.7, 115.9, 113.8, 113.5, 108.9, 108.2, 55.6, 38.7. FTIR: cm⁻¹ 12925, 1668, 1597, 1292, 1074, 666. ESI-HRMS: Calcd. for C₁₇H₁₄O₂N⁺ [M+H]⁺: 264.1019. found 264.1021.

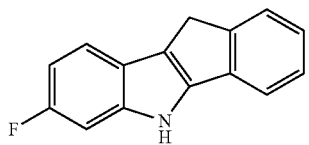

7-fluoro-5,10-dihydroindeno[1,2-b]indole (29b)

3-fluorophenylhydrazine hydrochloride (2.00 g, 12.3 mmol) and 1-indanone (1.63 g, 12.3 mmol) were dissolved in ethanol (31 mL) and stirred at reflux (85° C.) for 12 minutes. Glacial acetic acid (3 drops) was added, and the solution was stirred an additional 5 minutes at 85° C., then cooled to room temperature. Ethanol was removed under reduced pressure to yield a brown/red solid which was subsequently dissolved in isopropanol (21 mL). Sulfuric acid (36 N, 1.4 mL) was added to the reaction mixture via syringe and the resulting solution was stirred at reflux (90° C.) for 16 hours. Upon cooling to room temperature, the solution was basified to pH 10 with aqueous sodium hydroxide (2% by mass) resulting in the formation of a green precipitate. This solid was collected by vacuum filtration, dissolved in dichloromethane, and diluted with water. The aqueous layer was extracted 3×15 mL dichloromethane, and the remaining organic layer was dried over anhydrous magnesium sulfate and concentrated to yield a brown solid as a mixture of regioisomers (2:1.1) in 78% crude yield (2.14 g, 9.6 mmol). This mixture was brought on to the next step without further purification. For purposes of characterization, a small fraction of desired product was purified by numerous passes through a biotage 40M column (20:1 hexanes-ethyl acetate). ¹H NMR (600 MHz, CDCl₃): δ 8.32 (s, 1H), 7.52-7.56 (m, 2H), 7.45 (d, 1H, J=7.2 Hz), 7.32-7.34 (t, 1H, J=7.8 Hz), 7.20-7.23 (td, 1H, J=5.4, 1.2 Hz), 7.12-7.14 (dd, 1H, J=9.6, 1.8 Hz), 6.91-6.94 (m, 1H), 3.71 (s, 2H). ¹³C NMR (150 MHz, CDCl₃): δ 159.6 (d, J=235.5 Hz), 147.4, 143.5 (d, J=3.5 Hz), 140.6 (d, J=12.3 Hz), 134.9, 126.6, 125.5, 124.7, 121.6, 121.5, 119.4 (d, J=9.0 Hz), 117.1, 108.7 (d, J=25.5 Hz), 98.6 (d, J=27.0 Hz), 30.3; ¹⁹F NMR (CD₃CD, 376 MHz): δ −120.1--120.0 (td, J=9.3, 5.3 Hz), −122.0 (m) (note—the second peak in the fluorine spectrum is likely a result of unreacted hydrazone intermediate); FTIR: cm⁻¹ 3404, 2921, 1726, 1580, 1408, 1289, 1131, 758. ESI-HRMS: Calcd. for C₁₅H₁₀FN⁺ [M]⁺: 223.0792. found 223.0792.

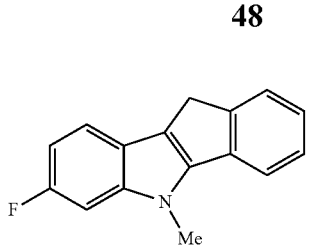

7-fluoro-5-methyl-5,10-dihydroindeno[1,2-b]indole (31b)

To a solution of 29b (as a 2:1.1 mixture of regioisomers, 2.14 g, 9.58 mmol) in benzene (31 mL) was added aqueous sodium hydroxide (50% by mass, 5.00 mL), tetrabutylammonium iodide (184 mg, 0.50 mmol), and iodomethane (4.77 mL, 76.6 mmol). The reaction mixture was stirred vigorously at 40° C. for 17.5 hours and subsequently cooled to room temperature. The solution was then diluted with benzene (10 mL) and H₂O (10 mL), and the aqueous layer was extracted 2×20 mL ethyl acetate. Organic layers were combined, dried over anhydrous magnesium sulfate and concentrated in vacuo. Crude product was purified by flash column chromatography (15:1 to 15:1.5 hexanes-ethyl acetate) to give a solid, inseparable mixture of 31b and its corresponding regioisomer in 72% yield (1.63 g, 6.87 mmol). Spectral data are reported for the mixture. ¹H NMR (600 MHz, CDCl₃): δ 7.66 (d, 0.5H, J=7.8 Hz), 7.622 (d, 1H, J=7.8 Hz), 7.56 (d, 0.5H, J=7.2 Hz), 7.50-7.54 (m, 2H), 7.33-7.37 (m, 1.5H), 7.20-7.25 (m, 1.5H), 7.09-7.15 (m, 1H), 7.03-7.05 (dd, 1H, J=9.9, 2.4 Hz), 6.90-6.93 (td, 1H, J=9.3 Hz, 2.4 Hz, 1.8 Hz), 6.81-6.84 (dd, 0.5H, J=10.2, 7.8 Hz), 4.05 (s, 1.5H), 4.00 (s, 3H), 3.82 (s, 1H), 3.67 (s, 2H). ¹³C NMR (150 MHz, CDCl₃): δ 159.2 (d, J=235.5 Hz), 155.9 (d, J=244.5 Hz), 148.1, 147.5, 144.6 (d, J=4.5 Hz), 144.1, 143.9 (d, J=12.0 Hz), 141.5, (d, J=12.0 Hz), 134.9, 134.5, 126.2, 126.1, 125.3, 125.2, 124.5, 124.2, 121.0 (d, J=7.5 Hz), 120.4, 119.8, 119.1 (d, J=10.5 Hz), 117.3, 117.0, 116.8, 113.1 (d, J=24.0 Hz), 107.6 (d, J=25.5 Hz), 105.5 (d, J=4.5 Hz), 104.2 (d, J=19.5 Hz), 96.0 (d, J=25.5 Hz), 30.7, 30.5, 30.3, 29.5; ¹⁹F NMR (CD₃CD, 376 MHz): δ −120.0 (m), −122.2 (m); FTIR: cm⁻¹ 3056, 2892, 1608, 1573, 1530, 1486, 1187, 1099, 932, 756, 717.

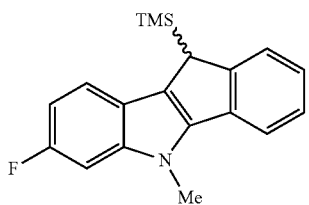

7-fluoro-5-methyl-10-(trimethylsilyl)-5,10-dihydroindeno[1,2-b]indole (32b)

Compound 31b (as a 2:1.1 mixture of regioisomers, 1.61 g, 6.79 mmol) was dissolved in anhydrous ether (46 mL) and the reaction mixture was immersed in a 25° C. water bath. n-BuLi (1.5M in hexanes, 5.25 mL, 7.87 mmol) was added dropwise via syringe pump over one hour. Following addition of base, the reaction mixture was stirred for one hour at 25° C. and then cooled to −78° C. TMSCl (1.81 mL, 14.25 mmol) was added rapidly via syringe and the resulting mixture was immediately warmed to 25° C. for 1.5 hours. The reaction mixture was diluted with 20 mL ether, filtered, and concentrated in vacuo to yield a dark green solid which was subsequently purified by multiple rounds of flash column chromatography (15:1 hexanes-ethyl acetate; 20:1 hexanes-ethyl acetate) to give the desired regioisomer in pure form and 2% yield. This low yield is a result of the similar polarities of regioisomers, which render separation a challenge. Spectral data are reported for the mixture that remained following purification of a small percentage of the desired regioisomer. As a result, product ratios do not represent those of the original product mixture. $^1$H NMR (600 MHz, CDCl$_3$): δ 7.74 (d, 1H, J=7.8 Hz), 7.71 (d, 0.5H, J=7.2 Hz), 7.51-7.55 (m, 2.5H), 7.31-7.34 (m, 1.5H), 7.21-7.24 (td, 1H, J=7.2, 1.2 Hz), 7.18-7.21 (td, 0.5H, J=7.2, 1.2 Hz), 7.17 (d, 1H, J=7.8 Hz), 7.12-7.14 (m, 1H), 7.05-7.07 (dd, 0.5H, J=9.9, 2.4 Hz), 6.87-6.91 (m, 0.5H), 6.80-6.83 (ddd, 1H, J=10.2, 8.4, 1.2 Hz), 4.10 (s, 3H), 4.05 (s, 1.5H), 3.93 (s, 1H), 3.75 (s, 0.5H), −0.04 (s, 4.5H), −0.98 (d, 9H, J=0.6 Hz); $^{13}$C NMR (150 MHz, CDCl$_3$): δ 159.3 (d, J=237.0 Hz), 156.0 (d, J=246 Hz), 150.4, 149.6, 144.3 (d, J=10.5 Hz), 143.6 (d, J=3.0 Hz), 143.0, 142.0 (d, J=12.0 Hz), 133.4, 132.7, 125.1, 124.9, 124.6, 124.6, 123.8, 123.52, 123.1, 121.3 (d, J=9.0 Hz), 120.6 (d, J=10.5 Hz), 120.3 (d, J=21.0 Hz), 117.6, 117.3, 113.0 (d, J=21.0 Hz), 107.4 (d, J=24.0 Hz), 105.6, 105.5, 104.4 (d, J=19.5 Hz), 96.2 (d, J=27.0 Hz), 37.3, 36.8, 31.5, 31.3, −2.42, −2.52 (d, J=3.0 Hz); $^{19}$F NMR (CD$_3$CD, 376 MHz): δ −117.1 (d, J=6.8 Hz), −120.5--120.1 (td, J=9.4, 3.8 Hz) FTIR: cm$^{-1}$ 3057, 2953, 1621, 1572, 1436, 1360, 1248, 1048, 839, 756, 727.

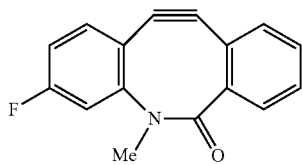

Fluoro-BARAC (120)

To a stirred solution of 32b (36.5 mg, 0.12 mmol) in dichloromethane (4 mL) and saturated aqueous NaHCO$_3$ (750 μL) at 0° C. was added m-CPBA (77%, 93 mg, 0.41 mmol) portionwise over 3 minutes. The reaction mixture was stirred at 0° C. for 2 hours and then warmed to room temperature over 15 minutes. The reaction was quenched via addition of 1N NaOH (5 mL) and the resulting aqueous layer was extracted 2×10 mL dichloromethane and 1×10 mL ethyl acetate. Organic layers were combined and washed 1×25 mL brine, dried over anhydrous magnesium sulfate, and concentrated in vacuo to yield an orange oil (33b) which was immediately brought on to the next step without purification.

To a solution of 33b (0.12 mmol assuming 100% yield from the previous step) in anhydrous THF (2 mL) at −78° C. was added potassium hexamethyldisilazide (0.5 M in toluene, 258 μL, 0.13 mmol) dropwise via syringe to give an orange solution which was stirred an additional 20 minutes at −78° C. Triflic anhydride (23 μL, 0.14 mmol) was then added, and the solution immediately turned yellow. The solution was stirred for 15 minutes at −78° C. prior to dilution with 5 mL anhydrous ether and addition of tetrabutyl ammonium fluoride (1M in THF, 1.2 mL). After an additional 45 minutes at −78° C., the reaction mixture was warmed to room temperature over 1 hour then quenched with saturated aqueous NaHCO$_3$ (10 mL). The aqueous layer was subsequently extracted 2×15 mL ethyl acetate and the organic layer was dried over anhydrous magnesium sulfate and concentrated in vacuo to yield a brown oil. Crude product was purified by flash column chromatography (15:1 hexanes-ethyl acetate) to give an orange solid in 29% yield (8.6 mg, 0.03 mmol). $^1$H NMR (400 MHz, CDCl$_3$): δ 7.59-7.61 (m, 1H), 7.45-7.47 (m, 2H), 7.36-7.41 (m, 3H), 7.08-7.13 (td, 1H, J=8.4, 2.8 Hz), 2.73 (s, 3H); $^{13}$C NMR (150 MHz, CDCl$_3$): δ 176.5, 162.9 (d, J=250.5 Hz), 158.0 (d, J=10.5 Hz), 149.2, 129.5, 128.7, 128.4 (d, J=9.6 Hz), 126.3, 125.5, 122.1, 118.4, 117.8 (d, J=22.8 Hz), 115.2 (d, J=21.9 Hz), 109.4, 107.6, 38.5; $^{19}$F NMR (CD$_3$CD, 376 MHz): δ −107.2 (dd, J=8.6, 6.0 Hz) FTIR: cm$^{-1}$ 2926, 1789, 1673, 1469, 1334, 1273, 1018; ESI-HRMS: Calcd. for C$_{16}$H$_{11}$FNO$^+$ [M+H]$^+$: 252.0819. found 252.0820.

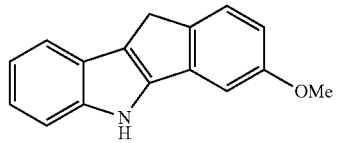

3-methoxy-5,10-dihydroindeno[1,2-b]indole (37a)

To a solution of phenyl hydrazine (1.21 mL, 1.33 g, 12.3 mmol) and 6-methoxy-1-indanone (2.01 g, 12.4 mmol) in ethanol (20 mL) was added glacial acetic acid (4 drops). The solution was stirred at reflux (85° C.) for 15 minutes and cooled to room temperature. Upon cooling, pale yellow crystals precipitated out of solution. Crystals were collected via vacuum filtration and dissolved in isopropanol (41 mL). Sulfuric acid (36 N, 1.39 mL) was added via syringe and the resulting solution was stirred at reflux (90° C.) for 18 hours—some precipitate formed over the course of the reaction. Upon cooling to room temperature, the solution was basified to pH 10 with aqueous sodium hydroxide (2% by mass) resulting in the formation of additional precipitate. The solid was collected by vacuum filtration to yield a brown solid which was subsequently dissolved in ethyl acetate (10 mL), diluted with H$_2$O (10 mL), and extracted 1×15 mL dichloromethane to remove excess water. The organic layers were combined, dried over anhydrous magnesium sulfate and concentrated to yield a brown solid in 61% crude yield (1.76 g, 7.50 mmol). Crude product was brought on to the next step without further purification. For purposes of characterization, the product was purified by flash column chromatography (20:1 hexanes—ethyl acetate). $^1$H NMR (600 MHz, CDCl$_3$): δ 8.28 (s, 1H), 7.64-7.65 (d, 1H, J=7.2 Hz), 7.42-7.44 (m, 2H), 7.16-7.21 (qd, 2H, J=7.2, 1.2 Hz), 7.03-7.04 (d, 1H, J=2.4 Hz), 6.77-6.78 (dd, 1H, J=7.8, 2.4 Hz), 3.89 (s, 3H), 3.68 (s, 2H); $^{13}$C NMR (150 MHz, CDCl$_3$): δ 159.0, 143.1, 140.6, 139.8, 136.1, 125.7, 124.8, 123.2, 121.8, 120.2, 119.0, 112.0, 109.9, 103.8, 55.6, 29.5. FTIR: cm$^{-1}$ 3390, 2934, 1609, 1577, 1528, 1467, 1274, 1251, 1037, 837, 745.: Calcd. for C$_{16}$H$_{14}$ON$^+$ [M+H]$^+$: 236.1070. found 263.1071.

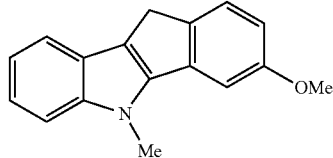

3-methoxy-5-methyl-5,10-dihydroindeno[1,2-b]indole (38a)

To a solution of 37a (592 mg, 2.52 mmol) in benzene (8 mL) was added aqueous sodium hydroxide (50% by mass, 4 mL), tetrabutylammonium iodide (82.7 mg, 0.22 mmol), and iodomethane (1.25 mL, 20.13 mmol). The reaction mixture was stirred vigorously at 40° C. for 16 hours and then at 55° C. for 2 additional hours. Upon cooling to room temperature, the mixture was diluted with benzene (20 mL) and H$_2$O (20 mL), and the aqueous layer was extracted 2×15 mL ethyl acetate. Organic layers were combined, washed 1×25 mL H$_2$O, dried over anhydrous magnesium sulfate and concentrated to yield a brown solid. Crude product was purified by flash column chromatography (20:1 to 10:1 hexanes-ethyl acetate) to give a tan brown solid in 87% yield (545 mg, 2.19 mmol). $^1$H NMR (600 MHz, CDCl$_3$): δ 7.65 (d, 1H, J=7.8 Hz), 7.42 (d, 1H, J=8.4 Hz), 7.38 (d, 1H, J=7.8 Hz), 7.25-7.27 (t, 1H, J=7.8 Hz), 7.18-7.21 (m, 2H), 6.78-6.79 (dd, 1H, J=8.4 Hz, 2.4 Hz), 3.99 (s, 3H), 3.92 (s, 3H), 3.63 (s, 2H). $^{13}$C NMR (150 MHz, CDCl$_3$): δ 158.74, 144.24, 141.77, 140.11, 136.45, 125.63, 123.98, 121.54, 121.16, 119.45, 118.95, 109.63, 109.01, 104.58, 55.50, 30.83, 29.19. FTIR: cm$^{-1}$ 3049, 2900, 1606, 1526, 1469, 1250, 1197, 1037, 742.

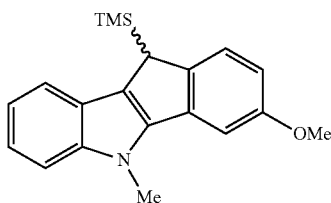

3-methoxy-5-methyl-10-(trimethylsilyl)-5,10-dihydroindeno[1,2-b]indole (39a)

A round bottom flask containing 38a (982 mg, 3.94 mmol) in dry ether (24 mL) was immersed in a 25° C. water bath. n-BuLi (1.5 M in THF, 3.05 mL, 4.57 mmol) was added via syringe pump over one hour, generating an orange solution. Following addition of base, the reaction mixture was stirred at 25° C. for an additional 45 minutes and then cooled to −78° C. TMSCl (1.05 mL, 8.27 mmol) was added rapidly via syringe, and the reaction mixture was stirred an additional 4 minutes at −78° C., then warmed to room temperature over 1.5 hours. The reaction was subsequently diluted with ether, filtered, and concentrated in vacuo. Crude product was purified by flash column chromatography (15:1 to 6:1 hexanes-ethyl acetate) to yield an inseparable mixture of 39a and its corresponding di-silylated indole (3:1 39a:side product) in 82% yield (1.04 g, 3.22 mmol, 61% yield desired product). 39a was brought on to the next step as a mixture. $^1$HNMR (600 MHz, CDCl$_3$): δ 7.79 (d, 1H, J=7.8 Hz), 7.52 (d, 1H, J=8.4 Hz), 7.47 (d, 1H, J=7.8 Hz), 7.39 (d, 1H, J=2.4 Hz), 7.34-7.37 (t, 1H, J=7.8 Hz), 7.26-7.30 (t, 1H, J=7.2 Hz), 6.90-6.92 (dd, 1H, J=8.4, 3.0 Hz), 4.09 (s, 3H), 3.99 (s, 3H), 3.75 (s, 1H), 0.01 (s, 9H); $^{13}$C NMR (150 MHz, CDCl$_3$): δ 157.7, 142.9, 142.2, 141.9, 134.5, 124.7, 124.3, 123.5, 120.9, 120.1, 118.9, 109.4, 109.0, 103.7, 55.4, 35.6, 30.8, −2.4. FTIR: cm$^{-1}$ 3049, 2951, 1617, 1520, 1464, 1246, 1202, 1042, 839, 741. EI-HRMS: Calcd. for C$_{20}$H$_{23}$NOSi$^+$ [M]$^+$: 321.1549. found 321.1548.

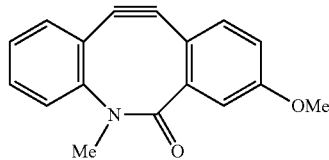

Methoxy-BARAC (123)

To a solution of 39a (105 mg, 0.33 mmol) in dichloromethane (12 mL) and saturated aqueous NaHCO$_3$ (1.9 mL) at 0° C. was added m-CPBA (77%, 263 mg, 1.17 mmol) portionwise over 3 minutes. The reaction mixture was stirred at 0° C. for 20 minutes and then warmed to room temperature over 40 minutes. The reaction was subsequently quenched via addition of 1N NaOH (15 mL) and the resulting aqueous layer was extracted 2×15 mL dichloromethane and 1×15 mL ethyl acetate. Organic layers were combined and washed 1× brine, dried over anhydrous magnesium sulfate, and concentrated in vacuo to yield an orange oil (40a), which solidified under high vacuum. Crude product was immediately brought on to the next step.

To a solution of 40a (0.33 mmol assuming 100% yield from the previous step) in anhydrous THF (4 mL) at −78° C. was added potassium hexamethyldisilazide (0.5 M in toluene, 722 µL, 0.36 mmol) dropwise via syringe to give an orange solution which was stirred an additional 12 minutes at −78° C. Triflic anhydride (65 µL, 0.39 mmol) was added and the reaction mixture immediately turned yellow. The solution was stirred for 15 minutes at −78° C. prior to dilution with 10 mL anhydrous ether and addition of tetrabutyl ammonium fluoride (1M in THF, 4.0 mL). The reaction mixture was warmed to room temperature over 2.5 hours then quenched with saturated aqueous NaHCO$_3$ (10 mL). The aqueous layer was subsequently extracted 2×15 mL ethyl acetate and the organic layer was dried over anhydrous magnesium sulfate and concentrated to yield an orange oil. The product was purified by flash column chromatography (10:1 to 5:1 hexanes—ethyl acetate) to yield an orange solid in 8% yield (6.7 mg, 0.03 mmol). The compound was later purified by HPLC. A 25 mg sample of 123 was dissolved in a 4 mL solution of acetonitrile (B) and water (A) (2:3 A:B). The compound was injected (2 mL×2 runs) onto a C18 column and eluted using a gradient of 35% B to 75% B over 15 minutes followed by a gradient of 10% B to 100% B over 5 minutes, isocratic elution at 100% B for 5 minutes and a gradient from 100% B to 35% B over 10 minutes. The product was collected at 19 minutes. Elution was monitored at 210 and 254 nM. $^1$H NMR (500 MHz, CDCl$_3$): δ 7.60 (d, 1H, J=8.0 Hz), 7.35-7.44 (m, 4H), 7.29 (d, 1H, J=8.5 Hz), 7.17 (d, 1H, J=2.5 Hz), 6.94-6.97 (dd, 1H, J=8.8, 2.5 Hz), 3.88 (s, 3H), 2.74 (s, 3H); $^{13}$C NMR (150 MHz, CDCl$_3$): δ 176.2, 160.1, 156.1, 150.9, 129.3, 129.2, 128.0, 127.7, 127.1, 122.7, 114.9, 113.9, 111.8, 109.5, 107.4, 55.6, 38.7. FTIR: cm$^{-1}$ 2928, 2246 1667, 1610, 1471, 1332, 1225, 1033. Calcd. for C$_{17}$H$_{14}$O$_2$N$^+$ [M+H]$^+$: 264.1019. found 264.1022.

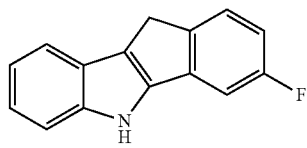

3-fluoro-5,10-dihydroindeno[1,2-b]indole (37b)

To a solution of phenyl hydrazine (1.32 mL, 13.32 mmol) and 6-fluoro-1-indanone (2.02 g, 13.46 mmol) in ethanol (7.6 mL) was added glacial acetic acid (3 drops). The solution was stirred at reflux (85° C.) for 17 minutes and cooled to room temperature. Upon cooling, white crystals precipitated out of solution. These crystals were collected by vacuum filtration and dissolved in isopropanol (23 mL). Sulfuric acid (36N, 1.51 mL) was added via syringe and the resulting solution was stirred at reflux (90° C.) for 18 hours and subsequently cooled to room temperature. The solution was then basified to pH 10 via addition of aqueous sodium hydroxide (2% by mass) resulting in the formation of precipitate. The solid was collected by vacuum filtration to yield 37b as a brown solid in 46% crude yield (1.38 g, 6.17 mmol). Crude product was brought on to the next step without further purification. For purposes of characterization, the product was purified by flash column chromatography (20:1 to 20:1.5 hexanes-ethyl acetate). $^1$H NMR (600 MHz, CDCl$_3$): δ 8.26 (s, 1H), 7.64-7.65 (d, 1H, J=7.8 Hz), 7.42-7.44 (m, 2H), 7.20-7.23 (td, 1H, J=7.2, 1.2 Hz), 7.16-7.19 (td, J=7.2, 1.2 Hz) 7.12-7.14 (dd, 1H, J=8.4, 2.4 Hz), 6.88-6.91 (m, 1H), 3.68 (s, 1H); $^{13}$C NMR (150 MHz, CDCl$_3$): δ 161.5-163.1 (d, J=242 Hz), 142.9 (d, J=2.4 Hz), 142.3 (d, J=2.9 Hz), 140.7, 136.5 (d, J=9.6 Hz), 126.0 (d, J=9.0 Hz), 124.5, 123.9, 122.3, 120.4, 119.2, 112.2, 111.0 (d, J=22.7 Hz), 104.8 (d, J=24.3 Hz), 29.8; FTIR: cm$^{-1}$ 3398, 1589, 1528, 1462, 1268, 1187, 744, 665. ESI-HRMS: Calcd. for C$_{15}$H$_{10}$FN$^+$ [M]$^+$: 223.0792. found 223.0792.

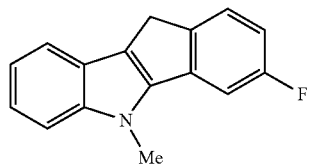

3-fluoro-5-methyl-5,10-dihydroindeno[1,2-b]indole (38b)

To a solution of 37b (1.38 g, 6.17 mmol) in benzene (12 mL) was added aqueous sodium hydroxide (33% by mass, 3.2 mL), tetrabutylammonium iodide (122.5 mg, 0.33 mmol), and iodomethane (3.04 mL, 48.78 mmol). The reaction mixture was stirred vigorously at 40° C. for 19 hours and then cooled to room temperature. The mixture was diluted with benzene (20 mL) and H$_2$O (20 mL), and the aqueous layer was extracted 2×15 mL ethyl acetate. Organic layers were combined, washed 1×25 mL H$_2$O, dried over anhydrous magnesium sulfate and concentrated to yield an orange/brown solid. Crude product was purified by flash column chromatography (10:1 to 4:1 hexanes-ethyl acetate) to give a 38b as a white solid in 71% yield (976 mg, 4.37 mmol). $^1$H NMR (600 MHz, CDCl$_3$): δ 7.64 (d, 1H, J=7.8 Hz), 7.39-7.41 (dd, 1H, J=7.8, 4.8 Hz), 7.49 (d, 1H, J=8.4 Hz), 7.25-7.30 (m, 2H), 7.20-7.23 (t, 1H, J=7.8 Hz), 6.90-6.94 (m, 1H), 3.88 (s, 3H), 3.55 (s, 2H). $^{13}$C NMR (150 MHz, CDCl$_3$): δ 162.1 (d, J=240 Hz), 143.5 (d, J=3 Hz), 143.1 (d, J=2.6 Hz), 141.8, 136.7 (d, J=9.5 Hz), 125.9 (d, J=9.2 Hz), 123.8, 122.1, 121.6, 119.6, 119.1, 110.6 (d, J=22.5 Hz), 109.7, 104.9 (d, J=24.6 Hz), 30.7 (d, J=1.7 Hz), 29.3.

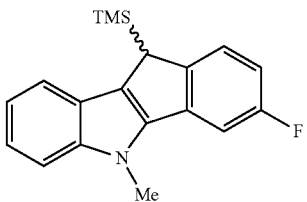

3-fluoro-5-methyl-10-(trimethylsilyl)-5,10-dihydroindeno[1,2-b]indole (39b)

A round bottom flask containing 38b (976 mg, 7.37 mmol) in dry ether (30 mL) was immersed in a 25° C. water bath. n-BuLi (1.5 M in THF, 3.38 mL, 5.07 mmol) was added via syringe pump over one hour, generating a dark red solution. Following addition of base, the reaction mixture was stirred at 25° C. for an additional 50 minutes and then cooled to −78° C. TMSCl (1.17 mL, 9.18 mmol) was added rapidly via syringe, and the reaction mixture was stirred an additional 5 minutes at −78° C., then warmed to room temperature over 1.5 hours. The reaction was subsequently diluted with ether, filtered, and concentrated in vacuo. Crude product was purified by flash column chromatography (15:1 hexanes-ethyl acetate) to yield an inseparable mixture of 39b and its corresponding di-silylated indole (6.8:1 ratio 39b:side product) in 80% yield (1.08 g, 3.48 mmol, 70% yield desired product). 39b was brought on to the next step as a mixture with the di-silylated indole. $^1$H NMR (400 MHz, CDCl$_3$): δ 7.67 (d, J=8.0 Hz), 7.34-7.46 (m, 2H), 7.25-7.29 (t, 1H, J=7.2 Hz), 7.15-7.19 (t, 1H, J=7.2 Hz), 6.90-6.95 (td, 1H, J=8.8, 2.4 Hz), 4.06 (s, 3H), 4.74 (s, 1H), −0.01 (s, 9H).

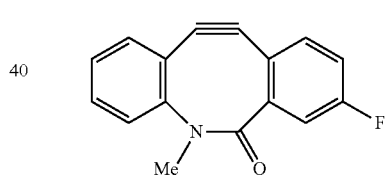

Fluoro-BARAC (124)

To a solution of 39b (535 mg, 1.73 mmol) in dichloromethane (60 mL) and saturated aqueous NaHCO$_3$ (11 mL) at 0° C. was added m-CPBA (77%, 1.05 g, 3.15 mmol) portionwise over 4 minutes. The reaction mixture was stirred at 0° C. for 25 minutes and then warmed to room temperature over 50 minutes. The reaction was subsequently quenched via addition of 1N NaOH (20 mL) and the resulting aqueous layer was extracted 2×20 mL dichloromethane and 1×20 mL ethyl acetate. Organic layers were combined and washed 1× brine, dried over anhydrous magnesium sulfate, and concentrated in vacuo to yield a dark orange oil. Crude product (40b) was immediately brought on to the next step without further purification.

To a solution of 40b (1.73 mmol assuming 100% yield from the previous step) in anhydrous THF (20 mL) at −78° C. was added potassium hexamethyldisilazide (0.5 M in toluene, 3.78 mL, 1.89 mmol) dropwise via syringe to give a red/brown solution which was stirred an additional 25 minutes at −78° C. Triflic anhydride (343 μL, 2.04 mmol) was then added, and the solution immediately turned yellow. The solution was stirred for 10 minutes at −78° C. prior to dilution with 15 mL anhydrous ether and addition of tetrabutyl ammonium fluoride (1M in THF, 15.0 mL). The reaction mixture was warmed to room temperature over 50 minutes then quenched with saturated aqueous NaHCO$_3$ (50 mL). The aqueous layer was subsequently extracted 1×30 mL ethyl acetate and the organic layer was dried over anhydrous magnesium sulfate and concentrated to yield a brown oil. The product was purified by flash column chromatography. Three attempts at purification were required to achieve the desired purity (15:1 to 5:1 hexanes-ethyl acetate; 15:1 hexanes-ethyl acetate; 5:1:5 hexanes-acetone-toluene) 124 was isolated as an orange solid in 4% yield (17 mg, 0.07 mmol).

The compound was later purified by HPLC. A 10 mg sample of 124 was dissolved in a 2.5 mL solution of acetonitrile(B) and water(A) (2:3 A:B). The compound was injected onto a C18 column and eluted using a gradient of 35% B to 75% B over 15 minutes followed by a gradient of 10% B to 100% B over 5 minutes, isocratic elution at 100% B for 5 minutes and a gradient from 100% B to 35% B over 10 minutes. The product was collected at 18.5 minutes. Elution was monitored at 210 and 254 nM. $^1$H NMR (600 MHz, CDCl$_3$): δ 7.61 (d, 1H, J=7.8 Hz), 7.45-7.48 (td, 1H, J=7.2, 1.8 Hz), 7.39-7.42 (m, 2H), 7.33-7.37 (m, 2H), 7.14-7.17 (td, 1H, J=7.8 Hz, 2.4 Hz), 2.74 (s, 3H). $^{13}$C NMR (150 MHz, CDCl$_3$): δ 175.0, 162.4 (d, J=252 Hz), 156.3, 151.0 (d, J=6 Hz), 129.8, 129.9, 128.2 (d, J=8.7 Hz), 128.2, 127.4, 122.1, 118.3 (d, J=3.5 Hz), 116.5 (d, J=22.5 Hz), 113.8 (d, J=24.2 Hz), 108.7, 108.1, 38.6; FTIR: cm$^{-1}$ 2923, 1666, 1467, 1428, 1330, 1209.: Calcd. for C$_{17}$H$_{14}$O$_2$N$^+$ [M+H]$^+$: 252.0819. found 252.0821.

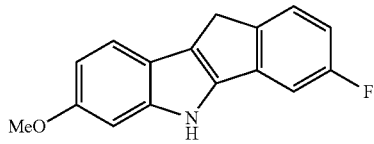

3-fluoro-7-methoxy-5,10-dihydroindeno[1,2-b]indole (55)

To a solution of 3-methoxyphenyl hydrazine (2.01 g, 11.53 mmol) and 6-fluoro-1-indanone (1.73 g, 11.50 mmol) in ethanol (22 mL) was added glacial acetic acid (3 drops). The solution was stirred at reflux (85° C.) for 15 minutes and cooled to room temperature. Ethanol was removed in vacuo and the resulting brown oil was dissolved in isopropanol (39 mL). Sulfuric acid (36N, 1.28 mL) was added via syringe and the solution was stirred at reflux (90° C.) for 15 hours and subsequently cooled to room temperature. The reaction was then basified to pH 10 via addition of aqueous sodium hydroxide (2% by mass) resulting in the formation of precipitate. The solid was collected by vacuum filtration to yield a brown residue, which was subsequently dissolved in 20 mL dichloromethane, and diluted with 15 mL H$_2$O. The organic layer was partitioned and the aqueous layer was extracted 1×15 mL ethyl acetate and 1×15 mL dichloromethane. Organic layers were pooled, dried over anhydrous magnesium sulfate, and concentrated to yield 55 as a mixture of regioisomers (3:1 55:undesired). Crude product was brought on to the next step without further purification. $^1$H NMR (600 MHz, CDCl$_3$): δ 8.17 (s, 1H), 7.50 (d, J=8.4 Hz), 7.38-7.41 (dd, 1H, J=8.4, 5.4 Hz), 7.05-7.07 (dd, 1H, J=9.0, 2.4 Hz), 6.927 (d, 1H, J=2.4 Hz), 6.83-6.86 (m, 2H), 3.87 (s, 3H), 3.63 (s, 2H). $^{13}$C NMR (150 MHz, CDCl$_3$): δ 162.4 (d, J=241.5 Hz), 156.6, 142.4 (d, J=2.4 Hz), 141.7, 141.3 (d, J=3.0 Hz), 136.8 (d, J=9.6 Hz), 125.8 (d, J=9.2 Hz), 124.0, 119.7, 119.1, 110.3 (d, J=22.7 Hz), 110.0, 104.2 (d, J=24.5 Hz), 96.1, 60.4, 29.8. $^{19}$F NMR (CD$_3$CD, 376 MHz): δ −113.9 (m), −115.9 (m); FTIR: cm$^{-1}$ 3381, 1614, 1531, 1464, 1270, 1188, 1157, 859, 814. ESI-HRMS: Calcd. for C$_{16}$H$_{12}$FNO$^+$ [M]$^+$: 253.0897. found 253.0894.

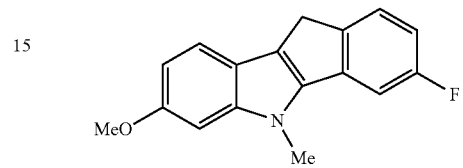

3-fluoro-7-methoxy-5-methyl-5,10-dihydroindeno[1,2-b]indole (56)

To a solution of 55 (as a 3:1 mixture of regioisomers, 1.26 g, 4.98 mmol) in benzene (25 mL) was added aqueous sodium hydroxide (50% by mass, 3 mL), tetrabutylammonium iodide (152.1 mg, 0.41 mmol), and iodomethane (2.48 mL, 39.8 mmol). The reaction mixture was stirred vigorously at 40° C. for 17 hours and then cooled to room temperature over 3.5 hours. The mixture was diluted with benzene (20 mL) and H$_2$O (20 mL), and the aqueous layer was extracted 2×20 mL ethyl acetate. Organic layers were combined, washed 1×25 mL H$_2$O, dried over anhydrous magnesium sulfate and concentrated. Crude product was purified by flash column chromatography (40:1 hexanes-ethyl acetate) to give 56 as one regioisomer in 71% yield (713 mg, 2.67 mmol, % yield based on amount of 55 in starting material mixture). $^1$H NMR (600 MHz, CDCl$_3$): δ 7.49 (d, 1H, J=9 Hz), 7.37-7.39 (dd, 1H, J=7.8 Hz, 4.8 Hz), 7.21-7.23 (dd, 1H, J=9.3 Hz, 1.8 Hz), 6.82-6.86 (m, 3H), 3.92 (s, 3H), 3.91 (s, 3H). $^{13}$C NMR (150 MHz, CDCl$_3$): δ 162.2 (d, J=240 Hz), 156.4, 142.8, 142.7 (d, J=3 Hz), 142.6 (d, J=3 Hz), 137.1 (d, J=9.5 Hz), 125.8 (d, J=9.2 Hz), 122.4, 119.8, 118.4, 109.9 (d, J=22.5 Hz), 109.3, 104.3 (d, J=24.8 Hz), 93.7, 55.7, 30.9, 29.5; $^{19}$F NMR (CD$_3$CD, 376 MHz): δ −116.0 (q, J=14.1, 9.4 Hz); FTIR: cm$^{-1}$ 1611, 1592, 1530, 1460, 1380, 1258, 1221, 1161. EI-HRMS: Calcd. for C$_{17}$H$_{14}$FNO$^+$ [M]$^+$: 267.1059. found 267.1062.

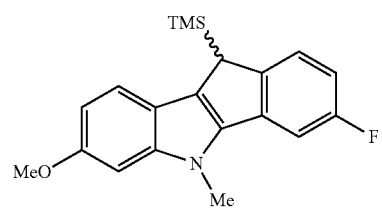

3-fluoro-7-methoxy-5-methyl-10-(trimethylsilyl)-5,10-dihydroindeno [1,2-b]indole (57)

A round bottom flask containing 56 (201 mg, 0.75 mmol) in dry ether (6 mL) was immersed in a 25° C. water bath.

n-BuLi (1.5 M in THF, 602 μL, 0.90 mmol) was added via syringe pump over one hour, generating an orange solution. Following addition of base, the reaction mixture was stirred at 25° C. for an additional 1.5 hours and then cooled to −78° C. TMSCl (200 μL, 1.58 mmol) was added rapidly via syringe, and the reaction mixture was stirred an additional 5 minutes at −78° C., then warmed to room temperature over 3.5 hours. The reaction was subsequently diluted with ether, filtered, and concentrated in vacuo. Crude product was purified by flash column chromatography (20:1 hexanes-ethyl acetate) to yield 57 as a solid in 62% yield (159 mg, 0.47 mmol). $^1$H NMR (600 MHz, CDCl$_3$): δ 7.54 (d, 1H, J=8.4 Hz), 7.39-7.41 (dd, 1H, J=8.4, 4.8 Hz), 7.33-7.35 (dd, 1H, J=9, 2.4 Hz), 6.83-6.89 (m, 3H), 3.98 (s, 3H), 3.93 (s, 3H), −0.02 (s, 9H). $^{13}$C NMR (150 MHz, CDCl$_3$): δ 61.4 (d, J=238.5 Hz), 156.2, 144.5 (d, J=2.0), 143.0, 141.5 (d, J=3 Hz), 134.8 (d, J=9.5 Hz), 125.4, 124.79 (d, J=9.15 Hz), 120.9, 118.0, 109.4 (d, J=22.8 Hz), 108.6, 103.9 (d, J=24.3 Hz), 93.5, 5.6, 36.3, 31.0, −2.5; $^{19}$F NMR (CD$_3$CD, 376 MHz): δ −117.6 (m); FTIR: cm$^{-1}$ 2952, 1608, 1523, 1372, 1223, 1163, 1107, 1042, 939, 841.

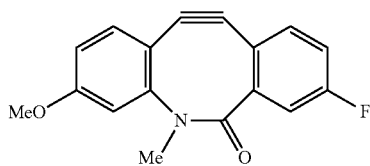

Methoxyfluoro-BARAC (41)

To a solution of 57 (109 mg, 0.32 mmol) in dichloromethane (11.5 mL) and saturated aqueous NaHCO$_3$ (1.9 mL) at 0° C. was added m-CPBA (77%, 264 mg, 1.18 mmol) portionwise over 4 minutes. The reaction mixture was stirred at 0° C. for 30 minutes and then warmed to room temperature over 20 minutes. The reaction was subsequently quenched via addition of 10 mL 1N NaOH and the resulting aqueous layer was extracted 2×15 mL dichloromethane and 1×15 mL ethyl acetate. Organic layers were combined and washed 1× brine, dried over anhydrous magnesium sulfate, and concentrated in vacuo to yield an orange oil. Crude product was immediately brought on to the next step without further purification.

The oil (0.322 mmol assuming 100% yield from the previous step) was dissolved in anhydrous THF (3.8 mL) at −78° C. and potassium hexamethyldisilazide (0.5 M in toluene, 708 μL, 0.35 mmol) was added dropwise via syringe to give a red solution which was stirred an additional 25 minutes at −78° C. Triflic anhydride (65 μL, 0.39 mmol) was then added, and the reaction mixture immediately turned yellow. The solution was stirred for 20 minutes at −78° C. prior to dilution with 18 mL anhydrous ether and addition of tetrabutyl ammonium fluoride (1M in THF, 5.0 mL). The reaction mixture was warmed to room temperature over 3 hours and subsequently quenched with saturated aqueous NaHCO$_3$ (30 mL). The aqueous layer was extracted 2×20 mL ethyl acetate and the organic layer was dried over anhydrous magnesium sulfate and concentrated to yield a brown oil. The product was purified by flash column chromatography (20:1 to 5:1 hexanes-ethyl acetate), and 41 was isolated as an orange solid in 17% yield (16 mg, 0.06 mmol). $^1$H NMR (600 MHz, CDCl$_3$): δ 7.30-7.34 (m, 3H), 7.20 (d, 1H, J=2.4 Hz), 7.12-7.15 (dt, 1H, J=8.4, 2.4 Hz), 6.90-6.92 (dd, 1H, J=8.4, 2.4 Hz), 3.87 (s, 3H), 2.74 (s, 3H); $^{13}$C NMR (150 MHz, CDCl$_3$): δ 175.2, 162.1 (d, J=250.5 Hz), 161.0, 157.8, 150.5 (d, J=7.5 Hz), 128.1, 127.8 (d, J=7.5 Hz), 118.7 (d, J=3.0 Hz), 116.4 (d, J=22.5 Hz), 115.9, 113.8, 113.6, 113.6, 108.9, 106.9, 55.6, 38.6; $^{19}$F NMR (CD$_3$CD, 376 MHz): δ −108.9 (q, J=13.5, 8.3 Hz); FTIR: cm$^{-1}$ 2939, 2246, 1669, 1603, 1471, 1321, 1291, 1026. FAB-HRMS: Calcd. for C$_{17}$H$_{13}$FNO$_2$$^+$ [M+H]$^+$: 282.0925. found 282.0928.

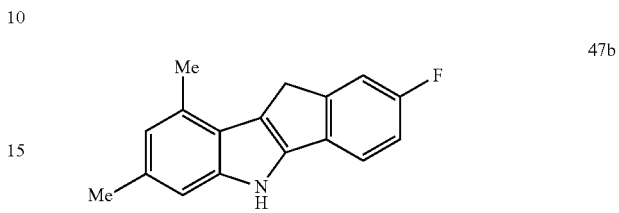

3-fluoro-7,9-dimethyl-5,10-dihydroindeno[1,2-b]indole (47b)

To a solution of 3,5-dimethylphenylhydrazine (2.54 g, 14.7 mmol) and 5-fluoro-1-indanone (2.21 g, 14.7 mmol) in ethanol (24 mL) was added glacial acetic acid (3 drops). The solution was stirred at reflux (85° C.) for 15 minutes and cooled to room temperature. Ethanol was removed in vacuo and the resulting orange solid was dissolved in isopropanol (24 mL). Sulfuric acid (36N, 1.65 mL) was added via syringe and the mixture was stirred at reflux (90° C.) for 17 hours and subsequently cooled to room temperature. The solution was basified to pH 10 via addition of aqueous sodium hydroxide (2% by mass) resulting in the formation of a precipitate. The solid was collected by vacuum filtration to yield 47b in 76% crude yield (2.80 g, 11.2 mmol). Crude product was brought on to the next step without further purification. $^1$H NMR (400 MHz, CDCl$_3$): δ 8.12 (s, 1H), 7.32-7.35 (dd, 1H, J=8.2, 5.2 Hz), 0.24-7.26 (m, 1H), 7.01-7.05 (m, 2H), 6.79 (s, 1H), 3.83 (s, 2H), 2.60 (s, 3H), 2.44 (s, 3H); $^{13}$C NMR (150 MHz, CDCl$_3$): δ 160.7 (d, J=361.5), 150.0 (d, J=12.0 Hz), 140.9, 140.6, 131.8, 131.2, 128.9, 122.6, 122.3, 121.6 (d, J=4.5 Hz), 117.2 (d, J=13.5 Hz), 113.4 (d, J=25.5 Hz), 113.1 (d, J=25.5 Hz), 109.6, 31.7 (d, J=3.0 Hz), 21.8, 19.3; $^{19}$F NMR (CD$_3$CD, 376 MHz): δ −117.9 (m).

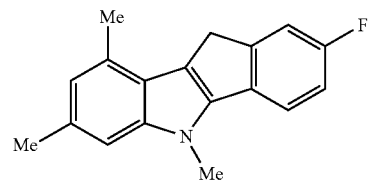

2-fluoro-5,7,9-trimethyl-5,10-dihydroindeno[1,2-b]indole (48b)

To a solution of 47b (2.74 g, 10.9 mmol) in benzene (59 mL) was added aqueous sodium hydroxide (50% by mass, 5.9 mL), tetrabutylammonium iodide (289 mg, 0.78 mmol), and iodomethane (5.42 mL, 87.1 mmol). The reaction mixture was stirred vigorously at 40° C. for 16 hours and then cooled to room temperature. The mixture was diluted with benzene (20 mL) and H$_2$O (20 mL), and the aqueous layer was extracted 2×20 mL ethyl acetate. Organic layers were combined, washed 1×25 mL H₂O, dried over anhydrous magnesium sulfate and concentrated to yield a brown solid. Crude product was purified by flash column chromatography (15:1 hexanes-ethyl acetate followed by a second column 40:1 to 26:1 hexanes-ethyl acetate) to give 48b in 39% yield (1.12 g, 4.24 mmol). $^1$H NMR (400 MHz, CDCl₃): δ 7.51-7.53 (dd, 1H, J=8.2, 5.2 Hz), 7.237-7.260 (m, 1H), 7.99-7.06 (td, 1H, J=9.2, 2.4 Hz), 6.99 (s, 1H), 6.78 (s, 1H), 3.97 (s, 3H), 3.80 (s, 2H), 2.60 (s, 3H), 2.46 (s, 3H); $^{13}$C NMR (150 MHz, CDCl₃): δ 160.5 (d, J=361.5 Hz), 150.4 (d, J=13.5 Hz), 142.42, 141.72, 131.6 (d, J=3.0 Hz), 131.3, 129.0, 121.9, 121.6, 119.5 (d, J=4.5 Hz), 117.1 (d, J=13.5 Hz), 113.2 (d, J=34.5 Hz), 113.5 (d, J=34.1 Hz), 107.1, 31.2 (d, J=2.9 Hz), 30.8, 21.8, 19.0; $^{19}$F NMR (CD₃CD, 376 MHz): δ −118.0 (m); FTIR: cm$^{-1}$ 3011, 2917, 1588, 1527, 1449, 1417, 1360, 1267, 1212.

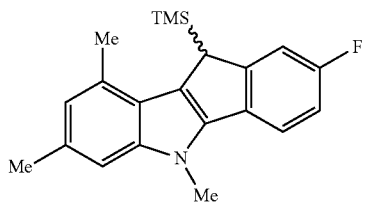

49b 3-fluoro-5,7,9-trimethyl-10-(trimethylsilyl)-5,10-dihydroindeno[1,2-b]indole (49b)

A round bottom flask containing 48b (1.11 g, 4.17 mmol) in dry ether (27 mL) was immersed in a 25° C. water bath. n-BuLi (1.5 M in THF, 3.33 mL, 5.00 mmol) was added via syringe pump over one hour, generating a brown solution. Following addition of base, the reaction mixture was stirred at 25° C. for an additional 30 minutes and then cooled to −78° C. TMSCl (1.11 mL, 8.76 mmol) was added rapidly via syringe and the solution was subsequently warmed to room temperature. The reaction was diluted with ether, filtered, and concentrated in vacuo. Crude product was purified by flash column chromatography (20:1 hexanes-ethyl acetate followed by a second column 40:1 to 26:1 hexanes—ethyl acetate) to yield 49b as an orange solid in 78% yield (1.09 g, 3.24 mmol). $^1$H NMR (400 MHz, CDCl₃): δ 7.57-7.60 (dd, 1H, J=8.4, 5.2 Hz), 7.19-7.22 (dd, 1H, J=9.6, 2.4 Hz), 7.00-7.04 (m, 2H), 6.78 (s, 1H), 4.01 (s, 3H), 3.97 (s, 1H), 2.61 (s, 3H), 2.49 (s, 3H), −0.15 (s, 9H); $^{13}$C NMR (150 MHz, CDCl₃): δ 159.7 (d, J=289.5 Hz), 152.2 (d, J=10.1 Hz), 142.1, 141.2, 131.17, 129.4, 129.0, 122.7, 121.9, 121.7, 117.2 (d, J=10.5 Hz), 111.7 (d, J=27.9 Hz), 111.6 (d, J=29.7 Hz), 107.0, 38.2, 31.0, 21.8, 20.1, −2.2; $^{19}$F NMR (CD₃CD, 376 MHz): δ −118.6 (m) FTIR: cm$^{-1}$ 2952, 1583, 1445, 1357, 1248, 1198, 1037, 838. EI-HRMS: Calcd. for C₂₁H₂₄FNSi⁺ [M]⁺: 337.1662. found 337.1664.

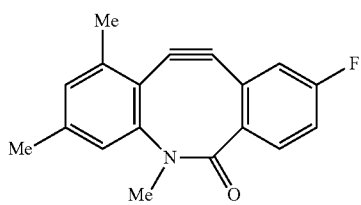

44

Dimethylfluoro-BARAC (44)

To a solution of 49b (97 mg, 0.29 mmol) in dichloromethane (10 mL) and saturated aqueous NaHCO₃ (1.7 mL) at 0° C. was added m-CPBA (77%, 247 mg, 1.10 mmol) portionwise over 3 minutes. The reaction mixture was stirred at 0° C. for 20 minutes and then warmed to room temperature over 1.5 hours. The reaction was subsequently quenched via addition of 1N NaOH (10 mL) and the resulting aqueous layer was extracted 2×10 mL dichloromethane and 1×10 mL ethyl acetate. Organic layers were combined and washed 1× brine, dried over anhydrous magnesium sulfate, and concentrated in vacuo to yield an orange oil (50b). Crude product was immediately brought on to the next step without further purification.

To a solution of 50b (0.29 mmol assuming 100% yield from the previous step) in anhydrous THF (3.4 mL) at −78° C. was added potassium hexamethyldisilazide (0.5 M in toluene, 740 μL, 0.32 mmol) dropwise via syringe to give an orange solution which was stirred an additional 1 hour at −78° C. Triflic anhydride (58 μL, 0.35 mmol) was then added, and the reaction mixture immediately turned bright yellow. The solution was stirred for 30 minutes at −78° C. prior to dilution with 10 mL anhydrous ether and addition of tetrabutyl ammonium fluoride (1M in THF, 4.5 mL). The reaction mixture was warmed to room temperature over 40 minutes and subsequently quenched with saturated aqueous NaHCO₃ (30 mL). The aqueous layer was extracted 2×20 mL ethyl acetate and the organic layer was dried over anhydrous magnesium sulfate and concentrated to yield a brown oil. The product was purified by flash column chromatography (20:1 to 2:1 hexanes-ethyl acetate followed by a second column 20:1 hexanes-ethyl acetate) to yield 44 as a white solid in 5% yield (3.8 mg, 0.01 mmol). The compound was later purified by HPLC. A sample of 44 was dissolved in a solution of acetonitrile(B) and water(A) (2:3 A:B). The compound was injected onto a C18 column and eluted using a gradient of 35% B to 75% B over 15 minutes followed by a gradient of 10% B to 100% B over 5 minutes, isocratic elution at 100% B for 5 minutes and a gradient from 100% B to 35% B over 10 minutes. Elution was monitored at 210 and 254 nM. $^1$H NMR (600 MHz, CDCl₃): δ 7.54-7.56 (dd, 1H, J=8.4, 5.4 Hz), 7.27 (s, 1H), 7.10-7.13 (td, 1H, J=8.4, 3.0 Hz), 7.03-7.05 (m, 2H), 2.71 (s, 3H), 2.42 (s, 3H), 2.39 (s, 3H). $^{13}$C NMR (150 MHz, CDCl₃): δ 176.07, 162.78, 156.71, 145.01 (d, J=3 Hz), 140.51, 137.70, 129.93, 127.45, 127.014 (d, J=9.3 Hz), 124.88 (d, J=10.35 Hz), 118.84, 115.33 (d, J=22.4 Hz), 113.55 (d, J=23.0 Hz), 110.30, 108.87 (d, J=3.9 Hz), 38.65, 21.52, 21.28. $^{19}$F NMR (CD₃CD, 376 MHz): δ −109.4 (m).

Cell Culture Procedures

Jurkat (human T-cell lymphoma) and CHO (Chinese hamster ovarian) cells were maintained in RPMI-1640 (Jurkat, Invitrogen Life Technologies, Inc.) or F12 (CHO, HyClone Laboratory) media supplemented with 10% fetal calf serum (FCS), penicillin (100 units/mL), and streptomycin (0.1 mg/mL) in a 5% CO₂ water-saturated atmosphere. The cells were maintained at densities between 1×10⁵ and 1.6×10⁶ cells/mL.

Reaction Rate of BARAC with Benzyl Azide

The reactivity of BARAC (compound 15) was studied using benzyl azide as a model substrate. The second-order rate constant in acetonitrile at room temperature (rt) was 0.96 M$^{-1}$s$^{-1}$ (see FIG. 1), over 12-fold higher than the rate constant for DIFO under identical conditions and over 450 times higher than for an unactivated cyclooctyne. The half-life for the reaction of equimolar amounts of BARAC with benzyl azide at 10 mM was about 45 s at rt. The half-life of the potential background reaction of 2 mM BARAC with 5 mM glutathione in $CD_3CN:D_2O$ (1:2) was 24 h at rt.

The reaction of BARAC (compound 15) and benzyl azide was monitored by $^1H$ NMR for 30 min. at 25° C. BARAC and benzyl azide were separately dissolved in $CD_3CN$ and mixed together in a 1:1 ratio at concentrations at 10 mM. A 2:1 ratio was used to determine the exact ratio of reagents based on remaining starting material upon completion of the reaction. The percent conversion was calculated by the disappearance of BARAC and benzyl azide relative to the formation of product as determined by integration. No products other than the two regioisomers of addition were apparent by $^1H$ NMR. The triazole isomers were produced in a ~1:1 ratio. The second-order rate constant was determined by plotting 1/[compound 15] versus time. The plot was fit to a linear regression and the slope corresponds to the second-order rate constant. Shown in FIG. 1 are data from four replicate experiments. The four lines had an average of $0.96 \pm 0.04$ $M^{-1}s^{-1}$.

Figure 13:
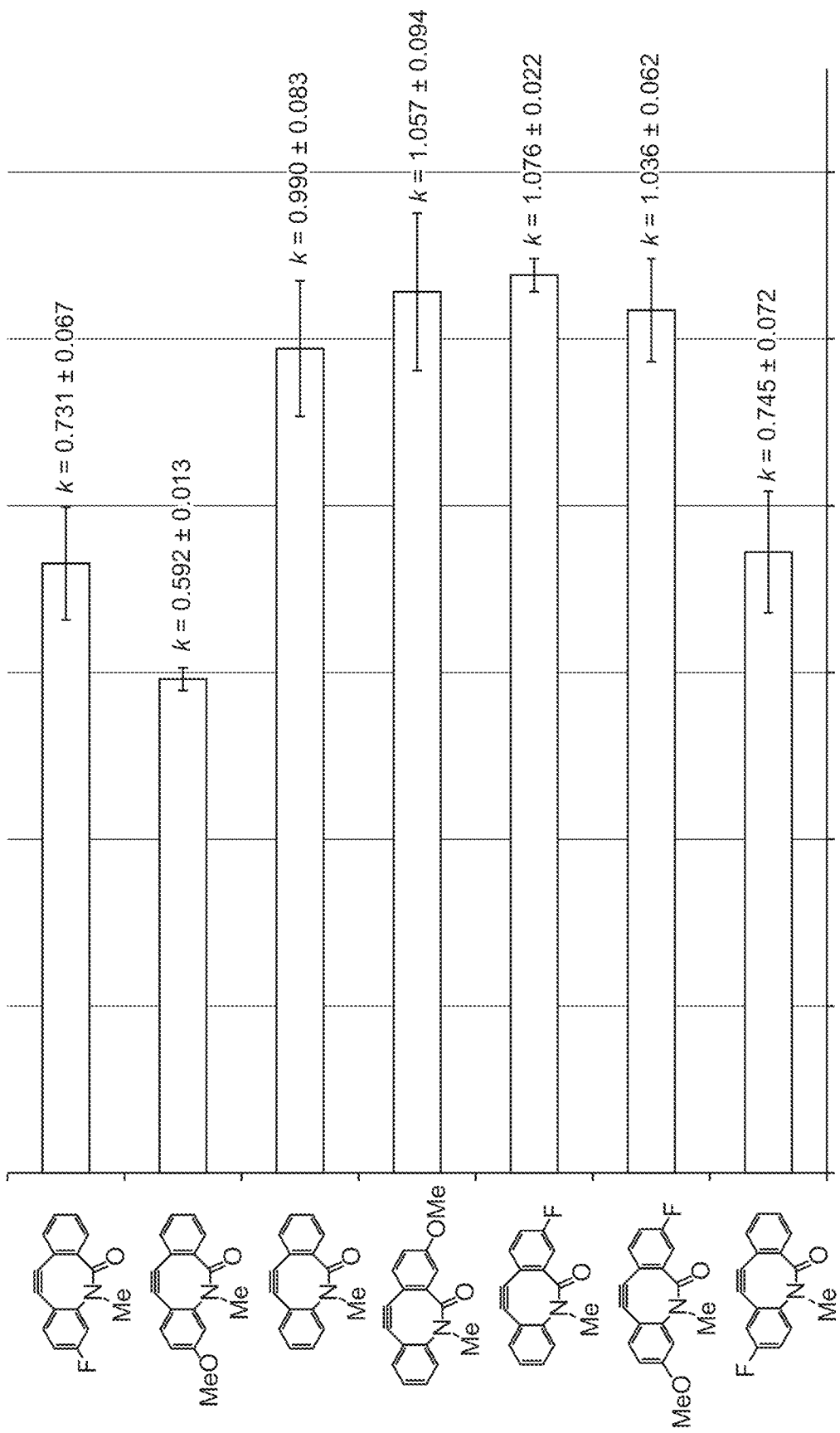
FIG. 13 shows second order rate constants for the cycloaddition of BARAC analogs with benzyl azide.

Second order rate constants for the cycloaddition of BARAC analogs with benzyl azide were determined using the method described above. All reactions were performed in $CD_3CN$ (5 mM) at room temperature. The results are shown in FIG. 13. All rate constants have units of $M^{-1}s^{-1}$ Cell Surface Azide Labeling and Detection BARAC's performance in live cell labeling experiments was studied. Using a carbamate linkage, BARAC (compound 15) was conjugated to biotin, giving BARAC-biotin (compound 16), or to fluorescein, giving BARAC-Fluor (compound 17; see FIG. 8(a) and Scheme 2). Azides were introduced into the cell surface glycans using a strategy as reported by Laughlin, S. T. and Bertozzi, C. R. Laughlin, S. T.; Bertozzi, C. R. *Proc. Natl. Acad. Sci. U.S.A.*, (2009), 106, 12-17. Cultured Jurkat cells were treated with peracetylated N-azidoacetyl mannosamine ($Ac_4ManNAz$) to introduce the corresponding azido sialic acids (SiaNAz) into their cell-surface glycoproteins and lipids. The cells were labeled with BARAC-biotin at a concentration of 1 µM for 1 h. Staining with fluorescein isothiocyanate (FITC-avidin) and flow cytometry analysis produced the data shown in FIG. 8(b).

Jurkat cells were incubated in untreated media or media containing 25 µM $Ac_4ManNAz$. After 3 d, the cells were twice concentrated (500×g, 3 min, 4° C.) and resuspended in 10 mL FACS buffer (PBS containing 1% FCS, 2×10 mL) and cells (approx 350,000 per a well) were placed in a 96 well V-bottom plate. The cells were concentrated by centrifugation (2500×g, 3 min, 4° C.), resuspended in 200 µL cold FACS buffer, and again concentrated by centrifugation (2500×g, 3 min, 4° C.). The cells were then reacted for 1 h (unless otherwise noted) at rt with the desired reagent (no reagent, BARAC-biotin, DIFO-biotin as reported by Baskin, et al., or DIBO-biotin as reported by Ning, et al.). Baskin, J. M.; Prescher, J. A.; Laughlin, S.T.; Agard, N. J.; Chang, P. V.; Miller, I. A.; Lo, A.; Codelli, J. A.; Bertozzi, C. R. *Proc. Natl. Acad. Sci. U.S.A.*, (2007), 104, 16793-16797; Ning, X.; Guo, J.; Wolfert, M. A.; Boons, G.-J. *Angew. Chem. Int. Ed.*, (2008), 47, 2253-2255. After 1 h, the cells were thrice concentrated by centrifugation (2500×g, 3 min, 4° C.) and resuspended in 200 µL cold FACS buffer. Following and additional concentration by centrifugation (2500×g, 3 min, 4° C.), cells were resuspended in FACS buffer (100 µL) containing FITC-avidin (1:200 dilution of 1 mg/mL stock, Sigma-Aldrich) and incubated in the dark at 4° C. for 15 min. Following the incubation, cells were concentrated by centrifugation, resuspended in 200 µL cold FACS buffer, concentrated by centrifugation, and another FITC-avidin incubation was performed. After the second FITC-avidin labeling, the cells were thrice concentrated by centrifugation (2500×g, 3 min, 4° C.) and resuspended in 200 µL cold FACS buffer. The cells were then diluted to 400 µL for flow cytometry analysis. Flow cytometry was performed on a BD Biosciences FACSCalibur flow cytometer equipped with a 488-nm argon laser. All flow cytometry experiments were performed with three replicate samples.

Figure 3:
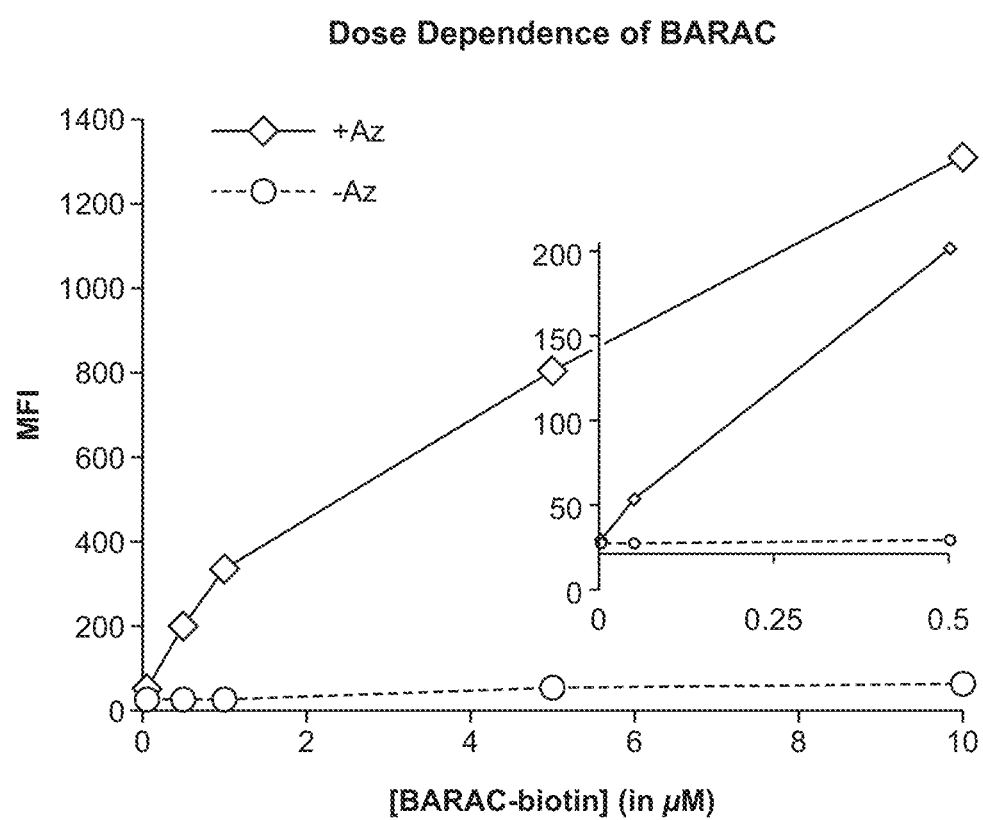
FIG. 3 shows a graph of the dose dependence of BARAC-biotin (compound 16) according to embodiments of the present disclosure.
Figure 4:
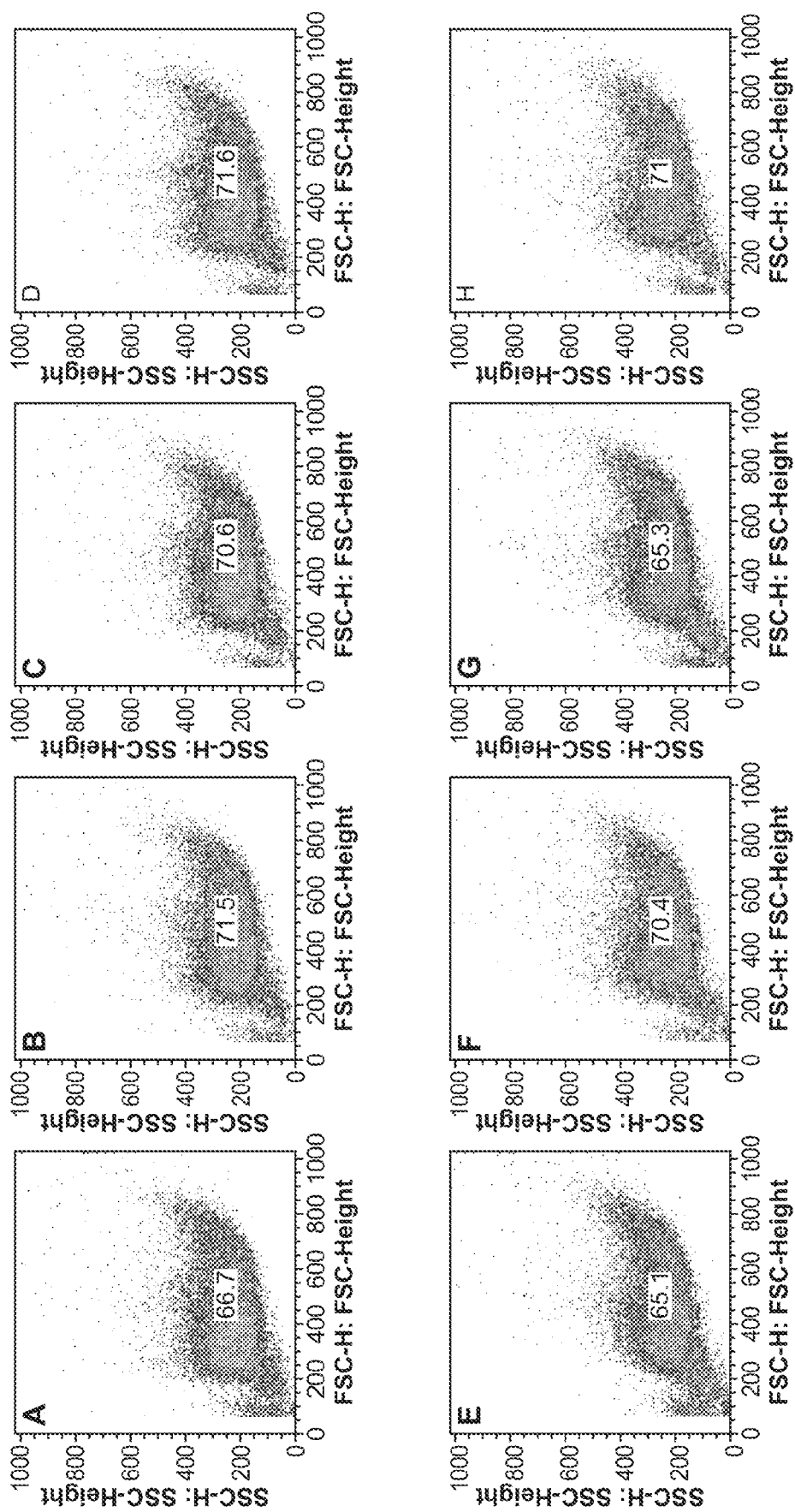
FIG. 4($a$)-($h$) shows forward-scatter and side-scatter plots for cell labeling experiments according to embodiments of the present disclosure.

The cells showed robust azide-specific labeling with no significant background labeling compared to cells treated with FITC-avidin alone (see FIG. 3). Even at a concentration of 50 nM, BARAC-biotin still showed significant cell labeling in 1 h (FIG. 3).

Figure 8:
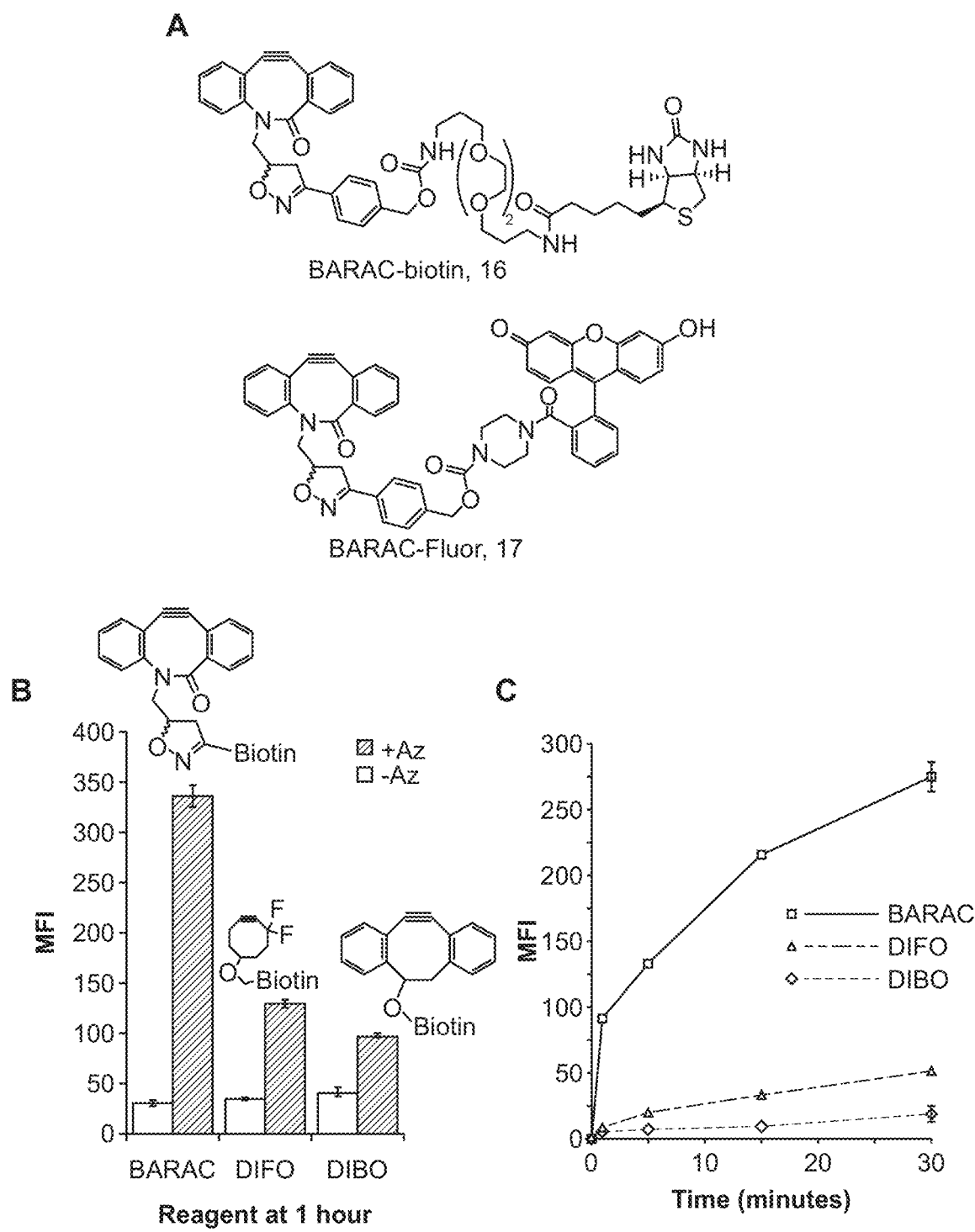
FIG. 8($a$)-($c$) show: structures of BARAC-biotin (compound 16) and BARAC-Fluor (compound 17) (FIG. 8A); and incorporation of the compounds into living cells (FIG. 8B and FIG. 8C).

For comparative purposes, similar experiments were performed using DIFO-biotin and DIBO-biotin (see FIG. 8(b)). BARAC-biotin showed more labeling than DIFO-biotin and DIBO-biotin after 1 h. To quantify the differences in reaction kinetics among the reagents in the context of cell surface labeling, cell surface fluorescence was measured at various time points during a 30-min incubation with the cyclooctynes (FIG. 8(c)). After 1 min, BARAC-biotin gave a 10-fold higher signal than either DIFO-biotin or DIBO-biotin, consistent with BARAC's ~12-fold higher rate constant. The high level of reactivity of BARAC-biotin was not accompanied by any cytotoxicity compared to cells treated with no cyclooctyne reagent (see FIG. 5).

Cell-Surface Labeling of Azido Glycans on CHO Cells and Imaging by Fluorescence Microscopy BARAC-Fluor (compound 17) was evaluated as a reagent for direct fluorescence imaging of live Chinese hamster ovary (CHO) cells. CHO cells grown either in the presence or absence of 50 µM $Ac_4ManNAz$ were treated with 5 M BARAC-Fluor (compound 17) for 5 min at rt, washed and then imaged (FIG. 9(a)-(h)). The azide-labeled CHO cells showed significant cell surface fluorescence.

CHO cells were incubated for 3 days in medium containing 50 µM $Ac_4ManNAz$ in an eight-well LabTek II chambered cover glass (Nunc). The medium was poured off, and the cells were washed three times with 200 µl of FACS buffer. The cells then were treated with a solution of BARAC-Fluor, diluted from a 1 mM stock solution in DMSO, in FACS buffer for 5 minutes at 5 µM at room temperature. The cells were also treated with Hoechst 33342 dye to stain the nucleus (1:1,000 dilution in medium of a 1 mg/ml stock solution in DMSO) as soon as possible after the addition of BARAC-Fluor. The cells washed four times with 200 µl of FACS buffer, and imaged at room temperature.

For the no-wash experiment the cells were treated as before, but were incubated in a 250 nM solution of BARAC-Fluor in FACS-buffer. After 25 minutes at room temperature Hoechst 33342 dye (1:1,000 dilution in medium of a 1 mg/ml stock solution in DMSO) was added. After an additional 5 minutes, the cells were imaged without washing away excess reagent. The +Az were imaged first to ensure that the 30-minute time point was as accurate as possible. The labeled cells showed significant labeling above the background (FIG. 9(i)-(p)).

FIGURE LEGENDS

FIG. 1 shows a graph of the rate of reaction between BARAC (compound 15) and benzyl azide over time according to embodiments of the present disclosure. The reaction of BARAC (compound 15) and 2-azido-N-isopropylacetamide was monitored by $^1H$ NMR for 30 min. at 25° C. BARAC and the azidoacetamide were separately dissolved in $CD_3CN$ and mixed together in a 1:1 ratio at concentrations at close to 10 mM (9.2 mM). Hexamethyldisilane (approx 0.3 equiv) was used as an internal standard. The percent conversion was calculated by the ratio between the formation of products and hexamethyldisilane as determined by integration. No products other than the regioisomers of addition were apparent by $^1$H NMR. The ratio of triazole isomers is complicated by rotamers. The second-order rate constant was determined by plotting 1/[compound 15] versus time. The plot was fit to a linear regression and the slope corresponds to the second-order rate constant. Shown are data from three replicate experiments. The three lines had an average of 0.64±0.06 $M^{-1}s^{-1}$.

Figure 2:
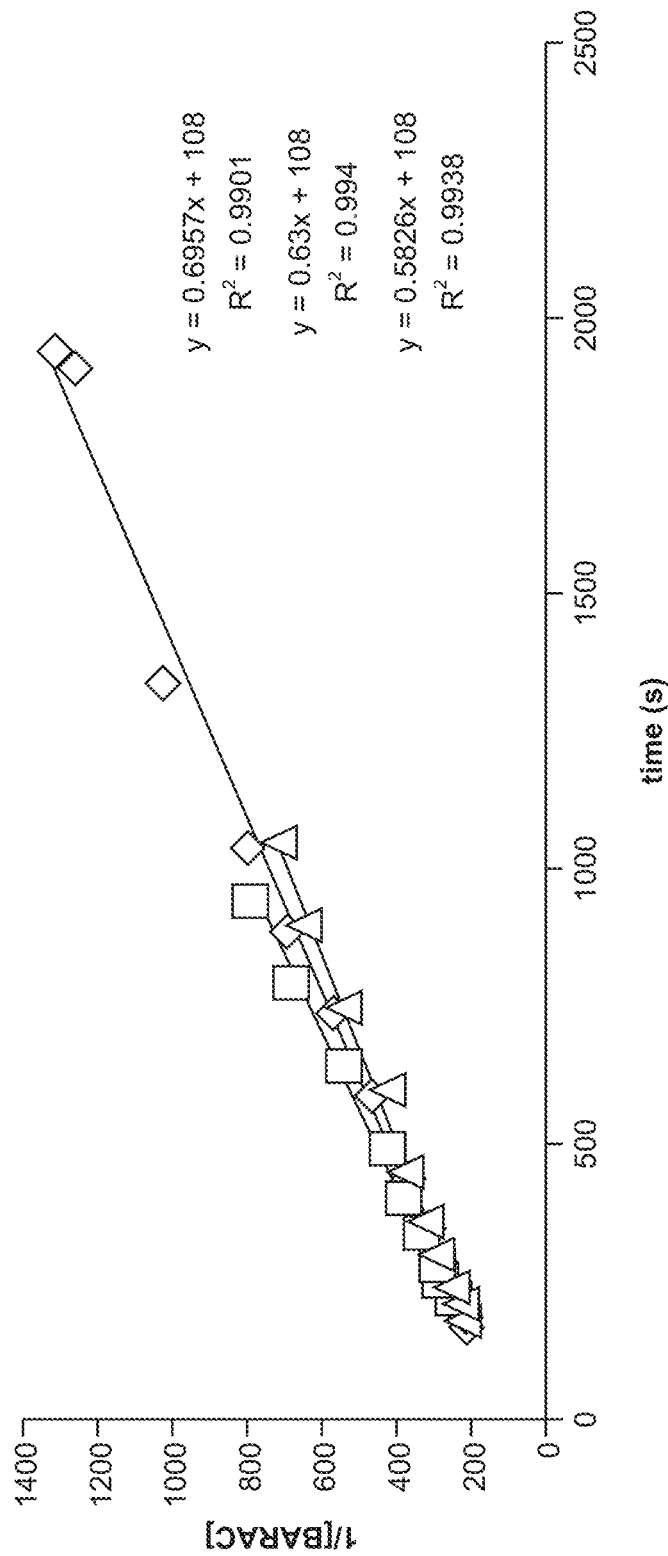
FIG. 2 shows a graph of the rate of reaction between BARAC (compound 15) and 2-azido-N-isopropylacetamide over time according to embodiments of the present disclosure.

FIG. 2 shows a graph of the rate of reaction between BARAC (compound 15) and 2-azido-N-isopropylacetamide over time according to embodiments of the present disclosure. The reaction of BARAC (compound 15) and 2-azido-N-isopropylacetamide was monitored by $^1$H NMR for 30 min. at 25° C. BARAC and the azidoacetamide were separately dissolved in $CD_3CN$ and mixed together in a 1:1 ratio at concentrations at close to 10 mM (9.2 mM). Hexamethyldisilane (approx 0.3 equiv) was used as an internal standard. The percent conversion was calculated by the ratio between the formation of products and hexamethyldisilane as determined by integration. No products other than the regioisomers of addition were apparent by $^1$H NMR. The ratio of triazole isomers is complicated by rotamers. The second-order rate constant was determined by plotting 1/[compound 15] versus time. The plot was fit to a linear regression and the slope corresponds to the second-order rate constant. Shown are data from three replicate experiments. The three lines had an average of 0.64±0.06 $M^{-1}s^{-1}$.

FIG. 3 shows a graph of the dose dependence of BARAC-biotin (compound 16) according to embodiments of the present disclosure. Cell-surface glycan labeling with BARAC-biotin (compound 16). Jurkat cells were incubated in the presence or absence of 25 μM $Ac_4ManNAz$ for 3 d. Cells were reacted with no reagent (FACS buffer), BARAC-biotin (compound 16) at varying concentrations in FACS buffer for 1 hour at 25° C., incubated with FITC-avidin, and analyzed by flow cytometry. The error bars represent standard deviations from three replicate samples (but are too small to see drawn to scale). MFI=mean fluorescence intensity and has arbitrary units (Au).

FIG. 4(a)-(h) shows forward-scatter and side-scatter plots for cell labeling experiments according to embodiments of the present disclosure. Representative forward-scatter (x-axis, FSC-H) and side-scatter (y-axis, SSC-H) plots for the experiment shown in FIG. 8(b). Jurkat cells were treated without (FIG. 4(a)-(d)) or with (FIG. 4(e)-(h)) 25 μM $Ac_4ManNAz$ for 3 d and then treated with no reagent ((FIGS. 4(a) and (e)) 1 μM DIBO-biotin (FIGS. 4(b) and (f)), 1 M BARAC-biotin (FIGS. 4(c) and (g)), or 1 μM DIFO-biotin (FIGS. 4(d) and (h)) followed by FITC-avidin.

Figure 5:
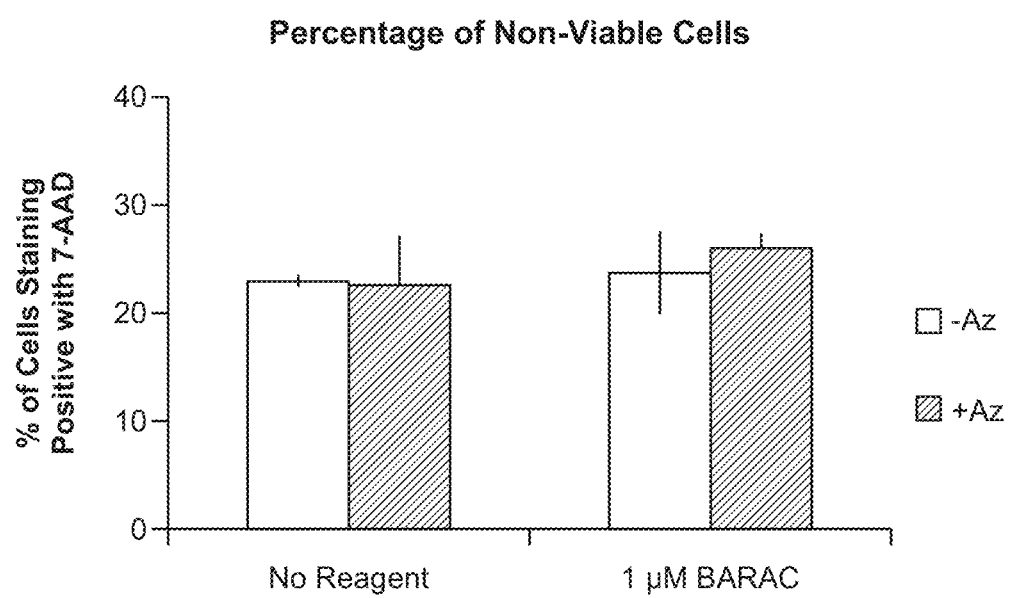
FIG. 5 shows a graph of a cytotoxicity analysis of BARAC-biotin (compound 16) according to embodiments of the present disclosure.
Figure 6:
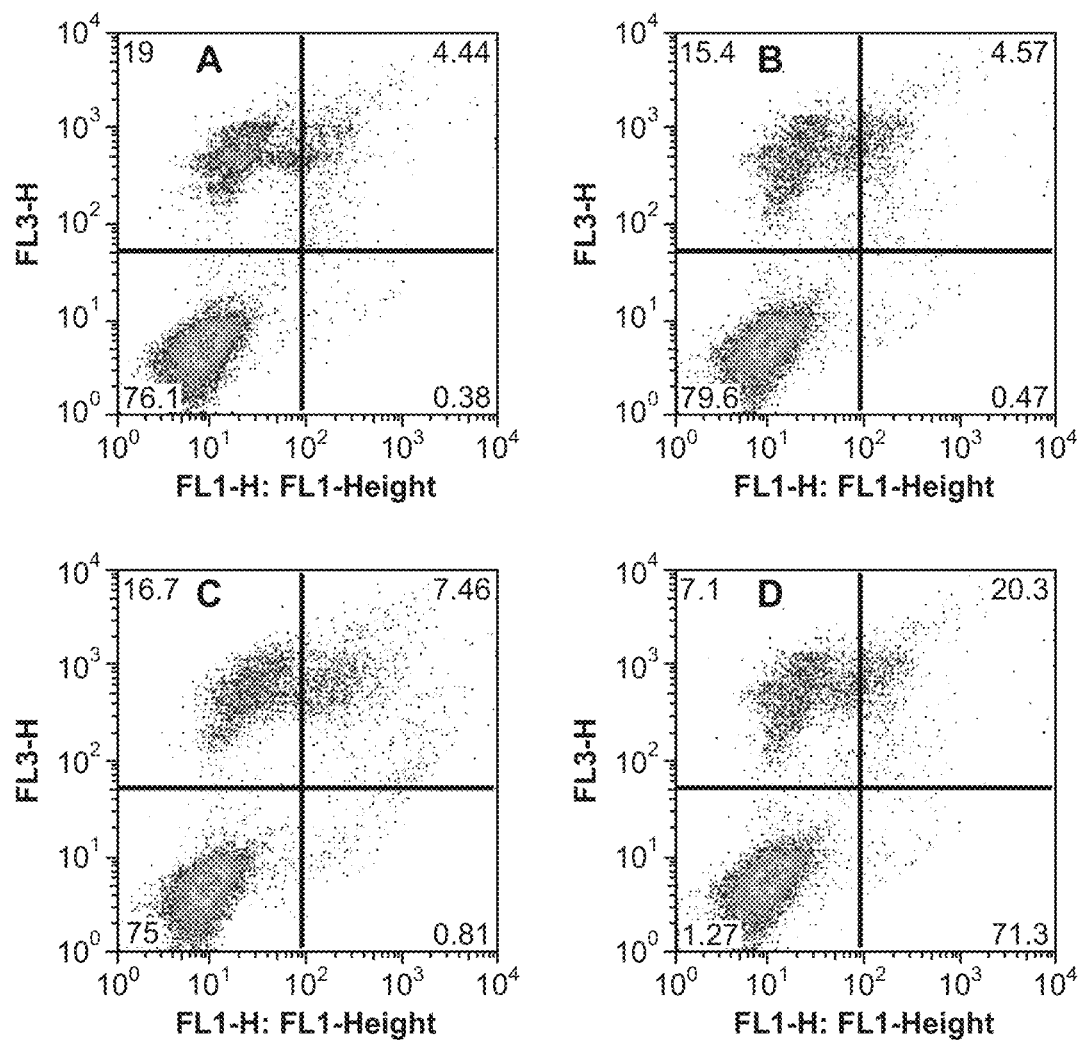
FIG. 6($a$)-($d$) shows FL3 vs. FL1 scatter plots for the flow cytometry experiments described in FIG. 5 according to embodiments of the present disclosure.

FIG. 5 shows a graph of a cytotoxicity analysis of BARAC-biotin (compound 16) according to embodiments of the present disclosure. Jurkat cells were incubated in the presence (+Az, black bar) or absence (−Az, gray bar) of $Ac_4ManNAz$ for 3 d. Cells were reacted with no reagent (FACS buffer) or BARAC-biotin (compound 16) (1 μM compound 16 in FACS buffer) for 1 h at 25° C., incubated with FITC-avidin, and washed. Prior to flow cytometry analysis, half the cells were treated with 7-amino-actinomycin D (7-AAD) following the procedure reported at http://www.bdbiosciences.com/external_files/pm/doc/tds/cell_bio/live/web_enabled/68981E_559925.pdf. The samples were diluted and analyzed by flow cytometry. The error bars represent standard deviations from three replicate samples.

FIG. 6(a)-(d) shows FL3 vs. FL1 scatter plots for the flow cytometry experiments described in FIG. 5 according to embodiments of the present disclosure. In all plots, the x-axis indicates the degree of cell-surface glycan labeling as measured by FITC fluorescence (FL1). For the plots shown if FIG. 6(a)-(d), the y-axis represents the degree of 7-AAD (FL3, cell viability marker). Jurkat cells were treated with ((FIGS. 6(c) and (d)) or without (FIGS. 6(a) and (b)) 25 μM $Ac_4ManNAz$ for 3 d. The cells were then treated with no reagent (FIGS. 6(a) and (c)) or 1 M BARAC-biotin (FIGS. 6(b) and (d)) for 1 h at 25° C. followed by FITC-avidin. Cells were then treated with 7-AAD and analyzed by flow cytometry.

FIG. 7 shows analytical HPLC graphs of purified BARAC-Fluor according to embodiments of the present disclosure. Method: 40% to 50% B from 1-2 min, 50% to 75% B from 2-9 min, 75% to 95% B from 9-12 min. Solvent A: water+0.1% trifluoroacetic acid; solvent B: acetonitrile+0.1% trifluoroacetic acid. Agilent Zorbax SB-C18 column (5 μM, 2.1×150 mm).

FIG. 8(a) shows structures of BARAC-biotin (compound 16) and BARAC-Fluor (compound 17) according to embodiments of the present disclosure. FIG. 8(b) and FIG. 8(c) show flow cytometry plots for live cell labeling experiments with BARAC-biotin according to embodiments of the present disclosure. Jurkat cells were incubated with (+Az) or without (−Az) 25 M $Ac_4ManNAz$ for 3 days. The cells were labeled with 1 μM cyclooctyne-biotin for various times and then treated with FITC-avidin. Cyclooctyne-biotin probes used were DIBO-biotin, BARAC-biotin, or DIFO-biotin. The degree of labeling was quantified by flow cytometry. The level of fluorescence was reported in mean fluorescence intensity (MFI, arbitrary unit). Error bars represent the standard deviation of three replicate experiments. FIG. 8(b) shows a graph of a comparison of the efficiencies of labeling of different cyclooctyne reagents after 1 h. FIG. 8(c) shows a graph of time-dependent labeling of cyclooctyne-biotin probes. MFI reported as difference between signal of cells +Az and signal of cells −Az.

Figure 9:
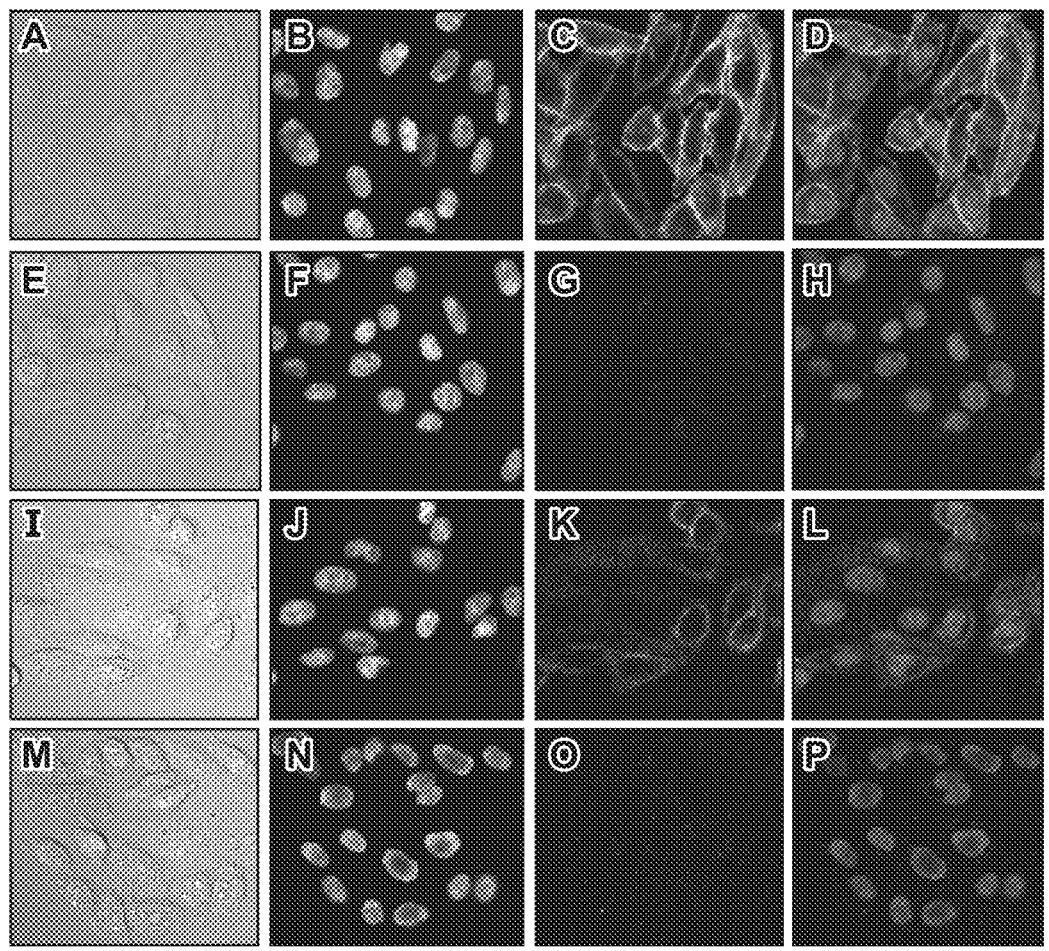
FIG. 9($a$)-($p$) shows fluorescence imaging of azide-labeled glycans on live cells using BARAC-Fluor (compound 17) according to embodiments of the present disclosure.

FIG. 9(a)-(p) shows fluorescence imaging of azide-labeled glycans on live cells using BARAC-Fluor (compound 17) according to embodiments of the present disclosure. CHO cells were incubated with (FIG. 9(a)-(d) and FIG. 9(i)-(l)) or without (FIG. 9(e)-(h) and FIG. 9(m)-(p)) 50 μM $Ac_4ManNAz$ for 3 days. The cells were subsequently labeled with 5 μM BARAC-Fluor and Hoechst-33342 for 5 min and then washed and imaged (FIG. 9(a)-(h)). The cells were subsequently labeled with 250 nM BARAC-Fluor for 30 min and Hoechst-33342 and then imaged without washing (FIG. 9(i)-(p)). Channels shown are DIC (FIG. 9(a), (e), (i), and (m)), DAPI (FIG. 9(b), (f), (j), and (n)), FITC (FIG. 9 (c), (g), (k), and (o)) and DAPI/FITC merge ((FIG. 9(d), (h), (l), and (p)).

Figure 10:
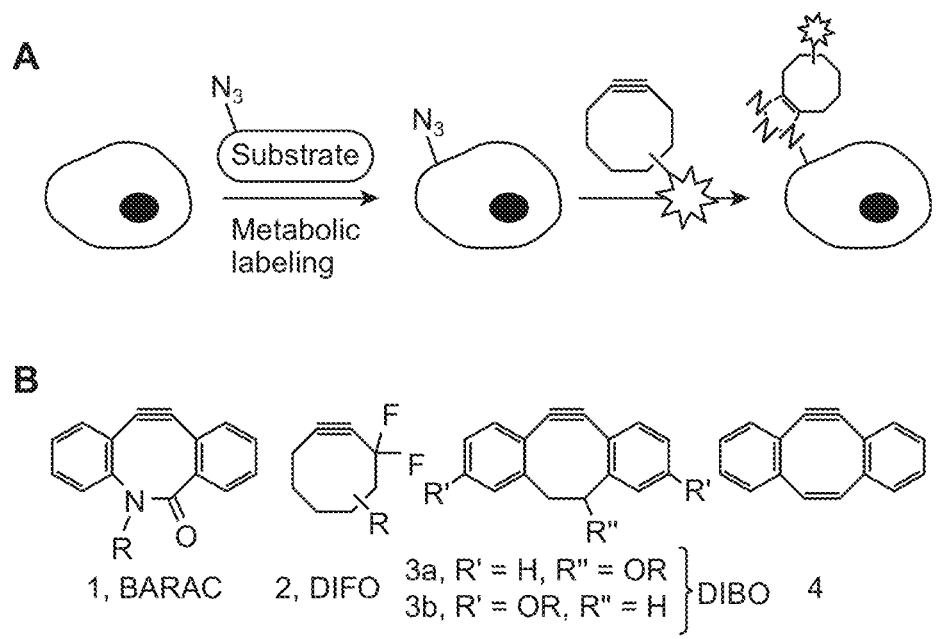
FIGS. 10($a$) and ($b$) show: a scheme of a bioorthogonal reaction of cyclooctyne probes with azide-labeled biomolecules that allows their interrogation in cell-based systems according to embodiments of the present disclosure (FIG. 10A); and the structures of compounds 1-4 (FIG. 10B).

FIG. 10(a) shows a scheme of a bioorthogonal reaction of cyclooctyne probes with azide-labeled biomolecules that allows their interrogation in cell-based systems according to embodiments of the present disclosure. In FIG. 10(a), Cells are treated with azide-functionalized metabolic substrates. The azides are then detected with a cyclooctyne-functionalized probe. FIG. 10(b) shows cyclooctynes designed for fast Cu-free click chemistry (compounds 1-3) and reactivity studies (compound 4) according to embodiments of the present disclosure.

Figure 11:
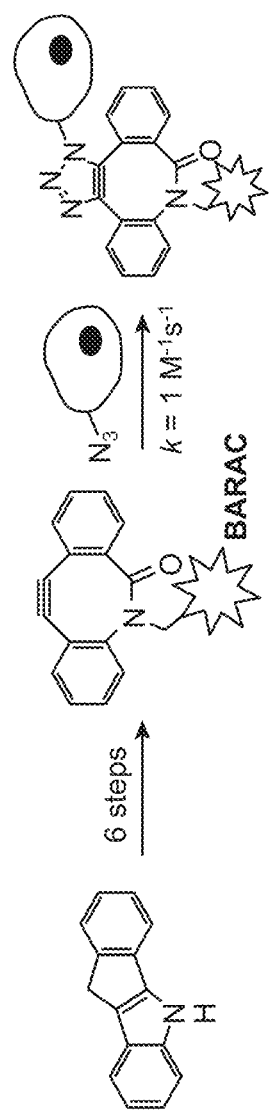
FIG. 11 shows a scheme for the 6-step synthesis of a BARAC derivative from compound 9 and the labeling of an azide-labeled biomolecule with the BARAC derivative.

FIG. 11 shows a scheme for the 6-step synthesis of a BARAC derivative from compound 9 and the labeling of an azide-labeled biomolecule with the BARAC derivative.

FIG. 12 shows the crystal structure of BARAC.

FIG. 13 shows second order rate constants for the cycloaddition of BARAC analogs with benzyl azide.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method for labeling a target molecule comprising an azide, the method comprising:

reacting an azide of a target molecule with a modified cycloalkyne compound of the formula:

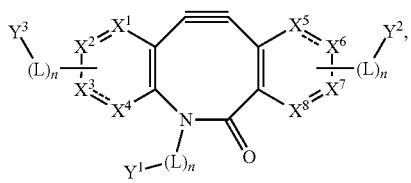

Formula IV wherein $X^1$-$X^8$ are each independently selected from carbon and nitrogen;

each L is a divalent moiety independently selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, carboxamido, $C_1$ to $C_7$ acyloxy, urethanylene, sulfonyl, sulfonamido, —O—, —S—, —NH—, and substituted amino; wherein substituents of the substituted divalent moieties are selected from carboxy, amino, halo, hydroxy, nitro, cyano, trifluoromethyl, $C_1$ to $C_7$ alkyl, $C_1$ to $C_7$ alkoxy, $C_1$ to $C_7$ acyloxy, carboxamide, carboxymethyl, and hydroxymethyl; and wherein the substituted and unsubstituted heteroarylene and heterocyclene divalent moieties are five or six-membered rings having 1 to 4 heteroatoms independently selected from oxygen, nitrogen and sulfur ring atoms;

each n is a number independently selected from zero to 40; and $Y^1$-$Y^3$ are independently selected from H; a group selected from a carboxyl, an amino, an alkoxycarbonyl, a RSC(O)—, a sulfonyl halide, a hydroxyl, an alkoxy, an —SH, an N-succinimidyl ester, an isothiocyanate, an iodoacetamide, a maleimidyl, a hydrazinyl, a hydrazide, a halogen, a cyano, a diazo, an azide, a guanidinyl, a sulfone, an epoxide, a diazirine, an alkenyl, an alkynyl, a phosphine, a silane and an alkylsulfonic acid; and a molecule of interest selected from a detectable label, a toxin, a peptide, a drug, a member of a specific binding pair, an epitope tag and a strained azacycloalkynone group, wherein said reacting produces a conjugate between the azide of the target molecule and the modified cycloalkyne.

2. The method of claim 1, wherein the target molecule is a sugar.

3. The method of claim 2, wherein the sugar is a substrate of sialic acid biosynthesis.

4. The method of claim 2, wherein the sugar is mannosamine or acetylated mannosamine.

5. The method of claim 1, wherein the target molecule is an amino acid.

6. The method of claim 1, wherein said reacting is performed in aqueous conditions.

7. The method of claim 1, wherein said reacting is performed under physiological conditions.

8. The method of claim 1, wherein the target molecule comprising the azide is expressed on a cell surface.

9. The method of claim 1, wherein the method further comprises detecting the conjugate.

10. A method for labeling a cellular component, the method comprising:

introducing an azide moiety into a cellular component, thereby generating an azide-modified cellular component; and contacting a cell comprising the azide-modified cellular component with a reactive partner comprising a modified cycloalkyne compound of the formula:

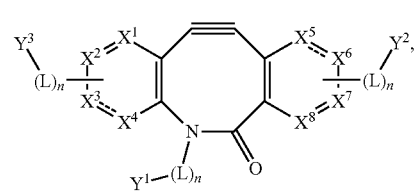

Formula IV wherein $X^1$-$X^8$ are each independently selected from carbon and nitrogen;

each L is a divalent moiety independently selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, carboxamido, $C_1$ to $C_7$ acyloxy, urethanylene, sulfonyl, sulfonamido, —O—, —S—, —NH—, and substituted amino; wherein substituents of the substituted divalent moieties are selected from carboxy, amino, halo, hydroxy, nitro, cyano, trifluoromethyl, $C_1$ to $C_7$ alkyl, $C_1$ to $C_7$ alkoxy, $C_1$ to $C_7$ acyloxy, carboxamide, carboxymethyl, and hydroxymethyl; and wherein the substituted and unsubstituted heteroarylene and heterocyclene divalent moieties are five or six-membered rings having 1 to 4 heteroatoms independently selected from oxygen, nitrogen and sulfur ring atoms;

each n is a number independently selected from zero to 40; and $Y^1$-$Y^3$ are independently selected from H; a group selected from a carboxyl, an amino, an alkoxycarbonyl, a RSC(O)—, a sulfonyl halide, a hydroxyl, an alkoxy, an —SH, an N-succinimidyl ester, an isothiocyanate, an iodoacetamide, a maleimidyl, a hydrazinyl, a hydrazide, a halogen, a cyano, a diazo, an azide, a guanidinyl, a sulfone, an epoxide, a diazirine, an alkenyl, an alkynyl, a phosphine, a silane and an alkylsulfonic acid; and a molecule of interest selected from a detectable label, a toxin, a peptide, a drug, a member of a specific binding pair, an epitope tag and a strained azacycloalkynone group, said contacting being under physiological conditions, wherein said contacting with said reactive partner results in a reaction between the azide group of the azide-modified cellular component and the cycloalkyne of the reactive partner, thereby synthetically and covalently modifying the cellular component to produce a covalently modified cellular component.

11. The method of claim 10, wherein said cellular component is a polypeptide.

12. The method of claim 10, wherein said contacting is in vitro or in vivo.

13. The method of claim 10, wherein the cell is not washed prior to said detecting.

14. The method of claim 10, wherein the method further comprises detecting the covalently modified cellular component.

15. The method of claim 10, wherein the modified cycloalkyne compound is of formula III:

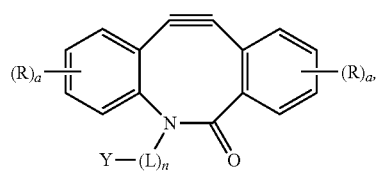

Formula III wherein each L is a divalent moiety independently selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, carboxamido, $C_1$ to $C_7$ acyloxy, urethanylene, sulfonyl, sulfonamido, —O—, —S—, —NH—, and substituted amino; wherein substituents of the substituted divalent moieties are selected from carboxy, amino, halo, hydroxy, nitro, cyano, trifluoromethyl, $C_1$ to $C_7$ alkyl, $C_1$ to $C_7$ alkoxy, $C_1$ to $C_7$ acyloxy, carboxamide, carboxymethyl, and hydroxymethyl; and wherein the substituted and unsubstituted heteroarylene and heterocyclene divalent moieties are five or six-membered rings having 1 to 4 heteroatoms independently selected from oxygen, nitrogen and sulfur ring atoms;

n is a number selected from zero to 40;

each R is independently selected from alkyl, substituted alkyl, alkoxy, substituted alkoxy, acylamino, acyloxy, amino, substituted amino, aminoacyl, aminoacyloxy, oxyaminoacyl, azido, cyano, halogen, hydroxyl, carboxyl, carboxylalkyl, —SH, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; wherein substituents are selected from carboxy, amino, halo, hydroxy, nitro, cyano, trifluoromethyl, $C_1$ to $C_7$ alkyl, $C_1$ to $C_7$ alkoxy, $C_1$ to $C_7$ acyloxy, carboxamide, carboxymethyl, and hydroxymethyl;

each a is a number selected from zero to four; and

Y is H; a group selected from a carboxyl, an amino, an alkoxycarbonyl, a RSC(O)—, a sulfonyl halide, a hydroxyl, an alkoxyl, an —SH, an N-succinimidyl ester, an isothiocyanate, an iodoacetamide, a maleimidyl, a hydrazinyl, a hydrazide, an aldehyde, a haloalkyl, a halogen, a cyano, a diazo, an azide, a guanidinyl, a sulfone, an epoxide, a diazirine, an alkenyl, an alkynyl, a phosphine, a silane, and an alkylsulfonic acid; or a molecule of interest selected from a detectable label, a toxin, a peptide, a drug, a member of a specific binding pair, an epitope tag and a strained azacycloalkynone group.

16. The method of claim 15, wherein the modified cycloalkyne compound is of the formula:

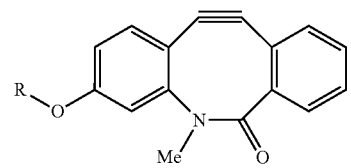

wherein R is selected from hydrogen, alkyl, sulfonate, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclyl, substituted heterocyclyl, sulfonyl, sulfonamide, amino and substituted amino; wherein the substituted and unsubstituted heteroaryl and heterocyclyl are five or six-membered rings having 1 to 4 heteroatoms independently selected from oxygen, nitrogen and sulfur ring atoms; and wherein substituents are selected from carboxy, amino, halo, hydroxy, nitro, cyano, trifluoromethyl, $C_1$ to $C_7$ alkyl, $C_1$ to $C_7$ alkoxy, $C_1$ to $C_7$ acyloxy, carboxamide, carboxymethyl, and hydroxymethyl.

17. The method of claim 15, wherein the compound is of formula V:

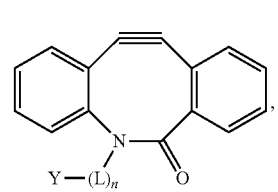

Formula V wherein each L is a divalent moiety independently selected from alkylene, alkenylene, alkynylene, arylene, cycloalkylene, heteroarylene, heterocyclene, acylamino, $C_1$ to $C_7$ acyloxy, urethanylene, sulfonyl, sulfonamido, —O—, —S—, and —NH—, and wherein the heteroarylene and heterocyclene divalent moieties are five or six-membered rings having 1 to 4 heteroatoms independently selected from oxygen, nitrogen and sulfur ring atoms;

n is a number selected from zero to 40; and

Y is H; a group selected from a carboxyl, an amino, an alkoxycarbonyl, a RSC(O)—, a sulfonyl halide, a hydroxyl, an —SH, an N-succinimidyl ester, an isothiocyanate, an iodoacetamide, a maleimidyl, a hydrazinyl, a hydrazide, an aldehyde, a haloalkyl, a halogen, a cyano, a diazo, an azide, a guanidinyl, a sulfone, an epoxide, a diazirine, an alkenyl, an alkynyl, a phosphine, a silane, and an alkylsulfonic acid; or a molecule of interest selected from a detectable label, a peptide, a member of a specific binding pair and an epitope tag.

18. The method of claim 15, wherein the compound is of formula VI:

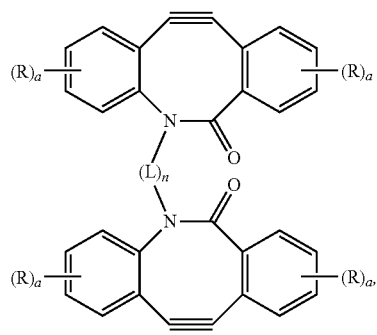

Formula VI wherein:
each L is a divalent moiety independently selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, carboxamido, $C_1$ to $C_7$ acyloxy, urethanylene, sulfonyl, sulfonamido, —O—, —S—, —NH—, and substituted amino; wherein substituents of the substituted divalent moieties are selected from carboxy, amino, halo, hydroxy, nitro, cyano, trifluoromethyl, $C_1$ to $C_7$ alkyl, $C_1$ to $C_7$ alkoxy, $C_1$ to $C_7$ acyloxy, carboxamide, carboxymethyl, and hydroxymethyl; and wherein the substituted and unsubstituted heteroarylene and heterocyclene divalent moieties are five or six-membered rings having 1 to 4 heteroatoms independently selected from oxygen, nitrogen and sulfur ring atoms;

n is a number selected from zero to 40;

each R is independently selected from alkyl, substituted alkyl, alkoxy, substituted alkoxy, acylamino, acyloxy, amino, substituted amino, aminoacyl, aminoacyloxy, oxyaminoacyl, azido, cyano, halogen, hydroxyl, carboxyl, carboxylalkyl, —SH, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl; wherein substituents are selected from carboxy, amino, halo, hydroxy, nitro, cyano, trifluoromethyl, $C_1$ to $C_7$ alkyl, $C_1$ to $C_7$ alkoxy, $C_1$ to $C_7$ acyloxy, carboxamide, carboxymethyl, and hydroxymethyl; and each a is a number selected from zero to four.

19. The method of claim 17, wherein the compound is of one of the following structures:

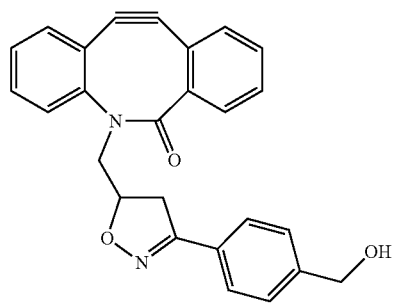

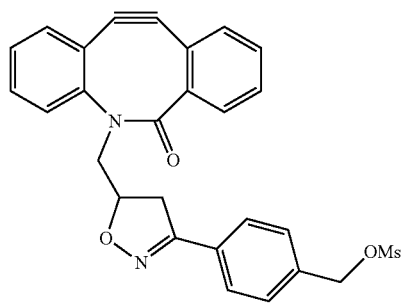

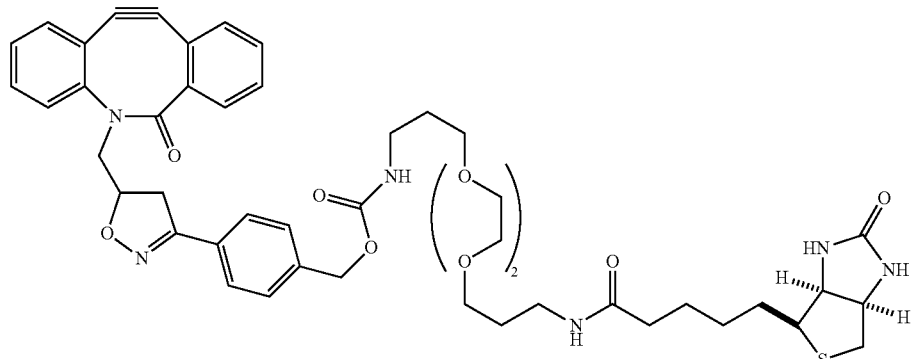

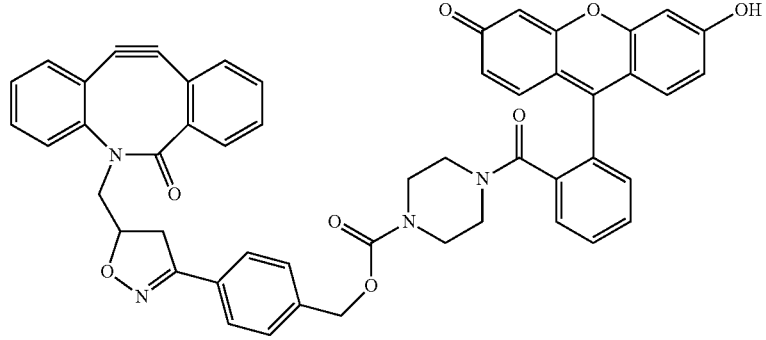

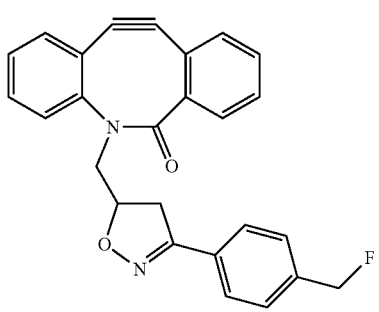
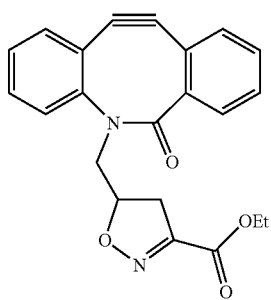
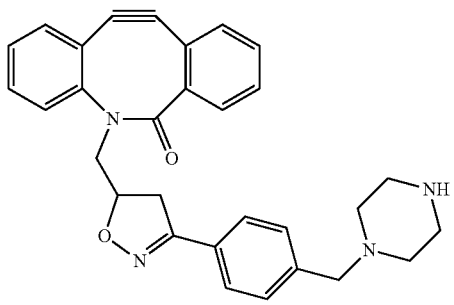
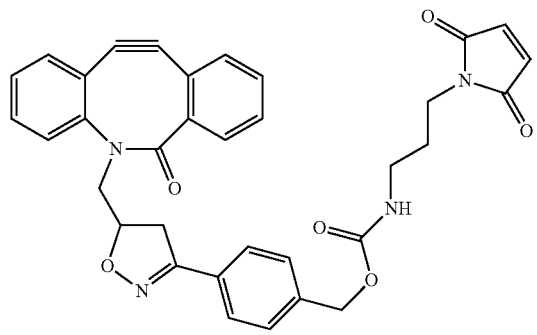
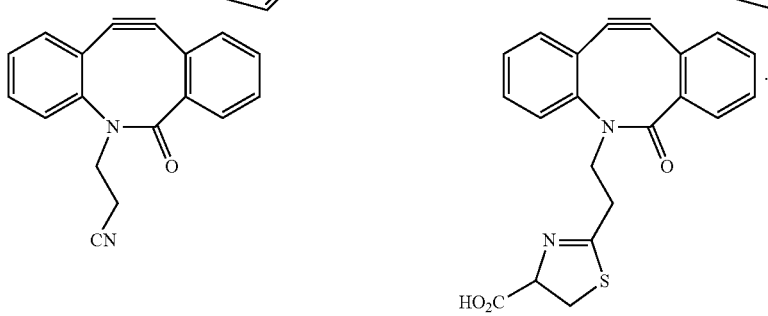

20. The method of claim 15, wherein the compound is of one of the following structures:

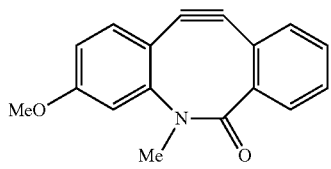

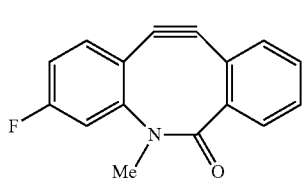

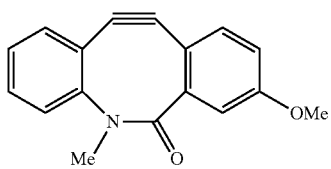

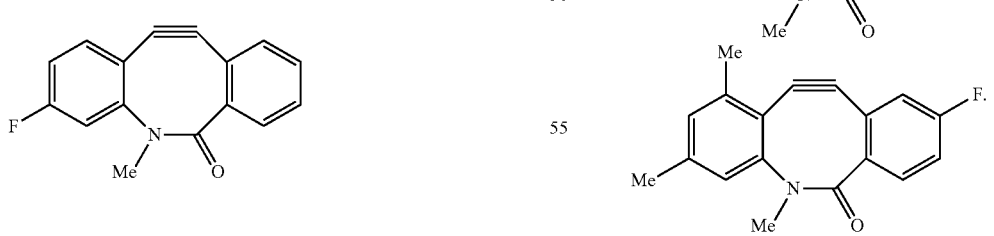

21. The method of claim 17, wherein:

each L is a divalent moiety independently selected from alkylene, arylene, cycloalkylene, heteroarylene, heterocyclene, $C_1$ to $C_7$ acyloxy, acylamino, urethanylene, sulfonyl, sulfonamido, —O—, —S—, and —NH—, and wherein the heteroarylene and heterocyclene divalent moieties are five or six-membered rings having 1 to 4 heteroatoms independently selected from oxygen, nitrogen and sulfur ring atoms;

n is a number selected from zero to 40; and

Y is selected from H, a carboxyl, an amino, a hydroxyl, an alkoxycarbonyl, an N-succinimidyl ester, a RSC(O)—, an isothiocyanate, an iodoacetamide, a maleimidyl, a hydrazinyl, a hydrazide, a halogen, an epoxide, a fluorophore, an epitope tag, and a biotin.

* * * * *

```
                          SEQUENCE LISTING

<160> NUMBER OF SEQ ID NOS: 12

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1

Cys Tyr Pro Tyr Asp Val Pro Asp Tyr Ala
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Asp Tyr Lys Asp Asp Asp Asp Lys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Asp Tyr Lys Asp Asp Asp Asp Lys Cys
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide

<400> SEQUENCE: 4

Cys Glu Gln Lys Leu Ile Ser Glu Glu Asp Leu
1               5                   10

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Gly Ser Gly Gly Ser
1               5

<210> SEQ ID NO 6
<211> LENGTH: 4
<212> TYPE: PRT
```

```
<213> ORGANISM: Artificial Sequence
<220> FEATURE:
<223> OTHER INFORMATION: Synthetic peptide

<400> SEQUENCE: 6

Gly Gly Gly Ser
 1

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide

<400> SEQUENCE: 7

Gly Gly Ser Gly
 1

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide

<400> SEQUENCE: 8

Gly Gly Ser Gly Gly
 1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide

<400> SEQUENCE: 9

Gly Ser Gly Ser Gly
 1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide

<400> SEQUENCE: 10

Gly Ser Gly Gly Gly
 1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide

<400> SEQUENCE: 11

Gly Gly Gly Ser Gly
 1               5

<210> SEQ ID NO 12
<211> LENGTH: 5
<212> TYPE: PRT
<213> ORGANISM: Artificial Sequence
<220> FEATURE:
```

<223> OTHER INFORMATION: Synthetic peptide

<400> SEQUENCE: 12

Gly Ser Ser Ser Gly
1               5